United States Patent [19]
Koch

[11] Patent Number: 5,377,011
[45] Date of Patent: Dec. 27, 1994

[54] SCANNING SYSTEM FOR THREE-DIMENSIONAL OBJECT DIGITIZING

[76] Inventor: Stephen K. Koch, 2804 Hunnicut Ct., Austin, Travis, Tex. 78748

[21] Appl. No.: 44,297

[22] Filed: Apr. 7, 1993

Related U.S. Application Data

[63] Continuation of Ser. No. 756,302, Sep. 6, 1991, Pat. No. 5,231,470.

[51] Int. Cl.⁵ ............................................. G01B 11/24
[52] U.S. Cl. .................................................... 356/376
[58] Field of Search ........................... 356/375, 376, 1; 364/561

[56] References Cited

U.S. PATENT DOCUMENTS 5,094,538  3/1992  Reedman et al. ..................... 356/376
5,231,470  7/1993  Koch .................................... 356/376

*Primary Examiner*—F. L. Evans
*Attorney, Agent, or Firm*—Baker & Botts

[57] ABSTRACT

A scanning system for a three-dimensional object digitizing system comprises circuitry for directing a set of sequential light beams to a plurality of points on an object. The light beams are directed by the normalizing circuitry to be normal to the surface of the object at the point of incidence. With this orientation, the scanning system associates with the ranging system for the determination of a set of a range measurements to the points on the object. Circuitry of the scanning system predicts the location of a point on the surface as a function of a plurality of previously measured points. Additional circuitry adaptively pivots the light beams away from the normal incidence angle to reach a plurality of points in response to a measurement substantially deviating from the predicted point. The scanning system redirects subsequent light beams to be incident on the surface upon the occurrence of a predetermined set of conditions and continues to provide normal incidence angles and pivoting incidence angles for points around the contour of the object being scanned.

52 Claims, 19 Drawing Sheets

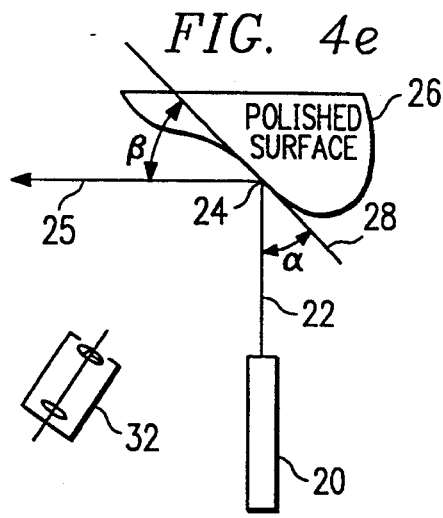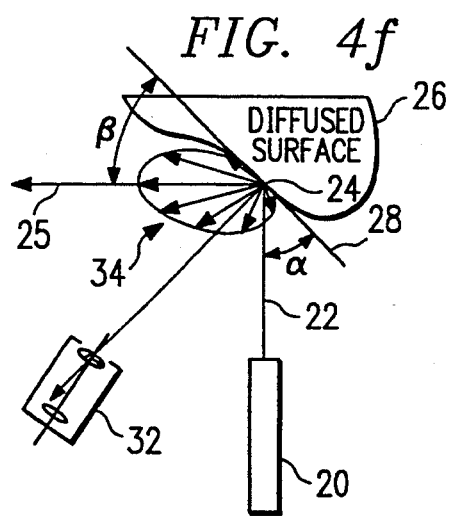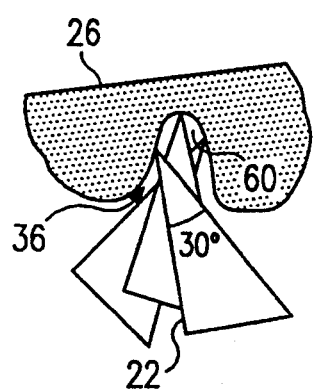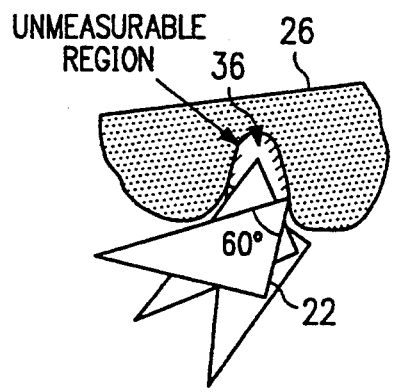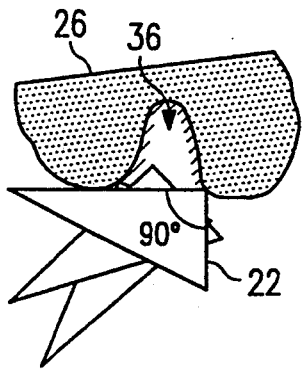

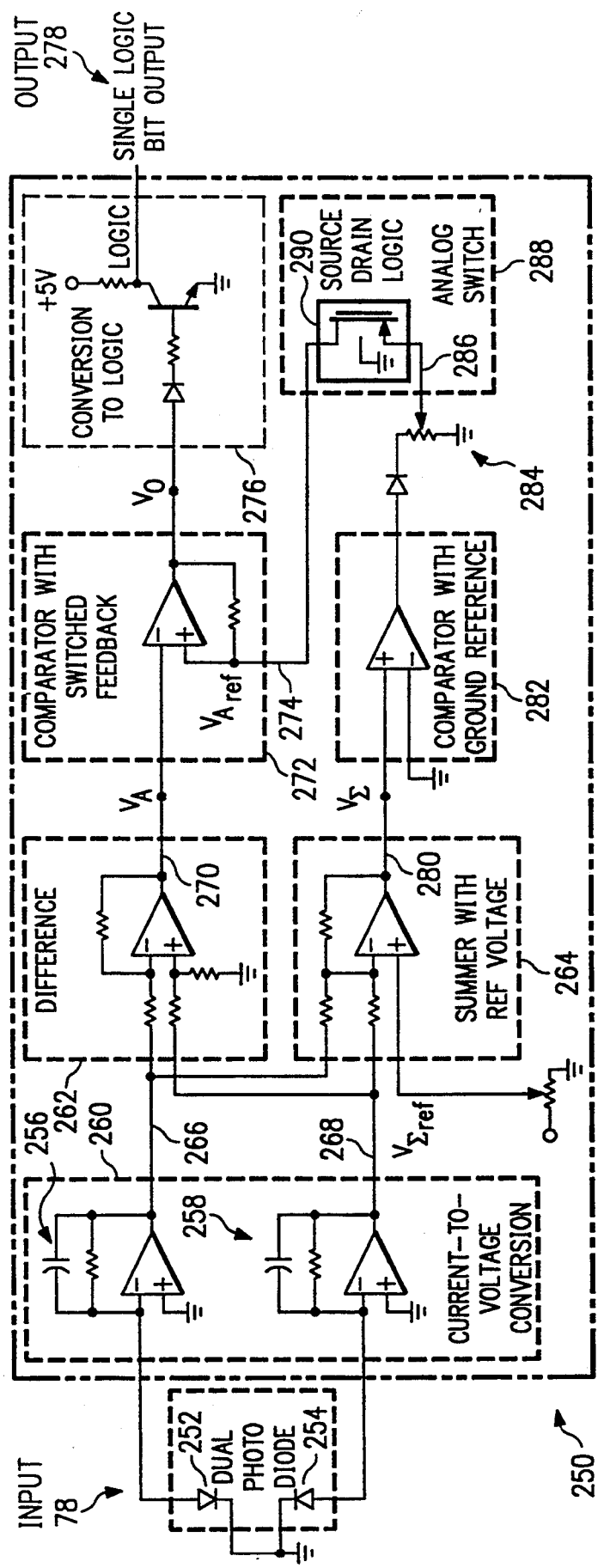

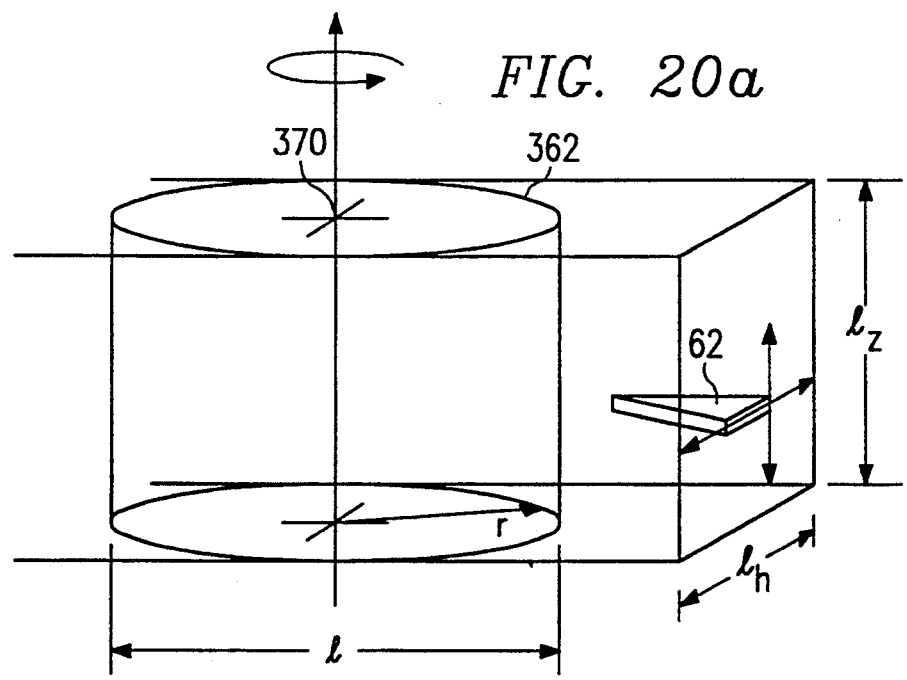
FIG. 20a
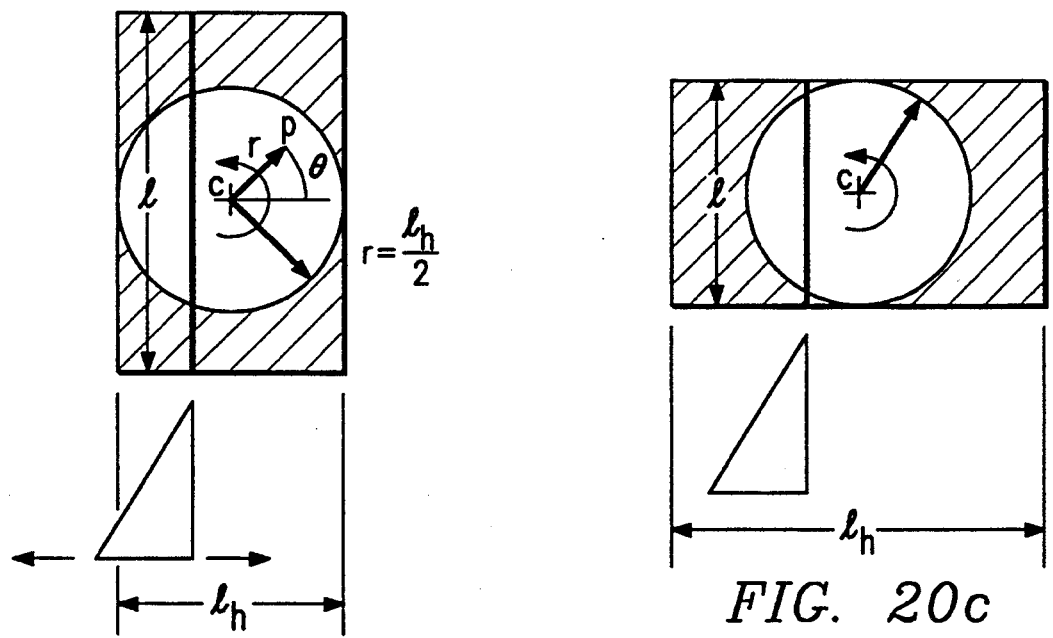
FIG. 20b
FIG. 20c

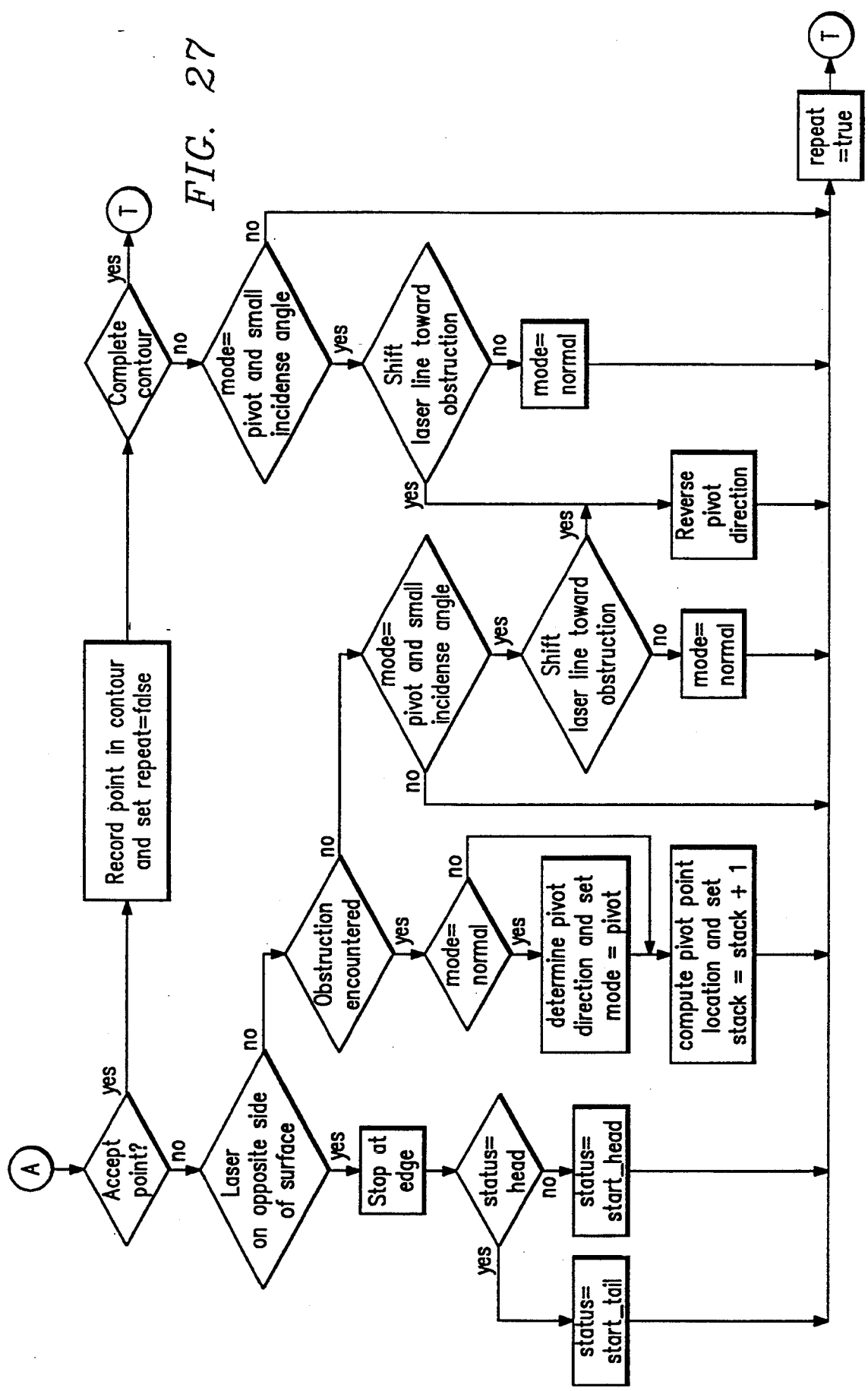

SCANNING SYSTEM FOR THREE-DIMENSIONAL OBJECT DIGITIZING

CROSS REFERENCE TO RELATED APPLICATIONS

This application is a continuation application of U.S. application Ser. No. 07/756,302, filed Sep. 6, 1991 and entitled "Scanning System for Three-Dimensional Object Digitizing", now U.S. Pat. No. 5,231,470, issued Jul. 27, 1993.

TECHNICAL FIELD OF THE INVENTION

This invention relates in general to a system for measuring ranges to the exposed surface of a complex-shaped object and more particularly to a three-dimensional object digitizing method and system for producing high-resolution, accurate range measurements between the surface of a three-dimensional object and a known point.

BACKGROUND OF THE INVENTION

For a variety of computerized applications, it is desirable to measure the surface geometry of a three-dimensional (3-D) object by acquiring a multitude of data points that may be used for 3-D computation purposes or for 3-D display on a computer screen. Applications for object digitizing include anatomical/medical imaging and analysis; prosthesis design and manufacturing; animation/imaging applications; computer aided design (CAD) modeling; prototype design and develop; model, sculpture, and part duplication; stereolithography and laser-sintering data acquisition; as well as quality assurance and analysis.

Although a variety of methods and systems exist for acquiring surface data for these applications, no single method or system provides an economical and general solution to the object digitizing problem. One method to digitize objects in 3-D uses radiometric imaging (e.g., CAT scan nuclear magnetic resonance, or ultra-sound technologies). For medical diagnostic purposes these techniques are attractive, because they are fully-automated, fast, and may be safely applied to living subjects. For other purposes, however, these methods and the systems employing them are woefully inadequate. This is primarily due to their relatively high expense and lack of object image accuracy and resolution.

Another known type of system includes robotic tactile 3-D digitizers (i.e., machines that physically touch the surface of an object). While these machines provide high degrees of accuracy and resolution, they unfortunately are relatively slow and clumsy. This is because these types of machines must take precautions to prevent any disruptive or invasive contact between the digitizer and the object. For complex objects, obstruction avoidance makes tactile 3-D digitizers highly sophisticated and makes it necessary for them to possess robust sensing systems. Robotic tactile 3-D digitizers, therefore, are generally very expensive, slow, and limited to applications with simple, well-defined environments where the geometry of the object is partially known by the system prior to digitizing.

In an effort to overcome the expense and other limitations of the above methods and systems, active digitizing techniques have been developed. These techniques project energy to the object and measure the properties of any reflected energy image to determine the deflection location at the surface. These methods are attractive because they are non-destructive, relatively accurate and sufficiently resolute for many purposes. Digitizing speed may vary significantly depending on how much of the surface the digitizer illuminates and how many degrees of mechanical freedom exist between the object and the energy source. A degree of freedom simply describes the mechanical ability to move a sensor relative to the object. For example, a system in which an object may rotate about a central axis and the sensor translates up and down is said to have two degrees of freedom (DOFs).

Systems which employ two translational DOFs (i.e., vertical and horizontal translations) between the object and the ranging device may sample at rates up to 100,000 points per second. Systems utilizing three or more DOFs typically obtain as few as 10,000 points per hour. This slower sampling rate is directly attributable to the fact that positioning with 3 and 4 DOFs requires more time.

Probably the most popular type of 3-D digitizers use active triangulation of light energy. These devices are generally the most attractive approach available for accurate, high-resolution, non-destructive and fast surface measurement. Improved sampling speeds are typically obtained by using patterned light projection. Sophisticated lighting patterns require specialized two-dimensional sensors such as charged coupled device (CCD) cameras and extensive image processing facilities. While these digitizers may be fast, the electronic hardware they use is generally expensive, complicated, unreliable, and limited in application. The simplest form of pattern lighting is produced by projecting a single plane of light to the object. The linear surface contour illuminated by a plane of light may be quickly digitized with a CCD detector producing a large number of points for each line. The number of points typically equals the resolution of the CCD array detector. This technique is very popular and is commercially available from a variety of vendors.

Unfortunately, while this system provides rapid sampling rates, light-plane projection limits the application of these systems to simple convex surfaces that require only two translational degrees of mechanical freedom between the object and the light projector. If more degrees of freedom are used, this type of system will produce large amounts of redundant surface sampling which must be identified and removed when processing the subsequent large amount of acquired data.

It is important to recognize that these methods utilize imaging optics in which the reflected light from the object surface is collected and pseudo-focused onto a linear or planar array detector. This off-axis photo direction sensor method of active triangulation is basically a wide angle camera system for imaging the illuminated surface on to a detector. Disadvantages to this approach include variable accuracy and resolution, the need for calibration procedures, and the inability to employ scanning procedures that use more than two translational degrees of freedom without introducing sample redundancy. Variable accuracy and resolution of the off-axis photo direction sensors are a result of (1) a fuzzy image due to the inability to focus on the object; (2) the optics of this method produce large non-linear image distortions; (3) as the triangulation angle decreases, the accuracy and the resolution of the image also decreases; and (4) the accuracy and resolution of this technique is also limited by the accuracy and resolution of the detector.

As a result of the above, it is clear that there is the need for a 3-D object digitizing method and system that is relatively inexpensive and useful to measure ranges between a known point and points on the surface of an object for a wide variety of complex shaped objects.

There is the need for a 3-D object digitizing method and system that accurately provides geometrically and topologically complete high-resolution surface data.

There is a need for a method and system for 3-D object digitizing that eliminates measurement redundancy and has the ability to use a large variety of scanning procedures using different combinations of 2, 3 and 4 degrees of freedom.

Furthermore, in many situations, it is inappropriate to mathematically model a surface. When a physical model exists or can be constructed, it can be much more efficient to simply measure the surface and avoid any mathematical representation. Thus, there is a need for a 3-D object digitizing system that avoids the need to mathematically model a surface to provide accurate, high resolution 3-D object data.

Furthermore, there is the need for a 3-D object digitizing method and system that provides the ability of advanced interfacing with a wide variety of computer processing devices.

SUMMARY OF THE INVENTION

The present invention, accordingly, provides a scanning system for a 3-dimensional object digitizing system that overcomes limitations associated with known methods and systems. The present invention provides adaptive scanning capable of operating in both a normalizing and pivoting mode to assure high resolution data for objects scanning across a large work volume.

According to one aspect of the invention, there is provided a scanning method and system for a 3-dimensional object digitizing system that comprises circuitry for directing a set of sequential light beams to a plurality of points on an object at an incidence angle normal to the surface of the object at the point of incidence. By positioning the light beams in this way, the scanning system of the present invention permits a ranging system to obtain triangulation range measurements. Circuitry within the scanning system of the present invention predicts the location of a point on the surface as a function of previously measured points. Additional circuitry adaptively pivots the light beams away from the normal incidence angle in the event that it is necessary to deviate from the normal in order to reach the points with the light beams. The pivoting circuitry assist in obtaining range measurements for a complete contour of an object. Further circuitry of the present invention redirects the subsequent light beams to be normal to the surface in the event that the pivoting mode satisfies a predetermined set of conditions. These conditions typically relate to the angle at which the light beams illuminate the surface of the object. Further circuitry within the present invention controls the normalizing circuitry and the pivoting circuitry to derive a complete measurement of the shape of the object using an associated ranging system.

The ranging system of present invention provides high-quality surface measurements by using three mechanical degrees of freedom (DOF) i.e., one rotational DOF for rotating the object and two translational DOFs for positioning the laser source. Using three DOFs, the ranging system effectively "walks" the laser beam from point to point along the object's surface while actively minimizing the incidence angle between the laser beam and the local surface normal. Complete measurement of the exposed surface of a complex-shaped object requires one rotation and two translations between the object and the ranging system. The object digitizing system of the preferred embodiment, therefore, makes this possible.

A technical advantage of the present invention is that it is self-orienting and maintenance free. No calibration or adjustment is necessary either before or during the digitizing procedure. As a result, significant time and labor cost savings in performing sequential object digitizing procedures result.

Additionally, a technical advantage of the object digitizing system of the present invention is that it provides high resolution and accuracy typical of labor-intensive and expensive methods at low capital costs and without the need of significant operator experience or expertise.

Another technical advantage of the present invention is that it may utilize adaptive scanning procedures to minimize shadowing effects, provide optimal measurement orientations, and produce equal-point spacing with no measurement redundancy. This provides the present invention with the significant data compilation and analysis advantage over the existing triangulation methods that use imaging optics to perform off-axis photo-direction detection.

Another technical advantage of the present invention is that by providing advanced positioning capabilities, the system yields complete, one-scan measurement of complex objects having deep concavities and split contours.

Another technical advantage of the present invention is that by adding the extra mechanical positioning capability through the third degree of freedom in the present invention, it is possible to position the laser line of a laser digital ranging system at more measurement positions about the surface of an object. Moreover, the adaptive scanning algorithm of the present invention provides the means to efficiently locate the optimum measurement orientation between the ranging system and the object for a 3-D digitizing system. By using the geometry of previously acquired points to predict the contour of the object surface, the adaptive scanning algorithm keeps the laser line normal to the surface for convex surfaces. For other shapes, the system uses the pivoting mode to very efficiently provide optimal measurement orientations by maneuvering to acquire range points deep in surface concavities and in between split contours.

As a result, yet another and important technical advantage of the present invention is that the present invention provides for digitizing complex-shaped objects having much more surface area that can be measured and many more acquired surface points that are evenly spaced among one another with absolutely no measurement redundancy. That is, no point in an object digitizing operation that uses the scanning method and system of the present invention is ever measured twice. The result is that the present invention provides the most complete and concise set of data that can possibly be obtained with the very efficient method of triangulation ranging.

BRIEF DESCRIPTION OF THE DRAWINGS

The invention and its modes of use and advantages are best understood by reference to the following description of illustrative embodiments when read in conjunction with the accompanying drawings, wherein:

FIGS. 4a–4f illustrate characteristics associated with active triangulation of various surface points and characteristics;

FIGS. 5a–5c illustrate characteristics of various probing angles for active triangulation of object surfaces;

FIGS. 13 and 14 provide schematic diagrams and output characteristics for the photodiode signal processing circuit of the preferred embodiment of the present invention;

FIGS. 20a–20c illustrate the three degree of freedom scanning work volume for the preferred embodiment of the present invention.

FIGS. 26 and 27 provide a flow chart of the three degree of freedom adaptive scanning procedure;

APPENDIX A provides a listing of the computer code for the range measurement procedure of the preferred embodiment of the present invention;

APPENDIX B provides a listing of the source code for the adaptive three degree of freedom scanning of the preferred embodiment of the present invention.

DETAILED DESCRIPTION OF THE INVENTION

The preferred embodiment of the present invention is best understood by referring to the FIGUREs wherein like numerals are used for like and corresponding parts of the various components.

Figure 1A:
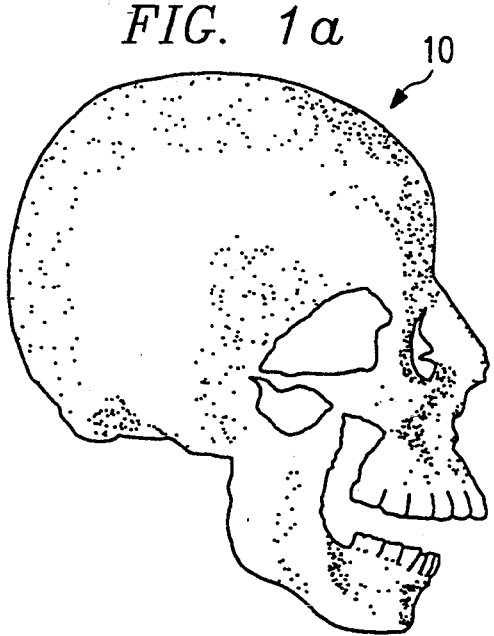
FIGS. 1a and 1b illustrate a human skull and the digitization of the human skull using the preferred embodiment of the present invention.

The object digitizing system of the preferred embodiment has the ability to measure relatively complex 3-D objects using adaptive and closed-loop scan control and facilitates the use of enhanced data processing capabilities. For example, FIGS. 1a, 1b, 2a, and 2b illustrate types of digitization that the preferred embodiment has the ability to perform. FIG. 1a shows a human skull 10 that the preferred embodiment has digitized to produce the surface mesh 12 of FIG. 1b. Similarly, FIG. 2a shows a human pelvic bone 14 that the preferred embodiment digitized to produce the 3-D surface mesh 16 of FIG. 2b.

Figure 1B:
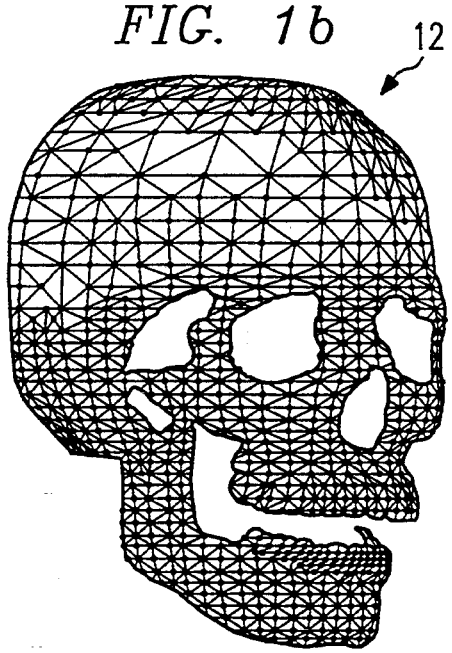
Figure 2A:
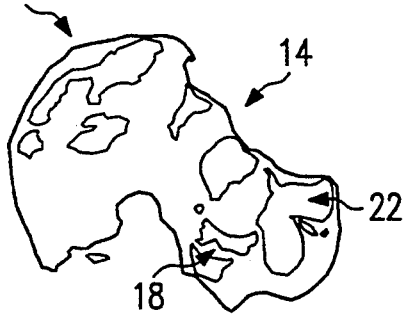
FIGS. 2a and 2b illustrate the digitization of a human pelvic bone using the preferred embodiment of the present invention.
Figure 2B:
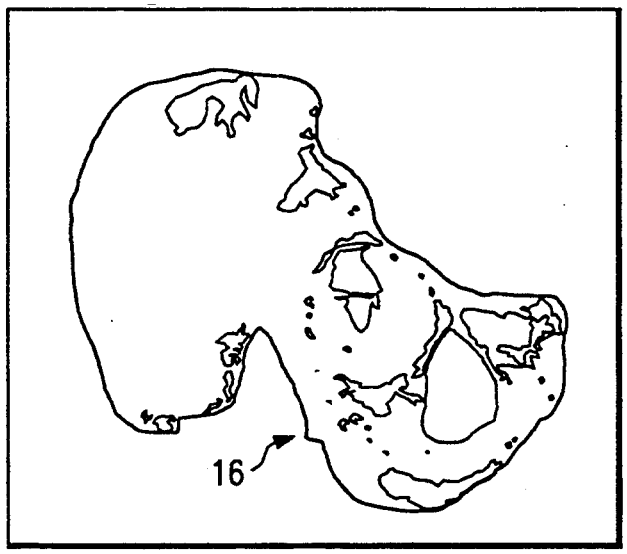

Conventional active ranging systems that use charge couple device (CCD) optical arrays may be able to produce a mesh similar to the human skull mesh 12 of FIG. 1b. Referring to FIGS. 2a and 2b, however, because of the concavities 18 and 20 of the split contour 22 of the human pelvic bone 14, conventional CCD-based devices cannot produce a mesh that approximates the quality of mesh 16 in the shape of the human pelvis. It is not possible to easily digitize the pelvis. Using the preferred embodiment, however, both the human skull 10 and the human pelvic bone 14 were easily digitized producing surface mesh of between 4 and 5 thousand polygons.

There are numerous other examples that can be provided where discontinuities, extreme concavities, and other surface problems exist that make 3-D object digitizing nearly impossible using conventional methods. These applications, however, are clearly within the scope of practical applications for the preferred embodiment of the present invention. Not only does the preferred embodiment solve these complex surface characteristics digitization problems, but it also does so in a much more reliable way that minimizes the need for operator intervention.

Figure 3:
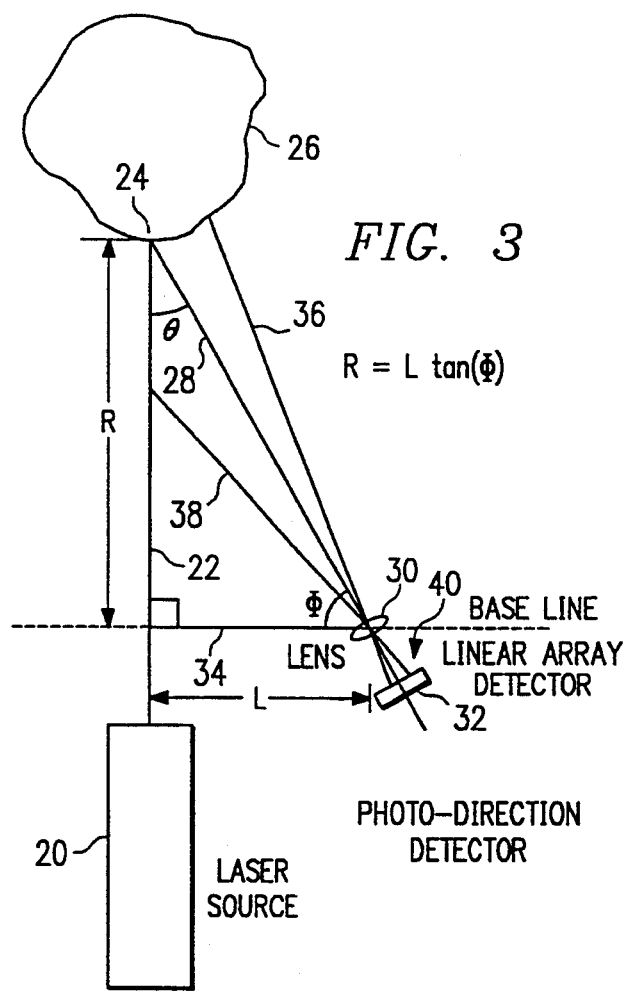
FIG. 3 conceptually illustrates conventional active triangulation methods and systems.

In order to fully understand the 3-D object digitization system of the preferred embodiment, it is helpful to appreciate basic concepts of conventional active ranging systems that use imaging optics. Referring to FIG. 3, consider that laser source 20 emits a laser beam along a laser line-of-sight 22 to surface point 24 on object 26. At surface point 24, a portion of the laser beam reflects along the view line-of-sight 28 through lens 30 to linear array detector 32. Baseline 34 is perpendicular to laser line-of-sight 22, the angle $\Phi$ between view line-of-sight 28 and baseline 34 may be measured by the system, and the perpendicular distance L from the laser line-of-sight to the center of lens 30 may be determined. Using simple trigonometry, therefore, it is possible to determine the perpendicular distance R from baseline 34 to surface point 24 according to the following equation:

$$R = L \tan(\Phi) \quad (1)$$

Known active triangulation devices for object surface digitizing that use optical imaging systems, such as that of FIG. 3, project an energy beam off-axis to a linear array detector 32. These systems use imaging optics to correlate the received light to the light that actually appears at surface point 24. Because these systems must correlate the sensed light to surface point 24, the received signal is not a focused or exact point, but a "fuzzy point." Additionally, because of non-linearities characteristically inherent in imaging optics, elaborate calibration procedures are necessary for these systems to accurately correlate the surface point location 24 to the image point position of the linear array detector 32. For example, what actually reaches linear array detector 32 is the combination of light collected images within the field of view bounded by lines-of-sight 36 and 38. Through lens 30, the light within this optical span focuses onto linear array detector 32 as the optical span 40. This optical span must be mathematically filtered using a sophisticated statistical procedures to determine an approximation of the 3-D position of the image of surface point 24.

Systems using these expensive and complicated CCD or imaging optical arrays also require extensive calibration procedures. The calibration procedures require placing a known object having known dimensions a known distance from the laser source and measuring the known objects to create a calibration table. With the calibration table, these systems attempt to remove the non-linear distortions from the image. The calibration procedures may take as long as 10 to 30 minutes to complete for each digitizing operation. Even after a successful calibration procedure, conventional CCD or imaging optics digitizing systems may go out of calibration during a single digitizing operation. This makes it essential that a system operator continuously monitor the imaging optics digitizing systems during each calibration procedure. The need to continually monitor the imaging optics systems practically prohibit making the digitizing process fully automatic. This, however, is not a problem with the method and system of the preferred embodiment.

Figures 4A, 4B, 4C, 4D:
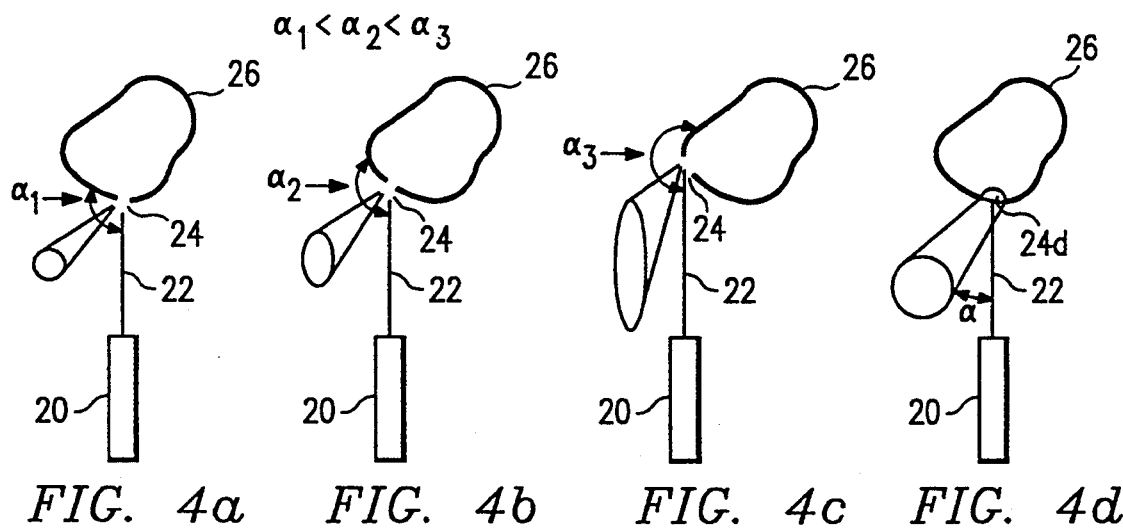

In any system that uses active triangulation similar to that of FIG. 3, it is necessary to understand that there are certain surfaces for which digitization is not possible. FIGS. 4a through 4f illustrate observable phenomena characteristic of all triangulation-based active ranging methods. FIGS. 4a through 4c illustrate that large incidence angles (i.e., $\alpha_1$, $\alpha_2$, $\alpha_3$) produce elongated deflection spots. FIG. 4d shows that a semi-transparent surface will "glow" producing a larger spot 24d.

Other characteristics of active ranging measurements with laser illumination are that for a polished surface, as FIG. 4e illustrates, most of the light from laser line 22 is reflected from point 24 to line 25 so that the angle of reflection $\beta$ from plane 28 equals the angle $\alpha$ between the laser line 22 and plane 28. Plane 28 is tangent to the surface of object 26 at point 24. In this situation, photo-detector 32 will see very little, if any, reflected light from surface point 24. On the other hand in FIG. 4f, for a diffuse surface, laser light beam 22 again goes to point 24 which has surface tangent 28. Because object 26 has a diffuse surface, however, light scatters in many directions within span 34. Although the maximum beam of reflective intensity is still along reflected line 25, at least some of the incident light at point 24 scatters to photo detector 32. Active triangulation is, therefore, possible for the diffuse surface object 26.

Yet another limitation with triangulation systems in general is that there is a physical limit obtaining range measurements of points in deep concavities. FIGS. 5a through 5c show this measurement limitation. As the surface concavity increases, a photo detector's view of points located within concave region 36 becomes increasingly obstructed. This produces increasingly limited laser photo detector orientations. FIGS. 5a through 5c show three different probing angles; FIG. 5a shows a 30° probing angle; FIG. 5b a 60° probing angle; and FIG. 5c a 90° probing angle. In varying degrees these probing angles are successful in scanning the concave region 36 of object 26. As FIGS. 5a–5c illustrate, reduced probing angles provide improved ability to scan into concave region 36. On the other hand, reducing the probing angles introduces a further limitation. In particular, reduced probing angles decrease measurement resolution and accuracy. For most applications, a 30° probing angle provides a measurement error of better than 0.1% of the ranging length. For most applications, therefore, a 30° probing angle provides adequate resolution and accuracy while adequately penetrating most surface concavities.

Recognizing general limitations, the preferred embodiment of the present invention provides improved accuracy and resolution combined with system reliability for active triangulation. The result is that the preferred embodiment yields superior performance over conventional active triangulation methods and systems.

Figure 6:
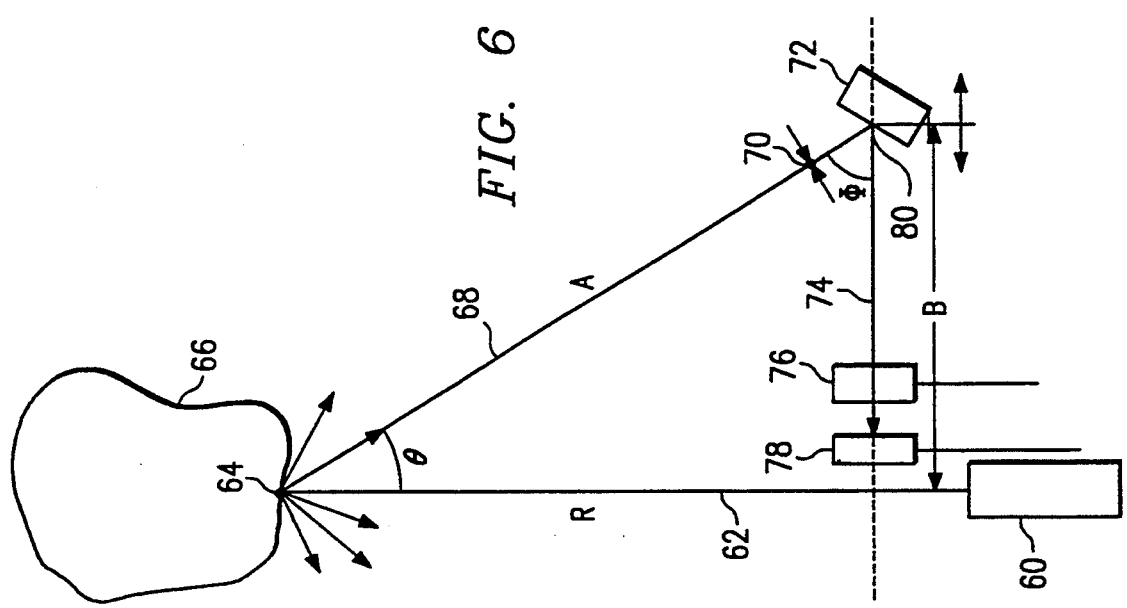
FIG. 6 conceptually illustrates fundamental characteristics of the preferred embodiment of the present invention.

To illustrate the basic concepts of the present invention, FIG. 6 shows a simplified conceptual representation of the ranging method for object digitizing that the preferred embodiment employs. The object digitizing method and system of the preferred embodiment provide a simple, elegant and inexpensive way of digitizing a 3-D object that does not rely on imaging optics. Referring more particularly to FIG. 6, laser source 60 emits a laser beam along a laser line-of-sight 62 to surface point 64 of object 66. Reflecting from surface point 64, the light of laser source 60 scatters out in all directions. In particular, at least a portion of the light from the laser source 60 scatters at an angle $\Theta$ from laser line-of-sight 62 along view line-of-sight 68. The light that scatters along view line-of-sight 68 passes through aperture 70 to translating mirror 72 and is reflected along base line-of-sight 74 through laser band pass filter 76 to photodiode sensor 78.

Base line-of-sight 74 is orthogonal to laser line-of-sight 62, and angle $\Theta$, between view line-of-sight 68 and base line-of-sight 74, is predetermined as part of the ranging system configuration. In the preferred embodiment, the distance between the point 80 of translating mirror 72 at which the light from view line-of-sight 68 reflects to baseline-of-sight 74 and laser line-of-sight 62 is measurable and determines the measurement of the range R. (See Equation (1), above) In other words, since the angle $\Phi$ between view line-of-sight 68 and baseline-of-sight 74 is fixed, the distance R may be calculated as the tangent of the angle $\Phi$ multiplied by the baseline-of-sight 74 distance B.

Aperture 70 is a critical component of the triangulation method of the preferred embodiment. Aperture 70 forms an optical pivot between the light scattering from surface point 64 and the light that photodiode sensor 78 receives. Mirror 72 only bends the optical system for triangulation calculations. It is aperture 70 that controls the length B from which triangulation calculations may be made. Only when the light passing through aperture 70 is at the physical center of photodiode sensor 78 can the system measure the length of baseline-of-sight 74. The use of aperture 70 for this purpose yields highly accurate surface point measurements. The operation of aperture 70 and photodiode sensor 78 are discussed more fully below at FIG. 11 and associated text.

In addition to the configuration that FIG. 6 shows, the preferred embodiment uses a collecting lens to focus more light from point 64 to photodiode sensor 78. This focusing may be important as the separation between laser source 60 and photodiode sensor 78 increases. Bandpass filter 76 removes background noise to increase the signal-to-noise ratio of the light incident on dual photodiode 78.

Figure 7:
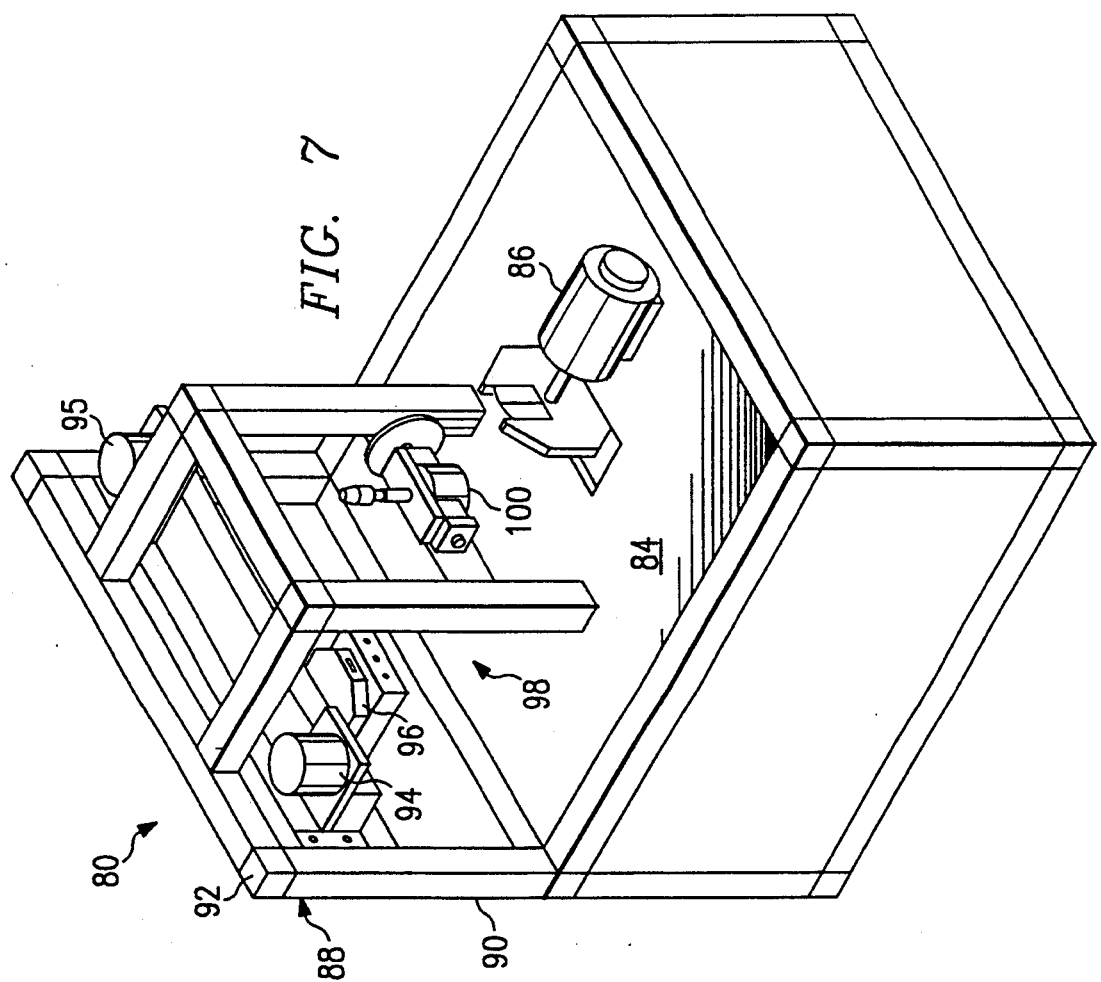
FIG. 7 provides a simplified isometric schematic of the preferred embodiment of the present invention.

With these general concepts in place, it is now appropriate to introduce the preferred embodiment and explain how it accomplishes the purposes of the present invention. FIG. 7 shows an isometric view of the 3-D object digitizing system 80 of the preferred embodiment that incorporates the active triangulation ranging concepts of FIG. 6. Control of the object digitizing system 80 is possible through a microcomputer which may connect to circuitry within object digitizing system 80 to control both the electronic and mechanical system operations. On base 84 appears stepper motor 86 and ranging manifold 88. Ranging manifold 88 includes support beams 90 for supporting laser and bearing assembly 92. On laser and bearing assembly 92 appears stepper motors 94 and 95 translating aperture collecting lens and triangulating mirror enclosure 96. Attached to laser and bearing assembly 92 and base 84 is support structure 98 for pedestal assembly 100. Pedestal assembly 100 and stepper motor 86 are integral components of the scanning portion of the 3-D object digitizing system of the preferred embodiment. Their operation is discussed more particularly in connection with general and detailed discussion of the scanning system within the preferred embodiment.

The preferred embodiment of the 3-D object digitizing system may be considered to comprise a ranging system and a scanning system. The ranging system takes a range measurement and digitizes that measurement according to a well-defined logic flow. For each of these measurements, the 3-D object digitizing system of the preferred embodiment uses a scanning system to optimize the way that the ranging system measures points on the object.

Figure 8:
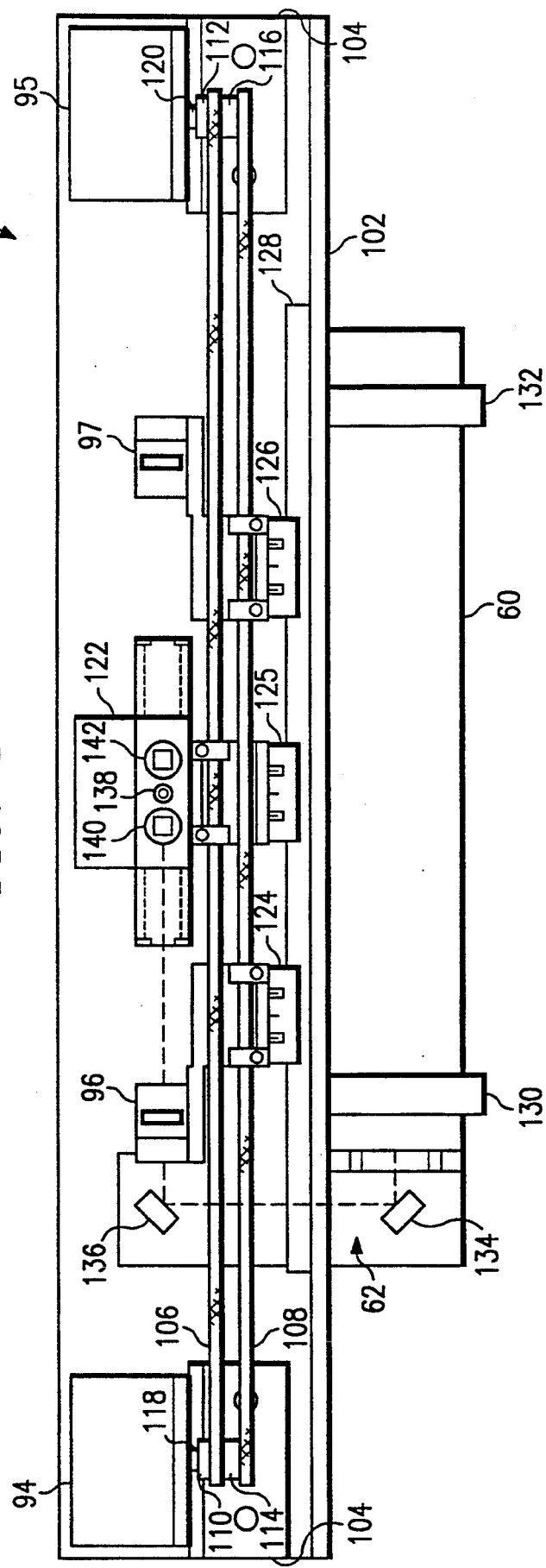
FIG. 8 provides a front view schematic of the preferred embodiment of the present invention.

Referring more particularly to laser and bearing assembly 92, FIG. 8 shows laser source 60 attached to base 102 of laser and bearing assembly 92. At mounts 104, stepper motors 94 and 95 attach to timing belts 106 and 108. Pulleys 110 and 112 of stepper motors 94 and 95, respectively, hold in place timing belt 106, and pulleys 114 and 116, respectively, hold timing belt 108 in place. Pulleys 110 and 114 for stepper motor 94 are associated to a single shaft 118, but in the preferred embodiment pulley 110 is a free pulley and 114 is a fixed pulley. Conversely, pulley 112 of stepper motor 95 is a fixed pulley and pulley 116 is a free pulley both attached to shaft 120 of stepper motor 95. Attached to timing belt 106 is linear bearing block 125 which is integral to translating laser beam projector and light sensor enclosure 122. Linear bearing blocks 124 and 126 attach to timing belt 108. Translating laser beam projector and light sensor enclosure 122 and linear bearing blocks 124 and 126 all ride along linear rail 128 which attaches to base 102 of laser and bearing assembly 92. Linear bearing block 124 supports and is integral to translating aperture, collecting lens and triangulating mirror enclosure 96 and linear bearing block 126 supports and is integral to translating aperture, collecting lens, and triangulating mirror enclosure 97.

Laser light source 60 is held in place by mounts 130 and 132 to emit laser light to laser beam directors 134 and 136. Laser directors 134 and 136 direct the laser output of laser source 60 to translating laser beam projector and light sensor enclosure 122. The configuration of laser source 60 above and integral to laser and bearing assembly 92 makes the preferred embodiment compact and permits the laser light to emanate from output 138 by being directed through a further beam director (not shown) within translating laser beam projector and light sensor enclosure 122. Enclosure 122 also contains two incidence detectors 140 and 142 that generate signals to determine whether a laser beam from output 138 is hitting an object within the digitization work volume.

Figure 9:
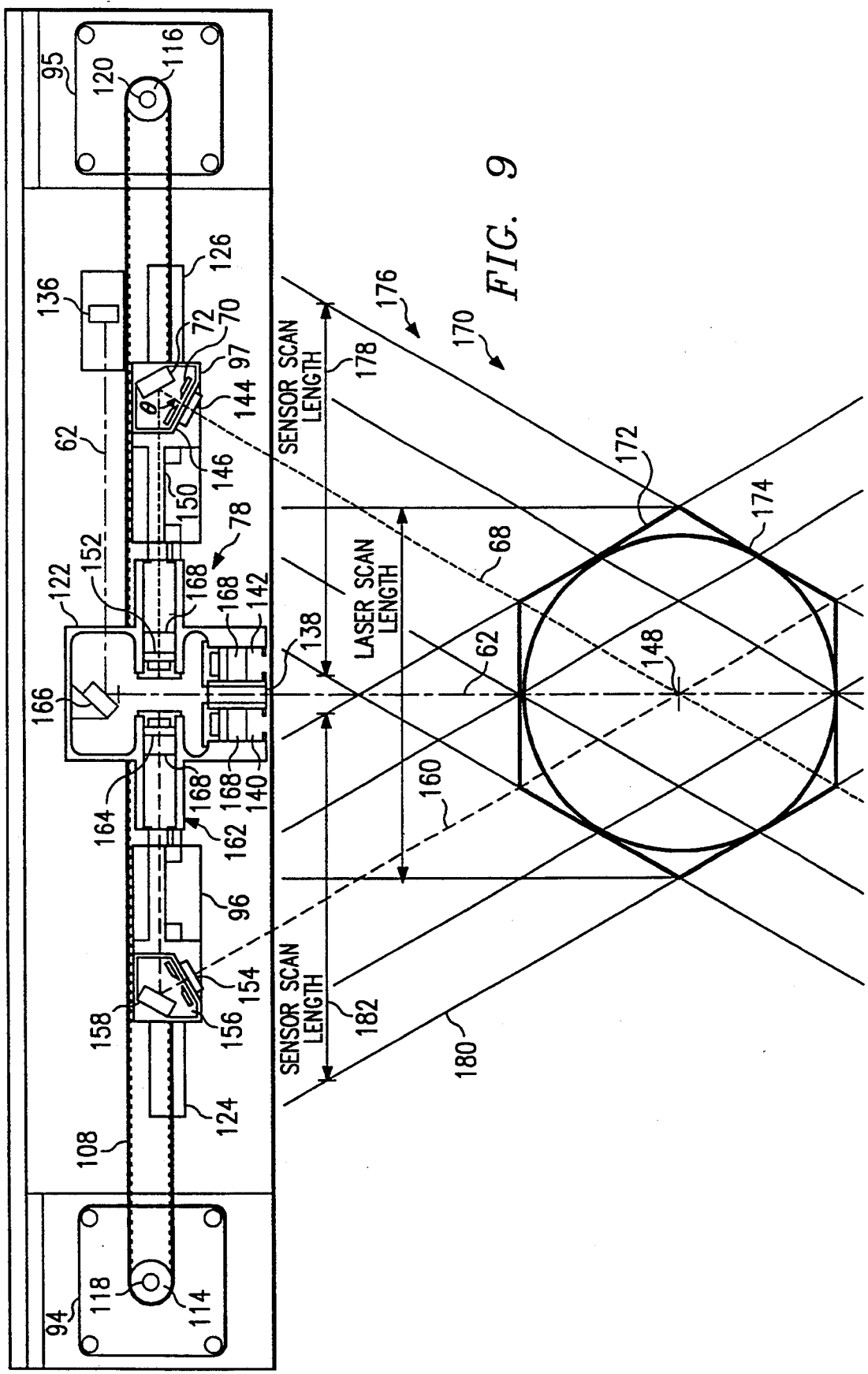
FIG. 9 illustrates a bottom-view schematic diagram of the preferred embodiment of the present invention.

To more fully understand the operation of the components of the preferred embodiment, FIG. 9 provides a bottom-view, partially cut-away schematic of the preferred embodiment. As FIG. 9 shows, stepper motors 94 and 95 have shafts 118 and 120 stemming from their base on which lower pulleys 114 and 116, respectively, support lower timing belt 108. Attached to lower timing belt 108 are linear bearing blocks 124 and 126. Linear bearing blocks 124 and 126, as stated above, are integral to enclosures 96 and 97, respectively. Between enclosures 96 and 97 is translating laser beam projector and light sensor enclosure 122. FIG. 9 provides partially cutaway views for enclosures 96, 97 and 122. Referring to enclosure 97, collecting lens 144 attaches to and permits light passage through to casing 146 which contains aperture 70 and reflecting mirror 72.

At the angle Φ, light is reflected within enclosure 97 through passage 150 to photodiode sensor 78. Sensor 78 contains dual photodiode 152 which senses the light and reports this sensing to the dual photodiode sensing circuitry of the preferred embodiment.

With opposite orientation to enclosure 97, enclosure 96 contains a similar collecting lens 154, aperture 156, and translating mirror 158 for translating light beam 160 from point 148 into photodiode sensor 162 to be read by photodiode pair 164. Enclosures 96 and 97 are opposite in orientation but rigidly fixed to timing belt 108 in the preferred embodiment.

Enclosure 122 contains laser directing mirror 166 that receives laser beam 62 and directs it through opening 138 to point 148. Enclosure 122 contains photodiode sensor 78 and 162 and further includes incidence detectors 140 and 142. Enclosure 122 attaches to linear bearing block 125 (shown in FIG. 7). Through this attachment, enclosure 122 moves in response to movement of upper timing belt 106. All of the sensors within enclosure 122 have associated with them a band pass filter 168 that improves the signal-to-noise ratio in their signal detection.

FIG. 9 also shows the scan area 170 for the preferred embodiment. The importance of this area will be understood more completely in connection with the explanation of the scanning system portion of this detailed description. FIG. 9, however, is useful for understanding the area of scanning available in the preferred embodiment. The scan area for the fixed distance between the enclosures 96 and 97 is the area across which the laser line-of-sight may be scanned while both view lines-ofsight 68 and 160 intersect. For example, at point 148 laser line-of-sight 62 intersects with view line-of-sight 68 and view line-of-sight 160. Hexagon 172 illustrates the possible scan area for a stationary or non-rotating object. Circle scan area 174 shows the possible scan area for a rotating object. Within scan area 170, lines 176 show that enclosure 97 can receive reflected light from the full range of sensor scan length 178. Similarly, lines 180 show that enclosure 96 may receive reflections from laser line 62 the full sensor scan length 182. As a result, the intersection of these lines which form the sides of hexagon 172 comprise the scan area for both enclosures 96 and 97 using a non-rotating target.

Figure 10:
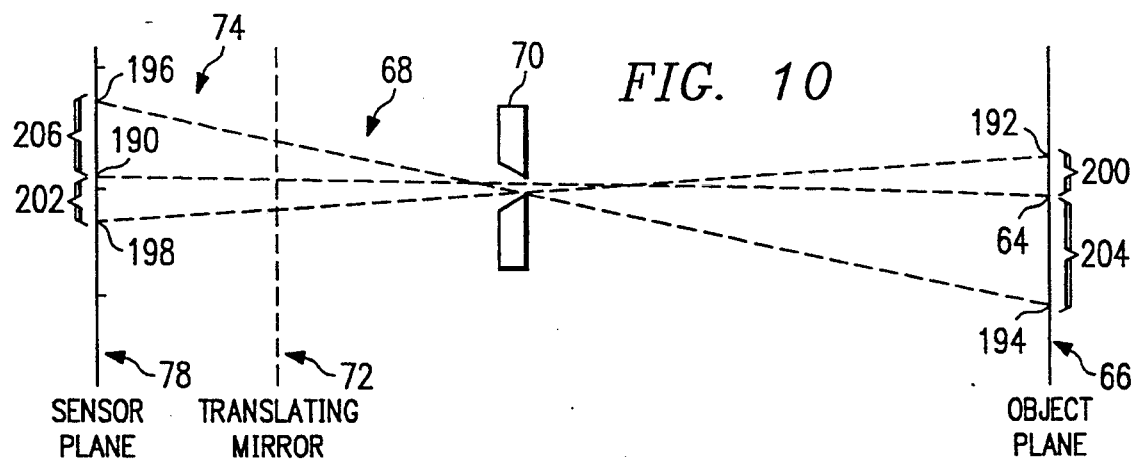
FIG. 10 provides a conceptual illustration of the pivoting aperture characteristic of the preferred embodiment of the present invention.
Figure 11:
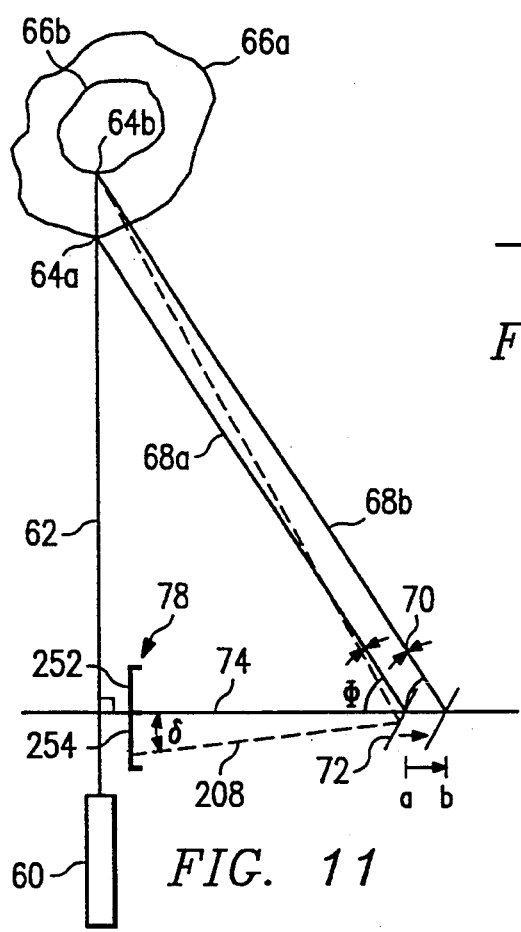
FIG. 11 illustrates active triangulation using photodiode centering in the preferred embodiment of the present invention.

Within the scan area, FIGS. 10 and 11 isolate and illustrate the importance of aperture 70 and reflecting mirror 72. The purpose of aperture 70 is to optically pivot light from surface point 64 on object 66 to the photodiode sensor 78. Once the light is properly pivoted to photodiode sensor 78, the purpose of translating mirror 72 is to locate the triangle side length with which the range length may be computed. FIGS. 10 and 11 conceptually show the light beam along view line-of-sight 68 and base line-of-sight 74. Referring to FIG. 10, if along view line-of-sight 68 light reflects from point 64, for example, it will pass through aperture 70 and go to point 190 on photodiode sensor 78. It is important to understand for the purposes of the FIG. 10 discussion that translating mirror 72 may be shown figuratively as the dashed line at which the beam is only optically bent. Therefore, view line-of-sight 68 and base line-of-sight 74 may, in this instance, be shown as a single continuous line. Also, for this discussion, object 66 may be simply viewed as a plane. If at the plane of object 66, instead of coming from point 64, light reflects from point 192, it passes through the optical pivot of aperture 70 to point 198. Likewise, from point 194 light will pass through aperture 70 to point 196 of the photodiode sensor 78.

A valuable property of the optical pivot that aperture 70 provides is that, because of the linearity of the light originating at the surface of object 66, the distance 200 between point 64 and 192 is a measurable factor of the distance 202 between points 190 and 198. Likewise, the distance 206 204 between points 64 and 194 is the same measurable factor of the distance between points 190 and 196. The measurable factor of the difference 200 and 202 in the distance 204 and 206 is a function of a position of aperture 70 between object 66 and photodiode sensor 78. This is a very attractive property of aperture 70, because a significant amount of a signal movement occurs at the sensor plane. By maintaining a long pivot length between sensor plane 78 and aperture 70, the system geometry amplifies the movement of the incident beam at the sensor plane 78.

FIG. 11 illustrates how the optical pivot that aperture 70 provides permits active triangulation. Consider, for example, objects 66a and 66b having respective surface points 64a and 64b. For the laser line-of-sight 62, the view line-of-sight for object 66a from surface point 64a is view line-of-sight 68a. Only this view line-of-sight 68a will result in a base line-of-sight 74 perpendicular to laser line-of-sight 62. This relationship is observable by what occurs if object 66b, having surface point 64b replaces object 66a. Surface point 64b is a measurable distance farther away from laser source 60 than is original surface point 64a of object 66a. In this instance, the light from point 64b that passes through the optical pivot of aperture 70 reflects from translating mirror 72, but will not result in a base line-of-sight 74 that is perpendicular to laser line-of-sight 62. Instead, the light line 208 that passes through aperture 70 and reflects from translating mirror 72 is displaced from the perpendicular by an angle δ.

Only when aperture 70 and translating mirror 72 move from point a to point b will the light reflecting from point 64b through aperture 70 and directed by translating mirror 72 align with the perpendicular base line-of-sight 74. This is because the angle Φ is fixed and the light optically pivots through aperture 70. The optical pivot of aperture 70 assures that only when the reflected light from translating mirror 72 causes a base line-of-sight perpendicular to laser line-of-sight 62 is it proper to make a range measurement of the point 64 of object 66.

As stated in connection with FIG. 10, the distance from which the light reflected from translating mirror 72 differs from the perpendicular line of base line-of-sight 74 is proportional to the change in distance along laser line-of-sight 62 caused by the different position on the surface point on the object. Once translating mirror 72 and aperture 70 mechanically move so that the reflecting light from surface point 64b on object 66b results in a line perpendicular to laser line-of-sight 62, the distance measurement along base line-of-sight 74 may be measured for triangulation of the laser line-of-sight 62 range. Thus, the preferred embodiment not only uses the triangulation methods of known systems, but also incorporates the attractive and elegant optical pivoting properties of aperture 70.

The width of aperture 70 determines geometric properties relating to the light reaching photodiode sensor 78. If light at surface point 64 has a smaller diameter than the aperture 70 slit width, then the light reaching photo-diode sensor 78 decreases with the square of the distance between laser source 60 and photodiode sensor 78. On the other hand, if the diameter of the surface point 64 is larger than the aperture 70 slit width (i.e., the usual case), then the intensity of light reaching photodiode sensor 78 decreases more linearly with the distance from surface point 64 to photodiode sensor 78. Placing collecting lens 144 before aperture 70 in the preferred embodiment partially compensates for this loss of signal intensity (see FIG. 9). Also, to avoid bending the light on the triangulation plane (i.e., the plane that laser line-of-sight 62, view line-of-sight 68, and base line-of-sight 74 form) a cylindrical lens may be used to bend the vertically divergent light (i.e., light located above and below the triangulation plane) back toward the triangulation plane.

Collecting light optics with a focal length longer than the maximum base line-of-sight length will effectively direct more light toward photodiode sensor 78 as the separation between laser source 60 and photodiode 78 increases. When the collecting lens 144 is designed so that the focal point is located behind photodiode sensor 78 the light incident on collecting lens 144 tends to bend more toward the photodiode sensor 78 as distance between surface point 64 and photodiode sensor 78 increases (i.e., the image point is located behind photodiode sensor 78 and moves toward photo-diode 78 as the separation distance increases). Bandpass filter 76 removes background noise to increase the signal-to-noise ratio of the light reflected from surface point 64.

Figure 12:
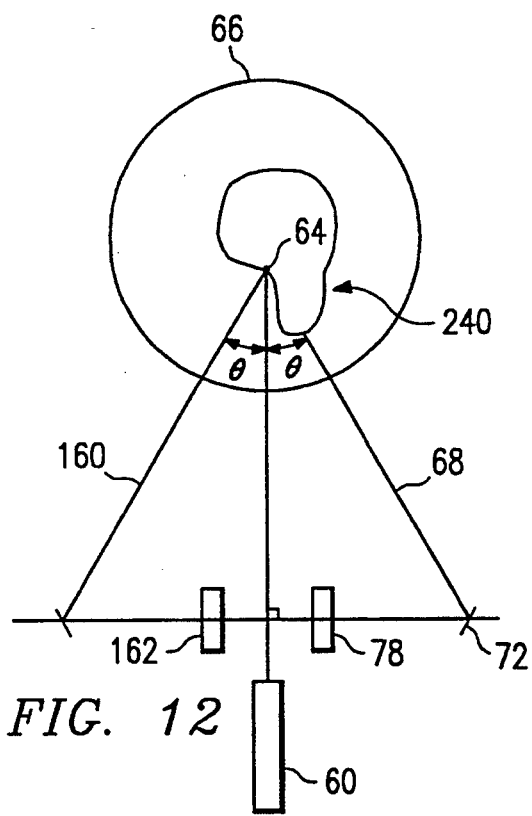
FIG. 12 illustrates the need for right and left ranging sensors in the preferred embodiment of the present invention.

An important aspect of the preferred embodiment is that it is necessary to have two photodiode sensors 78 and 162 on the right and left of laser line-of-sight 62. In the simplified schematic diagram of FIG. 11, for example, only the right-hand view line-of-sight 68 is shown. For the preferred embodiment, however, a left view line-of-sight is also used. Referring to FIG. 12, there is shown an object 66 that laser line-of-sight 62 from laser source 60 hits. If only the right-hand view line-of-sight 68 were available, the portion 240 of object 66 that obstructs point 64 will prohibit the measurement of point 64. Instead, the preferred embodiment uses view line-of-sight 160 to cause sensor 162 to receive digitized data from point 64. The use of view line-of-sight 160 overcomes the shadowing effect that portion 240 of object 66 creates. It is also worthy to note that there are an infinite number of off-axis views of that point that could be considered to form a cone-shape having an angle from point 64 so that the sides are an angle $\theta$ from the laser line-of-sight 62. At least, it is practical to consider, and well within the scope of the present invention to have a system with two additional sensors in line vertically with line-of-sight 62, but at an angle below and above line 62. In that case, a view line-of-sight having a vertical angle either above or below laser line-of-sight 62 may receive reflections from point 64.

Photodiode sensors 78 and 162 in the preferred embodiment comprise two photodiode elements. The following discussion of FIGS. 13 and 14 address the photodiode signal processing circuit for interpreting the output of the two photodiodes of the photodiode sensors. In the discussion that follows, the photodiode sensor of discussion will be photodiode sensor 78. The circuitry for photodiode sensor 162, however, is identical. Referring to FIG. 13, there is shown dual photodiode signal processing circuit 250 which takes the output of photodiode sensor 78. The output of photodiode sensor 78 comprises an output from photodiode 252 and photodiode 254. Output from each of the photodiodes 252 and 254 go to converters 256 and 258, respectively, of current-to-voltage conversion circuit 260. Voltage signals from current-to-voltage conversion circuit 260 goes to difference circuit 262 and summer circuit 264. That is, converter 256 output 266 and converter 258 output 268 each go to both difference circuit 262 and summer circuit 264. From differencer circuit 262, output 270, having the voltage level $V_A$ goes to comparator circuit 272. Comparator circuit 272 has a switched feedback signal associated with the reference input 274. The value of this reference is labeled $V_{A\ ref}$. Output from comparator circuit 272, having a value $V_o$, goes to conversion circuit 276. From conversion circuit 276, a single logic bit output 278 results as the output of photodiode signal processing circuit 250.

The value of the reference signal 274 to comparator circuit 272 is controlled by summer circuit 264. For this purpose, summer circuit 264 provides an output signal 280 having the value $V_\Sigma$ that goes to comparator circuit 282. Comparator circuit 282 outputs to diode and variable resistor circuit 284 which provides input 286 to analog switch circuit 288. Analog switch circuit 288 uses a source drain logic element 290 to generate the reference signal $V_{A\ ref}$. Thus, as a function of the comparator input 270 for the $V_A$ input and $V_{A\ ref}$ input 274, comparator circuit 272 controls the logic bit output 278.

Figure 14:
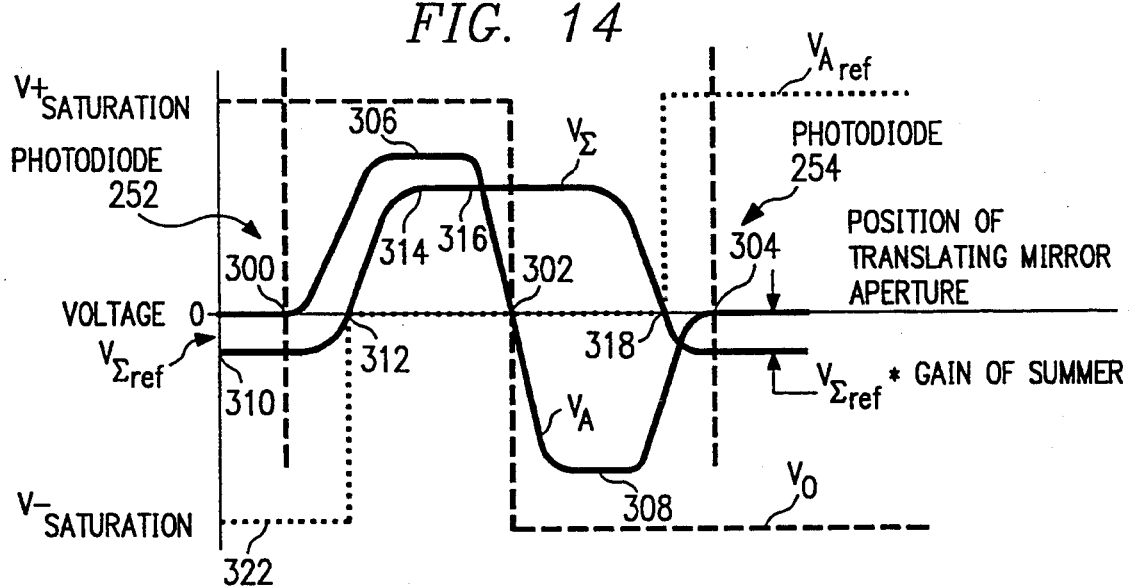

To understand the various outputs of photodiode signal processing circuit 250, FIG. 14 plots $V_A$, $V_\Sigma$, $V_{A\ ref}$, $V_{\Sigma ref}$ and $V_o$ as a function of mirror and aperture position. To understand the output that FIG. 14 describes, it is important to understand the meaning of the various voltage levels. $V_A$ is the output of differencer circuit 262. Thus, when photodiode 252 has a high output as a result of laser light reaching photodiode 252, $V_A$ takes on a high positive value. Conversely, when the laser light is on photodiode 254, $V_A$ has a large negative value. As laser light passes from photodiode 252 to photodiode 254, difference circuit 262 subtracts from the high positive value of voltage that photodiode that 252 causes and the negative voltage that photodiode 254 yields. As a result, when both photodiodes 252 and 254 receive laser light in equal amounts, the voltage $V_A$ has a zero value. As light leaves photodiode 252 and moves totally on photodiode 254, $V_a$ reaches its maximum negative value.

It is important to note two characteristics respecting the voltage $V_A$. First of all, $V_A$ may assume the value zero at three distinct points: point 300, point 302 and point 304 of FIG. 14. It is most beneficial to consider the meaning of each of these zero points by thinking of laser light passing from the outside of photodiode sensor 78 opposite photodiode 252, past photodiode 252 to photodiode 254, and then off of photodiode sensor 78 opposite photodiode 254. With this image in mind, it is appropriate to consider that when laser light first reaches photodiode 252, $V_A$ moves from a zero value and begins to assume a positive value to reach its maximum level of point 306. As light passes across photodiode 252 and part of the light moves to photodiode 254, the value of the voltage that photodiode 254 generates subtracts from the maximum positive value of $V_A$ until the zero point 302 occurs. Thereafter, the positive value of the voltage that photodiode 252 generates becomes less and less significant as the negative value of voltage from photodiode 254 dominates until the maximum negative value for $V_A$ at level 308 occurs. As laser light continues past photodiode 254 to the opposite side of photodiode 254, less and less light reaches photodiode 254. When less light reaches photodiode 254, less voltage results and the third zero value at 304 occurs.

The voltage $V_\Sigma$ is the output voltage from summer circuit 264. The voltage $V_\Sigma$ represents the sum of the outputs from photodiode 252 and 254. And, initially, $V_\Sigma$ assumes a negative value at 310 when laser light is off of photodiode sensor 78 on the side of photodiode 252. When light moves toward photodiode sensor 78 and begins to reach photodiode 252, the voltage $V_\Sigma$ becomes less negative until it crosses the zero level at point 312. As laser light becomes fully on photodiode 252, $V_\Sigma$ reaches the maximum value at point 314. Because $V_\Sigma$ is the sum of the outputs from photodiode 252 and 254, as laser light passes across photodiode 252 to reach 254, there will be no diminishing of the value of $V_\Sigma$, Instead, the value of $V_\Sigma$ represents the sum of the voltage that both photodiode 252 photodiode 254 produce. The voltage $V_\Sigma$ will remain at its maximum value until light passes across photodiode 254 and begins to pass off of photodiode sensor 78. When the value of the voltage that the light at photodiode 254 equals the value of the reference voltage $V_{\Sigma\ ref}$, $V_\Sigma$ equals 0 at point 318.

In response to the value of $V_\Sigma$ the reference signal $V_a$ $_{ref}$ assumes various values. As laser light passes on to photodiode sensor 78 from the photodiode 252 side, $V_\Sigma$ goes from a value of $V_{\Sigma\ ref}$ to 0. When $V_\Sigma$ equals 0 or ground, $V_{A\ ref}$ goes from the saturation negative voltage level at point 322 to ground at point 312. As long as $V_\Sigma$ remains positive, $V_{A\ ref}$ remains at ground 0. Once $V_\Sigma$ goes from its maximum level to ground at point 318, $V_A$ $_{ref}$ assumes the positive saturation value. It is the value of the reference voltage $V_{A\ ref}$ that determines the value of the output voltage $V_o$ from comparator circuit 272 (FIG. 13).

Note that when $V_{A\ ref}$ is at negative saturation voltage $V^-_{saturation}$, the value of $V_A$ has no effect on $V_0$. Likewise, when $V_{A\ ref}$ is at positive saturation $V^+_{saturation}$, the value of $V_A$ has no effect on the output voltage $V_0$. Only when $V_{A\ ref}$ is at ground does $V_A$ equalling zero affect the voltage output $V_0$. The voltage $V_{A\ ref}$ can only be zero when $V_\Sigma$ is greater than zero. $V_\Sigma$ can only be greater than zero when at least some light is on photodiode 252 and/or photodiode 254 and the amount of light on photodiode 252 or 254 produces a voltage exceeding the voltage $V_{\Sigma\ ref}$.

The result of the photodiode signal processing circuit 250 as described in FIGS. 13 and 14 is that only when light is on both photodiode 252 and 254, so that difference circuit 262 causes the voltages that photodiode 252 and 254 create to exactly cancel each other, will the voltage $V_0$ transition from positive saturation to negative, or vise-versa. Referring momentarily to FIG. 11 helps to illustrate the importance of the voltages from photodiodes 252 and 254 cancelling each other. Only when the laser light is on photodiodes 252 and 254 so that $V_o$ switches from either $V^+_{saturation}$ to $V^-_{saturation}$ at point 302 of FIG. 14 is base line-of-sight 74 perpendicular to laser line-of-sight 62. Because the angle Φ with base line-of-sight perpendicular to laser line of sight 62 is known, using trigonometry, it is possible to compute the range from laser source 60 to the surface point to obtain a digital measurement for that point.

2It is important to realize with respect to the voltage diagram of FIG. 14 that the various values that $V_a$, $V_\Sigma$, $V_{A\ ref}$, $V_{\Sigma\ ref}$, and $V_o$ assume are functions of the mirror and aperture position in the ranging system of the preferred embodiment. Thus, whether laser light passes across photodiode sensor 78 beginning at photodiode 252 and passing through to photodiode 254 or vice versa, the voltages will take on the relative values that FIG. 14 indicates. Thus, as $V_o$ transitions through point 302 from positive saturation to negative saturation, logic conversion circuit 276 outputs a digital bit at output 278 of FIG. 13. Likewise, as $V_o$ transitions from negative saturation to positive saturation, conversion circuit 276 also outputs a single logical bit at logic output 278 of FIG. 13.

The transition of the digital output bit at 278 from the dual photodiode signal processing circuit 250 indicates centering from which the 3-D object digitizing system of the preferred embodiment derives triangulation range data. The output bit from dual-photodiode signal processing circuit 250 is an indication of the direction in which the ranging system should move in order to obtain triangulation range data. In other words, the state of the digital bit from logic output 278 provides information concerning the side of dual photodiode 78 on which base line-of-sight 74 is located. For example, a digital HI from dual photodiode signal processing circuit 250 indicates that mirror 72 (FIG. 11) should move to the right, while a digital LO indicates that mirror 72 should move to the left.

The directional information that the state of the digital output encodes significantly reduces scan time in obtaining range data. This is because directional data reduces the amount of time that might be spent searching in the wrong direction for the light beam from surface point 64. For example, as long as $V_o$ is at $V^+_{saturation}$, dual photodiode signal processing circuit 250 outputs a HI output bit. With a HI output bit, the system knows that in order to transition from HI to LO, it is necessary to translate mirror 72 to the right. Similarly, as long as $V_o$ is at $V^-_{saturation}$, dual photodiode signal processing circuit 250 will output a single LO logic bit. This indicates that for a transition from LO to HI, it is necessary that mirror 72 and aperture 70 move to the left. With this directional information, significant scanning time is saved during the object digitization process.

In the preferred embodiment of the 3-D object digitizing system, the ranging system uses mechanical movement to mechanically triangulate the distance between laser source 60 and object 66. This is achieved by mechanically moving sensors 78 and 162 according to a well-defined method of scanning in response to measured distances. By using the simplified approach of mechanically moving photo-diode sensors 78 and 162, in response to measured distances, the preferred embodiment provides a significantly simplified and eloquent method of object digitizing relative to known CCD or other visual imaging systems that use a wide object image array and which must determine the right point on the sensor and the right sensor within the array from which to derive range data.

In practice, the time necessary to mechanically translate or move photo-diode sensors 78 and 162 represents only a very small portion of the object digitizing time. As a result, by using a much simpler optical sensor in the form of photo-diodes 78 and 162, it is possible to significantly simplify the digitization process. In essence, the 3-D object digitizing system of the preferred embodiment provides a simple optical pivot through an aperture with no imaging optics.

More particularly, the aperture and the geometry of the other components within the ranging system permit distance measurements and subsequent digitization of the surface points on any object. In the preferred embodiment, the probing angle between the laser line-of-sight 62 and view line-of-sight 68 is constant. This is a very attractive property for taking triangulation measurements. This is significantly simpler than the approach that conventional systems use which comprises a variable triangle and repeated calculations based on the variable triangle for imaging optics. In the preferred embodiment, the ratio of the distance from the sensor 78 to the aperture 70 to the distance from aperture to surface point 64 will remain constant throughout the triangulation measurements. This provides to the light that reaches photodiode sensor 78 very attractive and predictable properties. Because of this relationship, the width of the beam reaching photodiode sensor 78 and the movement of the light across photodiode sensor 78 are a constant factor of the change in distance along laser line-of-sight 62 that different surface points produce throughout an entire digitization process. Only the intensity of the light that reaches photodiode sensor 78 changes by a non-linear factor relative to the distance change in laser line-of-sight 62. To solve this problem, the preferred embodiment includes a collecting lens to increase the light intensity as it passes to photodiode sensor 78.

Another technical advantage of the present invention is that it assures that range measurements are recorded from the center of the laser beam that reaches point 64. Because it is very difficult to produce laser beams having highly collimated light, systems that provide high degrees of collimation are very expensive. With a highly collimated light beam, however, it is possible to focus on a unique point on the object to be digitized.

The object digitizing of the preferred embodiment takes advantage of the uniqueness that a highly collimated beam can provide, but uses a less columinated laser beam together with the mechanical measurement of the center of that beam to isolate and measure the center of the beam reaching object surface point 64. By only taking measurements when the laser beam is centered on dual photodiode sensor 78 and by amplifying the light with a collecting lens, it is possible to approximate the advantages of the highly collimated laser beam. Using dual photodiode sensor 78, the ranging system of the preferred embodiment creates an analog signal representative of the changes in distances along laser line-of-sight 62. By remaining in the analog domain through a much larger portion of the point digitization process, it is possible to more accurately locate the center of the illuminated surface point.

Another technical advantage of the object digitizing system of the preferred embodiment is that it makes possible tracking changes in the surface point as the laser line-of-sight moves across the object. As the system positions from one point to the next, the sensor continually knows which direction to move to center on the points. Additionally, the system of the preferred embodiment includes incidence detectors 140 and 142 (FIG. 8) that provide information as to whether or not the laser is incident on a surface. This provides the ranging system with information about whether or not movement of the aperture 78 and translating mirror 72 will yield a surface point measurement.

Another advantage of the incidence detectors of the preferred embodiment is that they make it possible to discriminate between light and dark surfaces on the object.

Another technical advantage of the present invention is that it provides a significant signal-to-noise ratio for the measured laser light on baseline-of-sight 74. Relative to known imaging systems that use CCD cameras or other video inputs, which are inherently noisy, the laser light of the preferred embodiment provides a drastically larger signal-to-noise ratio. As a result, while in known active triangulation systems it is difficult to be both accurate and resolute in making surface point measurements, the preferred embodiment overcomes this limitation. For example, in the preferred embodiment, as laser light passes photodiode sensor 78, as much as a ten volt signal change occurs with a noise level in the millivolt range. Consequently accuracy, resolution, and measurement repeatability are enhanced with the 3-D object digitizing system of the preferred embodiment.

OPERATION OF THE RANGING SYSTEM

Figure 15:
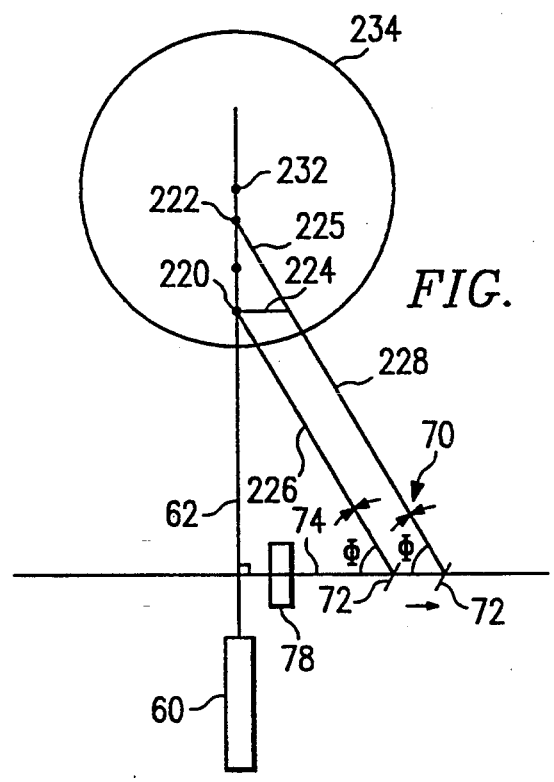
FIG. 15 provides a conceptual illustration of the orienting and initializing procedure of the preferred embodiment of the present invention.

Initial calibration of the ranging system of the preferred embodiment comprises a very accurate measurement of how much distance is traversed in one step of the motor. This measurement establishes a conversion factor for motor movement distances between translating mirror 72 and photodiode sensor 78. This calibration procedure typically is done only once at the manufacturing stage or during maintenance and need not be repeated for normal measurements. Upon setting up the 3-D object digitizing system of the preferred embodiment for taking range measurements, it is necessary to orient and initialize the system. FIG. 15 illustrates the orienting and initializing operation. It is important to understand when initializing and orienting the system that all that the digitizing system of the preferred embodiment must do is locate a reference point along the laser line-of-sight 62 and to determine a scale factor. This permits the measurement of two known points along the laser line-of-sight 62 that will permit calculating the angle necessary for the mirror to form the angle $\Phi$ between view line-of-sight 68 and base lines of sight 74. Note that it is not the angle of the mirror that is important, but the angle $\Phi$ between a view line-of-sight 68 and the base line-of-sight 74 that is to be determined. In the preferred embodiment, $\Phi$ takes the value of 60° so that the angle between laser line-of-sight 62 and view line-of-sight 68 is 30°. This optimizes the signal accuracy and resolution of the light reflecting from the object 66 as well as maximizes the possible penetration of measurements in deep object concavities.

For the system orienting and initialization procedure, it is necessary to find only two reference points along laser line-of-sight 62. With these reference points, it is possible to calculate the angle of translating mirror 72. In most instances, this measurement will be the same among different uses of the preferred embodiment and it may be appropriate to record and set the translating mirror 72 at a preset position without the orienting measurements. However, as the system continues over time to operate, the translating mirror 72 setting may no longer be accurate because of drift or other changes in the system. Referring to FIG. 15, base line-of-sight 74 intersects laser line-of-sight 62 at the perpendicular angle with photodiode sensor 78 located at base line of sight 74. The initialization procedure may begin by placing a known object, for example a block, at a first position 220 a distance from laser source 60. Then, a second object may be placed at point 222 a known distance axis from point 220. By translating aperture 70 and mirror 72 so that photodiode sensor 78 first receives laser light from view line-of-sight 226 and then translating aperture 70 and mirror 72 so that light from the second point 222 goes along view line-of-sight 228 to sensor 78, it is possible to characterize a triangle having base 224 and side 225. This is because line 226 and 228 are parallel. The translated distance of aperture 70 and mirror 72 along base line-of-sight 74 for receiving laser light first from point 220 and then point 222 is the same distance as triangle leg 224. The distance from point 220 to point 222 is known. Because base line-of-sight 74 and laser line-of-sight 62 are perpendicular, it is possible, using simple trigonometry, to determine the angle $\Phi$ at which photodiode sensor 78 receives reflections from points 220 and 222.

In the preferred embodiment of the present invention, the angle $\Phi$ may be computed automatically by the controlling microcomputer. In practice, the procedure of the preferred embodiment is to permanently fixture a reference block at the bottom of the work volume from which points 220 and 222 can be measured. The measurements are stored in a parameter file of the microcomputer that isolates the reference points on the laser line-of-sight 62 at which point the operator may identify point 232, for example, as the reference point which is the center of rotation of the rotating base 234. The object may rest during the digitization procedure, for example, at point 232. Taking the center of rotation of the platform 234 as the reference point on which the object rests, the operator may orient the system using the distance of points 220 and 222 from the center of rotation of base 234. For the preferred embodiment, points along the radius from the center of rotation 232 and closer to laser source 60 are considered positive. Points further away from laser source 60 and on the opposite side of center of rotation 232 are considered negative in value. Throughout the digitization operation, the point measurements are determined and stored as a positive or negative with respect to the reference point to characterize the surface of the 3-D object.

If the angle Φ is known or stored in a reference file, the initialization procedure of the preferred embodiment can begin by only knowing a single point, such as first point 220 and its actual distance from the reference point 232. With knowledge of the reference point 232 position and knowledge of the distance from point 220 and reference point 232, it is possible to reference all points of an object surface to these points and fully digitize the remainder of any object. The essential parameter, in any case, is a reference point, such as point 232, from which to measure the differences along laser line-of-sight 62 in order to initialize the 3-D object digitizing system.

It should be noted that the initialization process is not a calibration process. With initialization, there is no need to calibrate the laser source 60 or determine distances or provide any other type of calibration. Instead, the function of the initialization procedure is to establish a reference point or first point from which all other digital values can be determined.

Figure 16A:
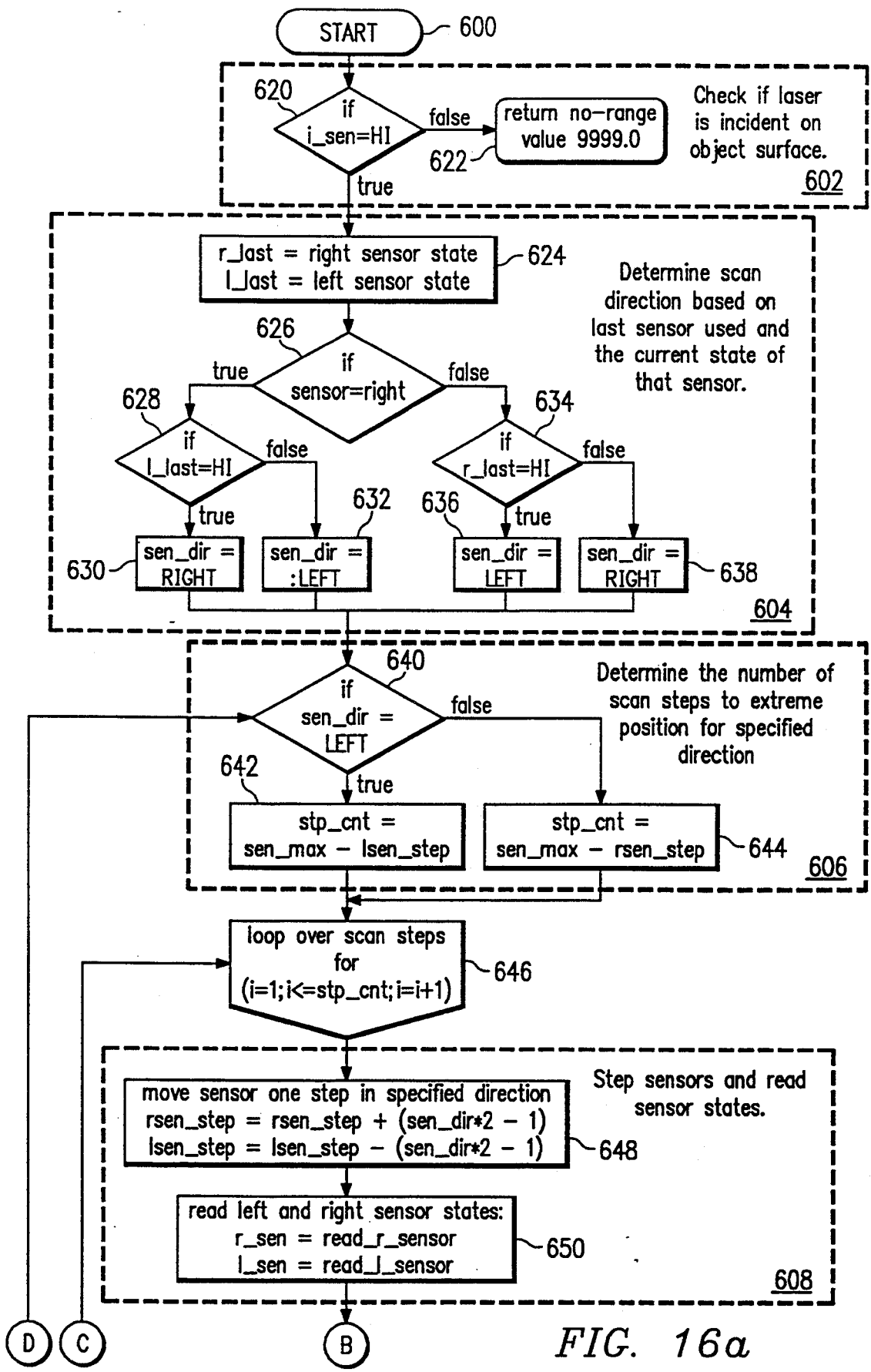
FIG. 16 provides a flow chart of the range measurement procedure of the preferred embodiment of the present invention.
Figure 16B:
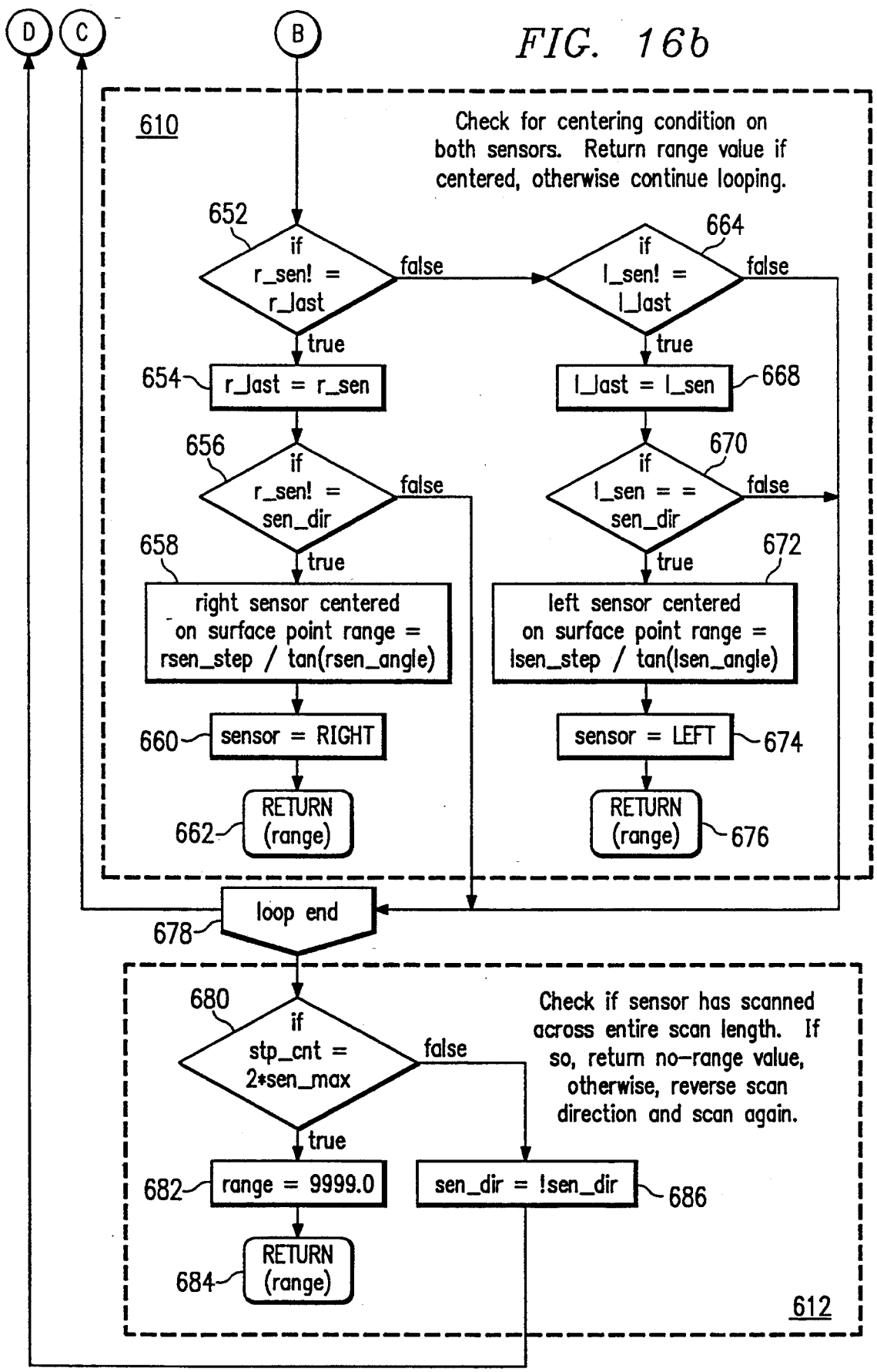

FIG. 16 provides a flow chart of the range measurement procedure for the ranging system of the preferred embodiment. Beginning at the start stop 600, the range measurement procedure comprises six major blocks of logic. Block 602 permits the ranging system to check if the laser is incident on the surface of the object to be digitized. The steps in block 604 determine the scan direction based on the last sensor used and the current state of that sensor. In block 606, the ranging system determines the number of scan steps to the extreme position for a specified direction. With this information, the ranging system in block 608 steps the sensors and reads the sensor states. Block 610 permits the ranging system to check for centering conditions on both sensors. If centering exists on both sensors a range value is returned. Otherwise, the ranging system will continue in a loop for a specified number of iterations. Block 612 provides steps necessary for the ranging system to check if the sensor has scanned across the entire scan length. If it has, the steps of block 612 return no range value. Otherwise, the ranging system reverses the scan direction and scans the object again.

To describe in more detail the steps of the logic flow for the ranging system, return to block 602 where the range measurement procedure checks if the laser is incident on the object surface. The discussion that follows will refer to the variables in the program for the range measurement procedure by stating the program variable names in parenthesis. The program for the preferred embodiment of the present invention is written in the programing language C and a printout of the range measurement procedure is provided at Appendix A to this detailed description.

At block 602 the preferred embodiment queries whether the incidence sensor state (i_sen) is HI. If not, the procedure returns a no-range value of 9999.0 at step 622.

If i_sen=HI, the program flow goes to step 624 of block 604 at which the previous right sensor state (r_last) is set to the right sensor state which may be HI or LO, and the previous left sensor state (l_last) is set to the left sensor state, which also may be either HI or LO. Next, at step 626, the range measurement procedure queries whether the sensor is on the right of the object. If so, at step 628 the procedure queries whether the previous left sensor state (l_last) equals HI. If so, at step 630 the sensor scan direction (sen_dir) is set to RIGHT. Otherwise, the sensor scan direction (sen_dir) is set to LEFT. If, at step 626, the procedure determines that the sensor is not to the right, then, at step 634, the procedure queries whether a previous right sensor state is HI. If so, then the sensor scan direction (sen_dir) is set to LEFT at step 636. Otherwise, the sensor scan direction (sen_dir) is set to RIGHT at step 638.

After setting the sensor scan direction (sen_dir), the procedure moves to block 606 to determine the number of scan steps to the extreme position for the specified direction. For this purpose, at step 640, the procedure queries whether the sensor scan direction (sen_dir) is LEFT. If so, the number of scan steps to be performed in a specified direction (stp_cnt) is set equal to the maximum step position of the sensor (sen_max) minus the step position of the left sensor (lsen_step). The maximum step position of the sensors is simply the maximum scan limit of the sensor forward and away from the laser line-of-sight. If, at step 640, the procedure determines that the sensor scan direction (sen_dir) is not LEFT, then at step 644 the number of scan steps to be performed in the specified direction (stp_cnt) is set to the maximum set position of sensors (sen_max) minus the step position of the right sensor (rsen_step). From block 606 (at either step 642 or 644) program flow goes to step 646, which begins a loop for a number of iterations equal to the number of scan steps to be performed in the specified direction (stp_cnt).

The next group of program steps takes place on block 608 within block 608 the function of stepping the sensors and reading the sensor states take place. In this function block, step 648 moves the sensor one step in the specified direction and then sets the step position of the right sensor (rsen_step) equal to the previous (rsen step) position plus the quantity two times the sensor scan (sen_dir) minus one, and the step position of the left sensor (lsen_step) equal to the previous (lsen_step) value minus the quantity two times the sensor direction (sen_dir) minus one. Next, at step 650, the procedure reads the left and right sensor states by equating the right sensor state (r_sen) to the present right sensor state, and the left sensor state (l_sen) to the present left sensor state.

Block 610 checks for the centering condition of both sensors 78 and 162 and returns the range value if they are centered. Otherwise, the procedure continues looping for the specified number of iterations. It does this by step 652 querying whether the right sensor state (r_sen) is not equal to ("!" means not) the previous right sensor state (r_last). If so, the procedure sets the previous right sensor state (r_last) to the right sensor state (r_sen) and then queries at step 656 whether the right sensor state (r_sen) is not equal to the sensor scan direction (sen_dir). If not, program flow goes to loop end step 678. If so, the right sensor is then centered on the surface point range with set equal to the step position of the right sensor (rsen_step) divided by the tangent of the right sensor triangulation angle (rsen_angle), at step 658. Next, at step 660, the sensor is set equal to RIGHT and at step 662, the range procedure returns a value of the range to the object.

If, at step 652, the right sensor state (r_sen) equals the previous right sensor state (r_last), then, at step 664, the procedure queries whether the left sensor state (l_sen)

does not equal the previous left sensor state (l_last). If so, at step 668, the previous left sensor state (l_last) is set equal to the left sensor state (l_sen) and at step 70 the procedure queries whether the left sensor state (l_sen) equals the sensor scan direction (sen_dir). If so, at step 672 the left sensor is centered on the surface point range to equal the step position of the left sensor (lsen_step) divided by the tangent of the left sensor triangulation angle (lsen_angle). Next, at step 674, the sensor is set to the left value and returns a range to the object at step 676. If, at step 664, the left sensor state (l_sen) equals the previous left sensor state (l_lest) or at step 670 the left sensor state (l_sen) equals the sensor scan direction (sen_dir), control returns to the loop end step 678 which returns program flow to the loop originating step 646 after incrementing the step index.

After the loop end step 678, program flow continues to block 612 to check if the sensor has scanned across the entire scan length of the object. If it has, then the no range value, 9999.0, will be returned. Otherwise, the reverse scan direction is implemented and scanning occurs again. This portion of the procedure begins at step 680, where the procedure queries whether the number of scan steps to be performed in the specified direction (step_cnt) equals two times the maximum step position of the sensor (sen_max). If so, at step 682, the procedure sets the range equal to 9999.0 and returns that value as the range at step 684. Otherwise, the procedure sets the sensor scan direction (sen_dir) to the opposite direction (!sen_dir). Next, program flow returns to block 606 where the procedure determines the number of scan steps to the extreme position for the specified direction and continues from step 640 as previously described.

SCANNING SYSTEM

Having explained the ranging system within the 3-D object digitizing system of the preferred embodiment, this portion of the description focuses on the scanning system. The scanning system of the preferred embodiment intelligently moves the ranging system about the object to be digitized. In the preferred embodiment, three degrees of freedom (DOFs) are possible. In an ideal object digitizing system, four forms of relative motion between an object and laser line-of-sight 62 are necessary to illuminate a point on any exposed 3-D object surface. The four forms of relative motion are two translational and two rotational DOFs between the laser and the object. Because of the complexity of providing four DOFs, the 3-dimensional object digitizing system of the preferred embodiment provides two translational DOFs and one rotational DOF. In essence, laser source 60 may be translated vertically and horizontally, while object 66 may be rotated about a vertical axis. By not providing the fourth DOF (i.e., rotation of object 66 about a horizontal axis) the 3-dimensional object digitizing system of the preferred embodiment cannot measure points along vertically facing surfaces. For most applications, however, the practicality of using a four DOF digitizer is questionable due to mechanical, operational, and data processing limitations. The fourth DOF may, however, be partially realized by digitizing the same 3-D object multiple times in different orientations. This approach requires that the multiple data sets be "merged" to form a single mesh surface.

By using different combinations of its three DOFs, the 3-dimensional object digitizing system of the preferred embodiment may perform three types of 3-dimensional scanning procedures:

(1) Two DOF scanning using two translational DOFs;

(2) Two DOF scanning using translational DOF and rotational DOF.

(3) Three DOF scanning using two translational DOFs and one rotational DOF.

Each of these three scanning options is useful for different types of objects. Flat objects are best digitized using two translational DOFs, while convex objects are best digitized for using both translation and rotation. Three DOF scanning offers a very attractive method for digitizing complex objects with non-axial geometry, multiple contours and concavities.

Figure 17:
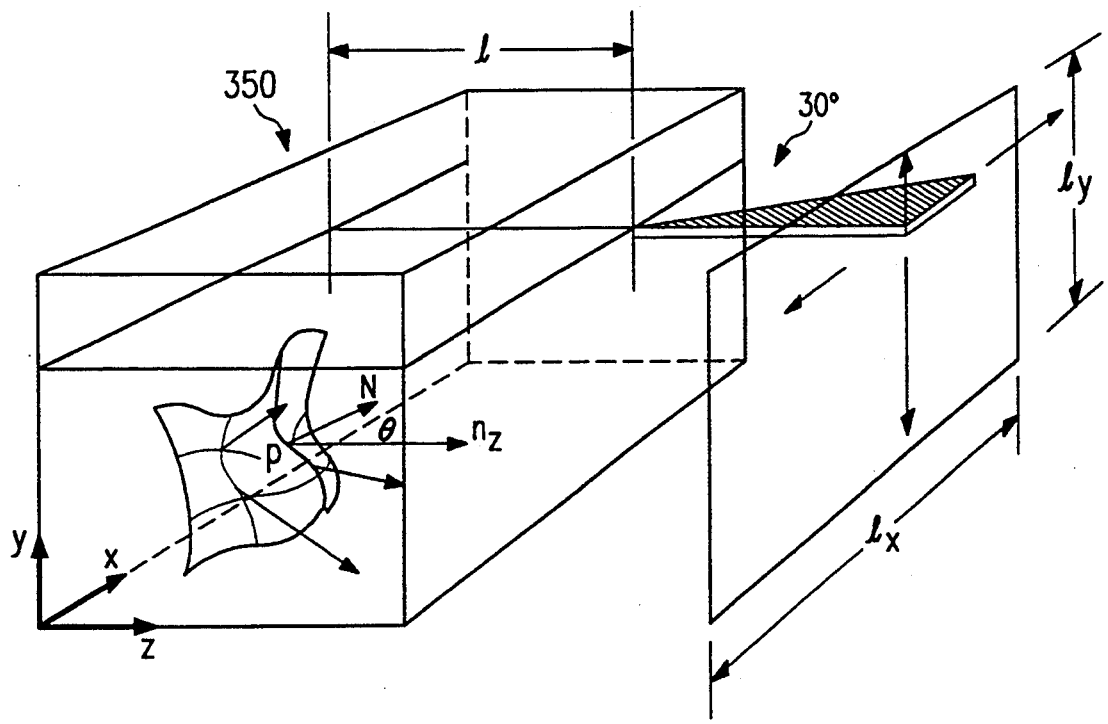
FIG. 17 illustrates a two translational degree of freedom scanning work volume.

Probably the simplest scanning procedure useful with the 3-D object digitizing system of the preferred embodiment employs two translations of the ranging system. FIG. 17 illustrates work space 350 that two translations produce at the active ranging distance l. With the active ranging distance l, a maximum vertical translation $l_y$ and a maximum horizontal translation $l_x$ exists. FIG. 17 demonstrates that in order to maintain an acceptable incidence angle Θ, the surface normal N at any point p must not depart significantly from the positive Z direction $n_z$. As a result, two translational DOF scanning usually should be used only to measure relatively flat surfaces.

Figure 18A:
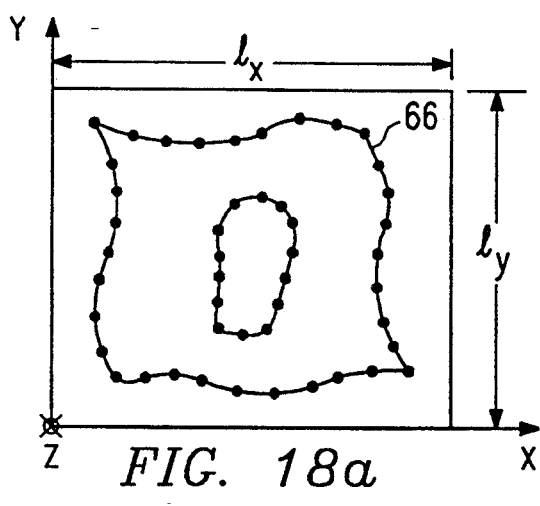
FIGS. 18a–18f illustrate various scanning procedures applicable to two translational degree of freedom scanning.
Figure 18B:
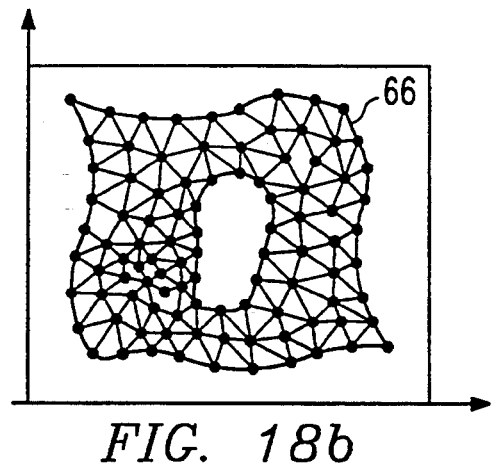

Once the operator decides to use two translational DOF scanning for a given application, it is necessary to decide whether a systematic scanning procedure, an adaptive scanning procedure or a combination of both systematic and adaptive scanning will optimize the digitization process. Referring to FIGS. 18a–18f there is shown a variety of ways in which to digitize a simple surface. FIG. 18a illustrates the data that a fully adaptive procedure that follows surface of object 66 provides. The points in FIG. 18b may be acquired with a fully adaptive procedure designed to provide higher sample densities in regions of rapid surface curvature and along edges.

Figure 18C:
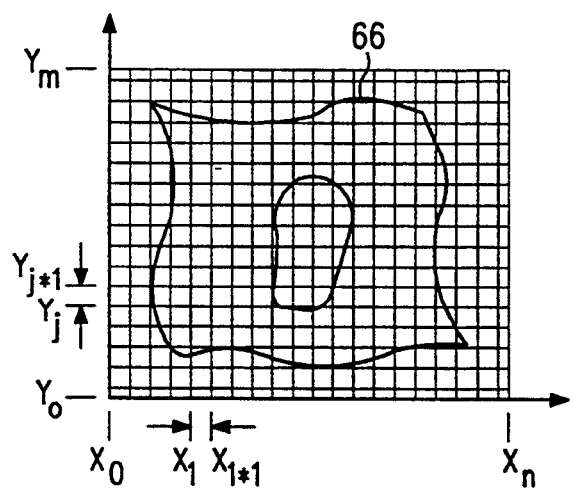
Figure 18D:
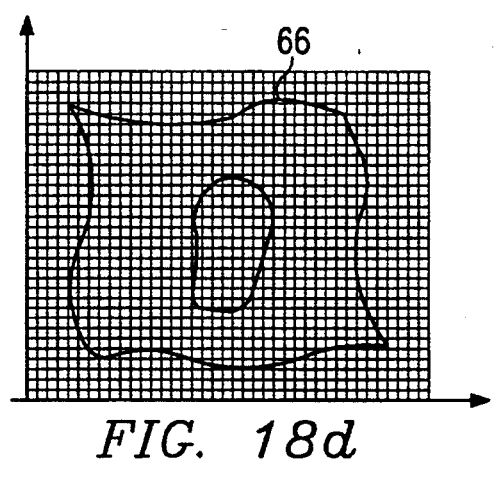
Figure 18E:
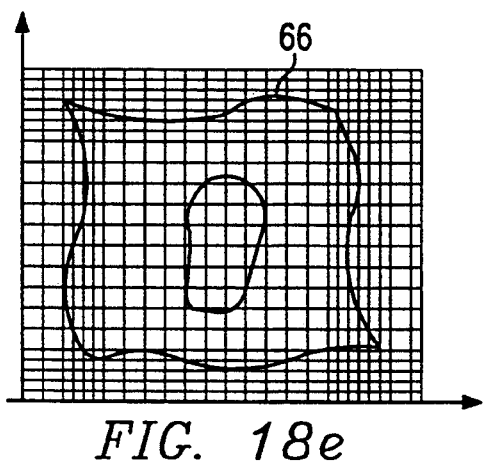
Figure 18F:
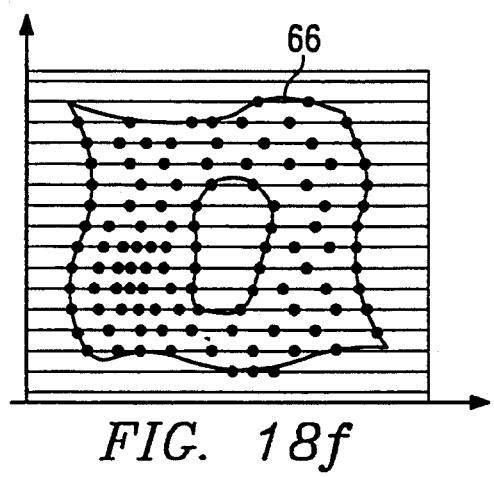

FIGS. 18c, 18d and 18e illustrate the type of data that the object digitizing system of the preferred embodiment may acquire along an X-Y grid. In these instances, improved edge resolution is obtainable by simply specifying a denser sample grid at various regions as FIG. 18e shows. That is, FIG. 18e demonstrates that even systematic scanning procedures may be designed to provide varying sample densities along different portions of the surface of object 66. A semi-adaptive scanning procedure may also be used which combines systematic scanning with adaptive scanning. FIG. 18f shows the results of a semi-adaptive scanning procedure.

Returning to FIG. 18b, it is apparent that the surface mesh that adaptive scanning produces is attractive, because it is efficient. An adaptive mesh is optimal to provide more points in high frequency and few points in regions where high sample density is unnecessary. The other data produced by adaptive scanning procedures are attractive. In practice, it is generally more practical to employ fully systematic procedures when scanning with only two DOFs. This is true, first of all, because the grid topology of systematic data is provided implicitly while the grid topology of adaptive data, by some method, must be explicitly specified and recorded. Moreover, systematic data from a high density grid may be adapted closer to produce a surface mesh that is very similar in quality to that which adaptive scanning procedures produced.

Though adaptive scanning methods are useful for some applications using two translational DOFs, systematic scanning procedures are generally more useful, because they are easy to perform and provide structured data that can be filtered to provide an optimal data subset. Another advantage of using high-frequency, systematic scanning procedures with two translational DOFs, is that when the user decides that more data is necessary, it is generally easier to refilter a set of data than to redigitize an object. Systematic sampling procedures make this possible. Thus, when using two translational DOFs, systematic scanning is the preferred method for using the ranging system of the preferred embodiment.

Figure 19:
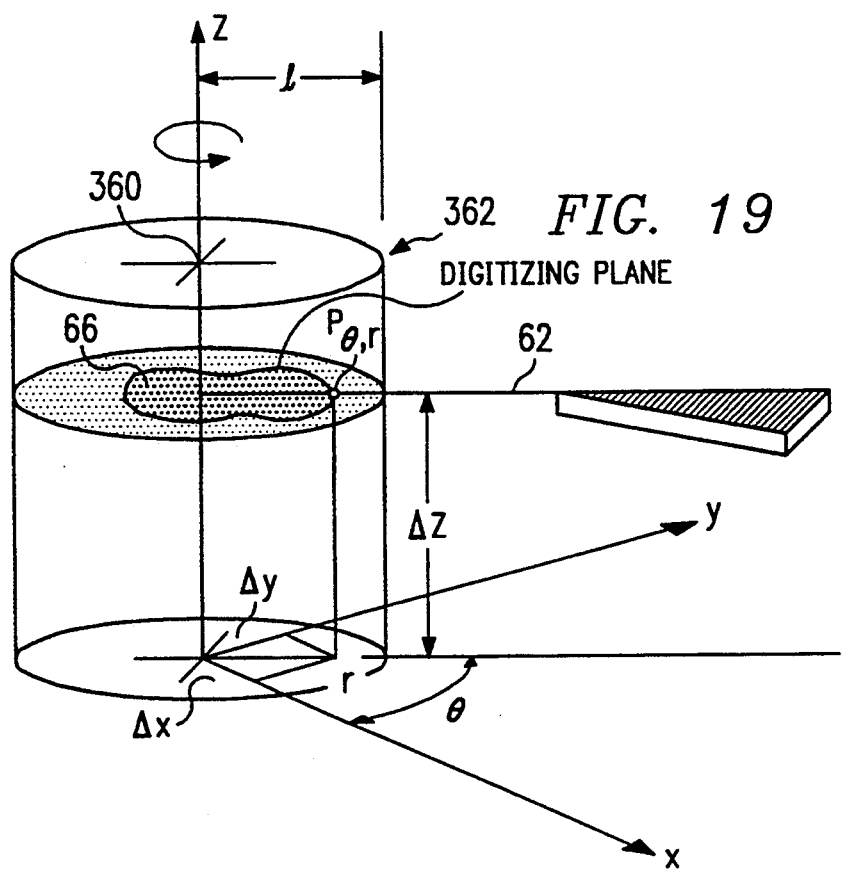
FIG. 19 illustrates the work volume for a one rotational and one translational degree of freedom scanning system.

It is also possible to use one translation DOF and one rotational DOF. FIG. 19 illustrates that by positioning laser line-of-sight 62 to pass orthogonally through the center of rotation 360 a set of radial measurements may be obtained by rotating object 66 and vertically translating the ranging system. For this type of scanning procedure, the 3-D object digitizing system of the preferred embodiment provides a cylindrical work space 362. This scanning configuration is useful for convexed shapes, because acceptable incidence angles are possible only at locations where the surface nodal does not depart significantly from the radial direction. When choosing between systematic versus adaptive scanning procedures, the same reasoning that applies in the case of two translational DOF scanning is applicable one rotational and one translation DOF scanning. A systematic scanning procedure produces a data grid (with complete topology and filtering capabilities) by incrementally rotating the object while incrementally translating the ranging system. Adaptive scanning procedures are useful, in this instances, for relative specialized applications.

Several important properties relate to rotational contour sampling with one translation of the DOF and one rotational DOF. First of all, referring to FIG. 19, points with a surface tangent that passes through or near center of rotation 360 cannot be measured. Secondly, negative distances may be measured, because of the active range of the ranging system extends past the center of rotation 360. Furthermore, closer spacing between measurements occurs along contours that are closer to the center of rotation. Also, off-center objects are sampled during two portions of a complete rotation. This causes partial loss of topology and partial loss of the contour on two sides where large incidences angles make measurement impossible. Finally, one translation DOF and one rotational DOF cannot effectively measure concave surfaces.

One translational and one rotational DOF scanning procedures are attractive, because they are easy to perform and produce data that is easy to work with. Unfortunately, the type of object that this method of scanning produces is limited.

FIGS. 20a–20c illustrates the work volume available for digitization using three DOFs. The three DOFs include rotation of the object and translation of the laser line in the vertical and horizontal planes. The work volume is cylindrical and is limited by either the active length l or the maximum horizontal travel $l_h$ of the ranging system. Referring to FIG. 20a rotation within the three DOF work volume is about the vertical axis 370. This creates a cylindrical work volume having a radius r and a height limited by the vertical translation limit $l_z$ of the laser line-of-sight 62. The laser horizontal translation limit is $l_h$, when $l_h$ exceeds l.

There are two significant advantages in using a third DOF. First of all, the surface normal at any given point is limited only by the requirement that it not depart significantly from the horizontal. Secondly, using a third DOF the system of the preferred embodiment may measure each individual point from a variety of perspectives. That is, the laser line-of-sight 62 can illuminate a single surface point from a variety of different locations.

Figure 21:
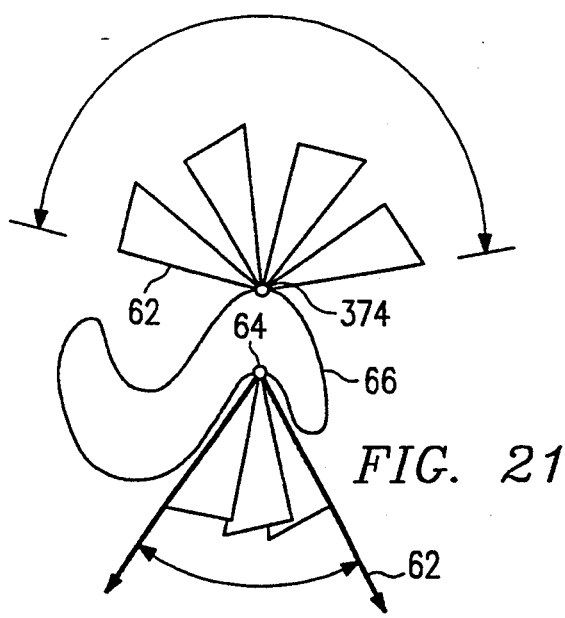
FIG. 21 and 22a–22e illustrate various characteristics of systematic and adaptive scanning using a three degree of freedom work volume.

FIG. 21 shows, for example, that object 66 has a first surface point 64 and a second surface point 374. For this concavity, using three DOFs permits not only many measurement orientations along the convex surface having point 374. Multiple probing orientations also permit limited measurement orientations for the concave surface having point 64.

Figure 22A:
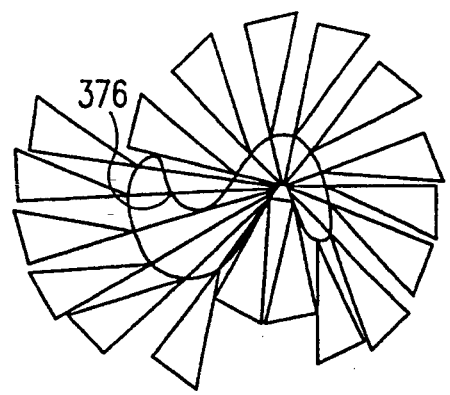
Figure 22B:
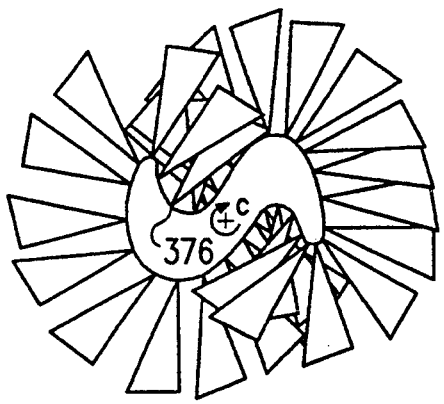
Figure 22C:
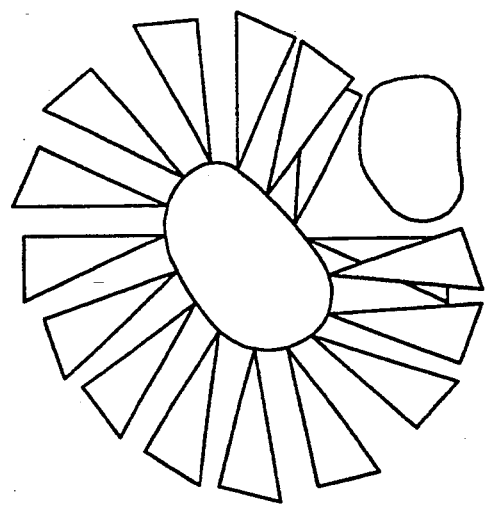

FIGS. 22a–22c demonstrate how complex contours may be better sampled along a horizontal plane by both rotating the object and translating the ranging system. Referring to FIGS. 22a and 22b, it is easy to see that with only rotation (FIG. 22a), very poor surface data is obtainable. In fact, for the simple rotation that FIG. 22a shows, almost a complete region, such as the concave region 376 will not be measured. FIG. 22b on the other hand, illustrates that adaptive scanning with rotation and translation produces significantly more accurate measurement data and obtains good measurement data for concavities. In particular, for the same shape as appeared in FIG. 22a, the adaptive scan with rotation and translation used for measuring in FIG. 22b illustrates that region 376 is appropriately sampled for digitizing data. Moreover, FIG. 22c shows that with adaptive scanning it is possible to use rotation and translation to obtain data points for multiple contours of a single object.

An efficient three DOF procedure for sampling contours along a horizontal cross section requires adaptive feedback control. The direction and rate of curvature along a contour are computed using previously acquired points to help predict the location and surface normal of a target point (i.e., the next point to be measured). In this way, the object is rotated and the ranging system is translated to provide an optimal measurement perspective for each consecutive target point as the system intelligently tracks a contour. For convex surfaces, the optimal measurement prospective is obtained with a zero incidence angle between the laser beam and the surface normal.

Figure 22D:
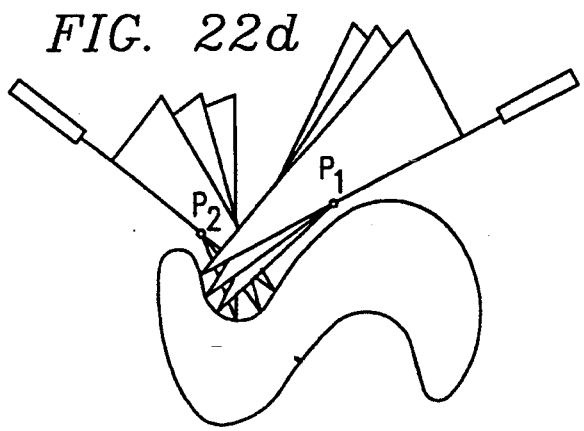

FIG. 22d demonstrates that for concave surfaces, optimal measurement prospectives are obtained when laser line-of-sight 62 closely pivots about the outer edges of the concavity. Orientations of this type will typically produce non-zero incidence angles. As FIG. 22b shows, improved and very useful results arise from adaptively moving along a contour. By measuring consecutive points, the system of the present invention effectively acquires complete topology information (i.e., points are connected in the same order in which they are measured). When multiple contours exist, the system scans each contour separately by attempting to complete a contour by pivoting around any other obstructing contours.

Although two DOFs may scan adaptively within a horizontal plane, the third DOF typically is useful to systematically position the ranging system at vertically displaced planes. For this reason, three DOF scanning may be considered as "semi-adaptive." It is important to recognize that adaptive scanning along planar cross-sections provides complete contour topology in the horizontal direction. This is a great advantage, by blindly moving to vertically displaced planes, semi-adaptive scanning provides no vertical topology between neighboring cross-sections. In other words, semi-adaptive scanning provides no information to establish how points in one plane or contour connect to points in a corresponding vertically displaced planar contour. As a result, a procedure for vertical topology generation must be employed to obtain a valid surface mesh from semi-adaptive data.

Figure 22E:
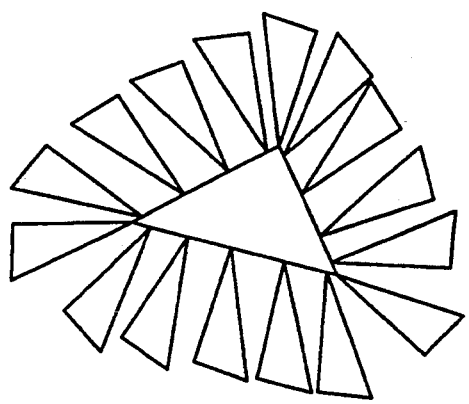

For semi-adaptive scanning to flexibly discriminate between rapid and slow rates of surface curvature, the adaptive scanning procedure may use a filtering mechanism. FIG. 22e demonstrates that by using the local rate of surface curvature to adjust spacing between consecutive measurements, a relatively small number of measurements are necessary to define a contour containing sharp corners and slow curving sides. Without a filtering mechanism, a contour of this type must be sampled frequently to ensure that the digitizing system adequately resolves the sharp corners. If the system does not adequately resolve sharp corners, significantly more time will be necessary and, in the simple triangular shape of FIG. 22e, will produce an over-abundant amount of data along the triangular sides.

A competing disadvantage exists in using an adaptive filtering mechanism along planar cross-sections when performing a semi-adaptive scanning procedure. When systematically stepping to consecutive planes, no filtering mechanism is applied in the vertical direction. This produces a non-homogeneous surface mesh composed of long skinny polygons. This problem can be resolved by employing a vertical filter either during or after the scanning procedure. When scanning, a fuller adaptive procedure is fast and concise, but it is difficult to implement and the resulting data must explicitly specify topology. After scanning, a vertical data filter must be applied to produce a homogenous surface mesh which will also require explicit topology information.

Figure 23:
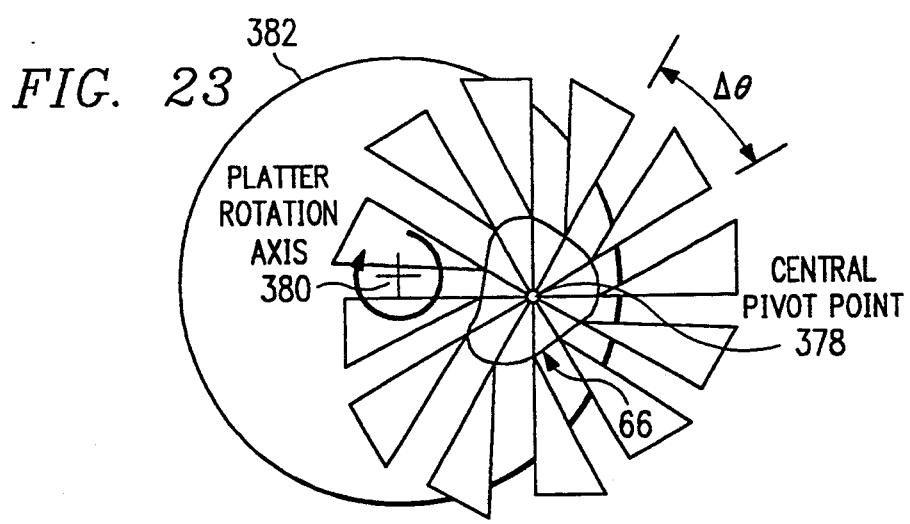
FIG. 23 illustrates the results of systematic scanning using a three degree of freedom work volume.

FIG. 23 demonstrates that, by constraining laser line-of-sight to pivot through the central pivot point 378, a fully systematic scanning procedure that utilizes both rotation and translation may be performed to measure the planar contours of off-axis objects. This type of scanning procedure, which is a fully systematic three DOF scanning, is useful for long, curved objects which cannot be completely centered along the rotational axis 380 of platter 382. If the contour of object 66 remains mostly convex along neighboring cross-sections, then off-axis objects of this type are most appropriately digitized with the fully systematic DOF scanning procedure. Notice, however, that systematic three DOF scanning procedures are not useful when multiple contours are present in a single cross-section.

The advantages of using a systematic, versus adaptive, scanning procedure include simplified control and improved reliability of the scanning process and greatly simplified data processing requirements. Data processing is simplified, because like systematic two DOF data, the data that systematic three DOF scanning produces is a rectangular grid containing complete topology on which to employ simple adaptive filtering mechanisms. In comparison to the axial center of rotation characteristic of fully systematic two-DOF, fully systematic three DOF data possesses a curved "backbone" which adaptively follows the centroid at consecutive cross-sections along the object.

Having described the advantages of the various degrees of freedoms, the system of the preferred embodiment utilizes these advantages in an adaptive scanning algorithm for control that permits optimal surface point digitization as a function of the surface contour. The discussion that follows describes the adaptive scanning algorithm of the preferred embodiment of the present invention.

The adaptive scanning algorithm of the preferred embodiment possesses two modes: a normalizing mode and a pivoting mode. In the normalizing mode laser line-of-sight 62 remains normal to the surface of the object. In pivoting mode, the laser pivots around an obstruction to reach a surface point on the object. As explained above, the outer edge of a concavity of an object can be considered to be an obstruction to obtaining surface point measurements for the surface within the concavity.

The discussion that follows describes the adaptive scanning procedure of the preferred embodiment. The scanning algorithm of the present invention provides an automated system for intelligently identifying the optimal orientation between the object and the laser for the surface point measurement. For the preferred embodiment, it is optimal that photodiode sensors see the surface point being digitized from approximately the same angle to the normal. For this to occur, it is most desirable that laser line-of-sight 62 reach the object at the normal angle. For some contours, such as deep concavities or in the presence of obstructions this is not possible. However, whenever possible given the contour of the system, the scanning algorithm seeks to orient the object and the laser to achieve a normal incidence angle. Thus, the purpose of the scanning algorithm is to adaptively control the scanning of an object by the 3-D digitizing system of the preferred embodiment by shifting between normalizing mode and pivoting mode to collect surface point data.

Figure 24:
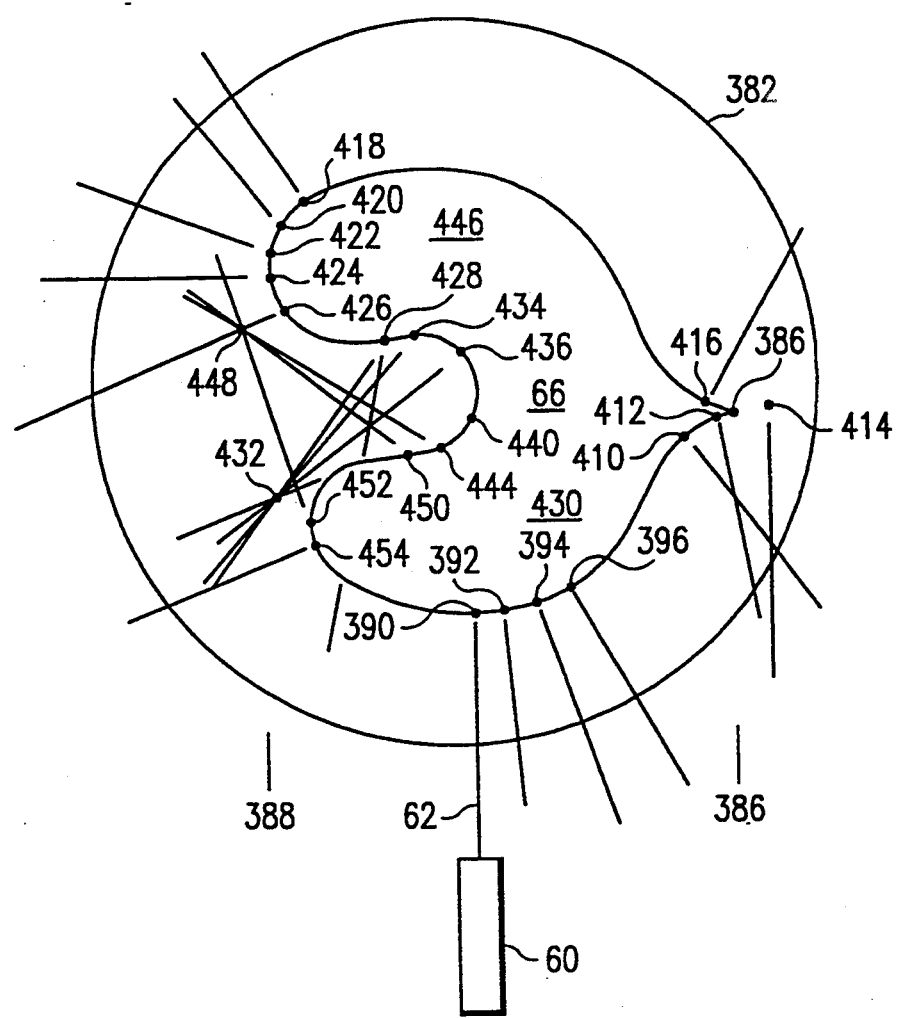
FIG. 24 illustrates the adaptive scanning method of the preferred embodiment of the present invention.

Referring to FIG. 24, consider object 66 on platter 382 for which digitization using laser source 60 as desired. Platter 382 may rotate in either a clockwise or counter-clockwise direction and laser source 60 may translate to the right or to the left in the horizontal plane and up and down in the vertical plane. For the system of the preferred embodiment, the scanning algorithm begins, for example, by laser 60 passing from the right to the left of the volume. Using incidence detectors 140 and 142 (not shown), laser 60, as it passes from the right to the left, first determines at point 386 that it is hitting an object. The incidence detector will continue to report to the ranging system that laser source 60 is hitting an object until the line 388 is reached. Once the span between 386 and 388 is measured by the ranging system, the scanning algorithm chooses, for example, the midpoint 390 as the beginning point from which to take measurements. This beginning or originating step for establishing a measurement beginning point may be performed by any number of ways for selecting an arbitrary beginning point. This, however, is the method used for the preferred embodiment.

At point 390, for example, the first measurement is taken by the object digitizing system. At this point, it is not possible to determine any directional characteristics of the object contour. In other words, it is not possible to estimate the direction or curvature of the surface from this first measured point 390. From point 390, the adaptive scanning algorithm moves a predetermined distance to obtain a second measured point 392.

With the measurement of point 392 comes a significant amount of information. The information includes a rough estimate of the local surface direction. The slope of the line connecting points 390 and 392 and, consequently, the ability to estimate where the third point 394 should be on object 66 can be better determined now. The ability to derive this information only requires the use of simple trigonometric relationships which are implemented in the scanning algorithm of the preferred embodiment. The scanning algorithm, therefore, positions platter 382 and laser source 60 to take the third point 394 at an optimal angle as close to normal as possible. This measurement estimate may not be totally accurate, but it will be within a predetermined tolerance range. Therefore, if the actual measurement of point 394 is within the tolerance range of the scanning algorithm, the algorithm keeps that point that is measured and then positions to take a fourth point 396 that is distant from the actual mesh point 394 by the predetermined spacing. With these three points 390, 392, and 394, the scanning algorithm can determine local surface curvature of object 66. As a result, the estimate for the point 396 location is much more accurate than the estimate that points 390 and 392 provided for point 394. In fact, for all subsequent measurements only the previous three points are necessary to determine a very accurate prediction of the next point. That, of course, does not relate to a surface discontinuity such as a sharp edge.

When a sharp edge arises, the normalizing mode of the algorithm makes adjustments in the point prediction to compensate for the fact that an actual measurement falls outside of the tolerance range of the expected point measurement. For example, consider that points continue to be taken along object 66 to point 386. At point 386, the previously measured points may have been point 410 and 412. Based on the curvature information that points 410, 412 and 386 provide, the normalizing mode expects the next point to be at point 414. This is not the case, however. Upon taking the measurement at point 414, no data will return to the ranging system. This is because the laser line will continue out into free space and no object point will be recorded. With this information, the adaptive scanning algorithm must make adjustments.

Using the fact that no range data returns for point 414, the adaptive scanning algorithm uses the information to rotate platter 382 and translate laser source 60 to take the next surface point measurement at point 416. The algorithm does this by estimating the angle to be 90° or more between points 386 and point 416 and then it makes a measurement. These measurements will continue to be attempted until the laser line rotates around the edge and the actual range measurement falls within the acceptable tolerance of the estimated range measurement based on the last three measurements. For the preferred embodiment, this routine has proven successful to the extent of causing the platter 382 and laser source 60 to translate up around a completely thin flat surface such as a piece of paper. In the normalizing mode, the steps will continue until either the surface is completely digitized or an obstruction occurs causing the adaptive scanning algorithm to shift to the pivoting mode.

To understand the shifting of the algorithm from the normalizing mode to the pivoting mode, consider that the digitizing system continues to sample points along the surface object 66 beginning, for discussion purposes, at point 418. At point 418, the normalizing mode continues to work satisfactorily and measurements continue to points 420, 422, 424, and 426 until at point 428 the system seeks to take a measurement at which point portion 430 of object 66 obstructs the line-of-sight of the laser. In this condition, the point that the ranging system measures will be both out of tolerance and closer to the laser than the expected point measurement 428 by a significant amount. Moreover, the adaptive scanning algorithm knows that the obstruction came in from the right, based on the previous measurements for points 424 and 426. From this information, the adaptive scanning algorithm moves to set a pivot point, for example, point 432 a predetermined distance from the obstruction 430. Then, the system calculates the necessary rotation of platter 382 and translation of laser source 60 that will cause the laser line-of-sight to pass through pivot point 432 to reach the expected location of point 428.

Once the measurement is taken at point 428 in this way, the adaptive scanning algorithm remains in the pivoting mode to take subsequent measurements of points 434, point 436, etc., but all through the pivot point 432. This will continue until the point measurement is attempted, for example, at point 440, where obstruction 430 again prohibits measurement. This situation is only a repeat of the earlier situation that caused the scanning algorithm to establish pivot point 432. At this point, a further pivot point may be attempted or the algorithm may shift to the normalizing mode. This will occur when the angle between the laser line-of-sight and the tangent to the surface is below a predetermined level, for example, 30° in the preferred embodiment. When the angle between the laser line-of-sight and the tangent to the measured point falls below 30°, the adaptive scanning algorithm of the preferred embodiment moves the laser line toward the surface normal by either reversing the pivot direction to locate a pivot point on an opposite side of the obstruction or shifting away from the obstruction by returning to the normalizing mode.

In this case the shifting from pivoting mode to normalizing mode occurs when, by shifting the laser toward the surface normal, the laser moves away from the obstruction 430. The scanning algorithm knows where the last measured point is and seeks to position platter 382 and laser source 60 so that laser line-of-sight 62 is normal to the slope of the surface at the next point to be measured. If the next point to be measured is point 444, for instance portion 446 of object 66 obstructs the laser line-of-sight and prevents normalizing mode measurement. In positioning for establishing the normal to point 444, the adaptive scanning algorithm knows that a new obstruction came in from the left this time. Since the obstruction came in from the left, it is possible to establish pivot point 448 to the right, from which measurements can be taken in the pivoting mode. Thus, the adaptive scanning algorithm shifts to the pivoting mode and continues to take points 444, 446, etc. until the condition exists that the angle between the tangent and laser line-of-sight falls below the threshold of 30° in the preferred embodiment. This may occur, for example, at point 452. At that point, the adaptive scanning algorithm shifts back to the normalizing mode to establish a laser line-of-sight 62 normal angle to the surface at point 454 to take a measurement. From that point the scanning algorithm will remain in the normalizing mode to take range measurements until it returns to beginning point 390. This completes the scanning of a plane of the object that FIG. 24 shows.

There are special cases for which the scanning algorithm will not produce a complete digitized record of the object surface. In particular, when concavities are so deep that the 30° angle between the laser line-of-sight and the view line-of-sight cannot reach into the concavity to make a measurement, the system will produce incomplete data. This causes a stopping condition in the adaptive scanning algorithm. If a stopping condition of this nature arises, the scanning algorithm will return to the point at which initial measurements begin and proceed in an opposite direction along the surface until it reaches the concavity from the opposite side of which the stopping condition will again occur. The results of this use of the adaptive scanning algorithm is a less than complete digitization of the object surface. The incompleteness is that portion of the deep concavity that the laser line-of-sight was not able to measure because of the angle limitation.

An essential characteristic of the scanning algorithm of the preferred embodiment is the feedback system it employs to measure and interpret the data points it receives. In measuring the normal direction for a surface, the system must compensate for inaccuracies in the previously measured point. If the spacing between the points is on the order of the magnitude of the error of the ranging system, then significant errors in platter and laser source orientation can arise because of small errors in ranging measurements. To overcome this problem, the preferred embodiment of the present invention limits point spacing to at least ten times the error of the range measurements. In practice, this is not a problem generally. For the preferred embodiment, millimeter spacing between points is obtainable, because the errors that exist in the range measurements for most applications fall below 0.1 millimeters.

Figure 25:
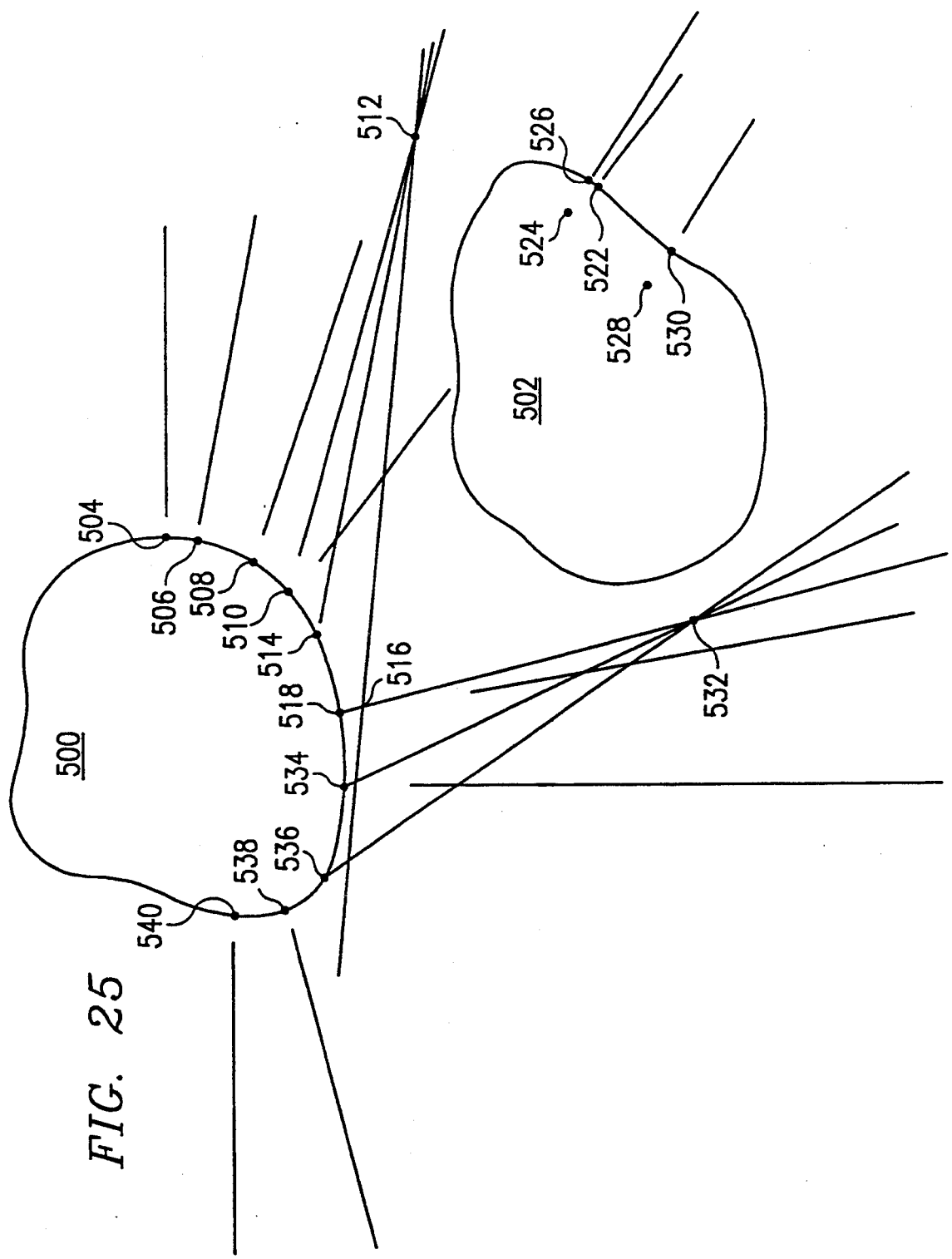
FIG. 25 illustrates the application of the adaptive scanning method of the preferred embodiment applied to a split contour object.

The preferred embodiment also has the ability to digitize split contours of 3-D objects. Consider the split contour of FIG. 25 having piece 500 and 502. Suppose, for example, that measurements begin at point 504 in the normalizing mode. Assuming that point 506 is the next point to measure followed by point 508, the adaptive scanning algorithm will continue until it expects to measure point 510. At that time, segment 502 will obstruct its view in the normalizing mode. The adaptive scanning algorithm then shifts to the pivoting mode to establish pivot point 512 from which the ranging system may measure point 510. Continuing in the pivoting mode, the system will measure point 514 on portion 500. Then, the system will expect and attempt to measure point 516, but will return an infinity measurement for its range. At this point, the tangent to the normal is much less than 30°, therefore, the adaptive scanning algorithm will then attempt to shift the laser line toward the surface normal by reversing the pivot direction and computing a new pivot point 524. When positioning through this pivot point 524 new obstruction point 526 is obtained. The adaptive scanning algorithm thus sets a new pivot point 528 at which another obstruction point 530 is encountered. This process of moving the pivot point continues until the opposite side of the obstruction is found and a successful pivot point 532 is established at which time surface point 518 is obtained. Pivoting through point 532 continues until, at surface point 536, the angle between the laser and the local surface tangent falls below the established threshold of 30 degrees and the system moves away from obstruction 502 by shifting to normalizing mode to obtain surface point 538. From this point, the adaptive scanning algorithm may continue to point 540 and continues to take measurements in the normalizing mode until it returns to point 504.

This is not the end of the scanning process, however. Once the ranging system returns to point 504 of segment 500 the ranging system considers that portion of the object fully digitized. The adaptive scanning algorithm makes a check of the data obstruction points which it stores on a stack before completing the scanning process. Remember that in attempting to measure point 510, segment 502 obstructed the laser line-of-sight at 522, for example. The preferred embodiment of the present invention records this obstructing point. Upon returning to point 504 in segment 500, the adaptive scanning algorithm checks to see whether point 522 was within the surface of segment 500. If not, the scanning algorithm causes the ranging system to go to point 522 and begins a scanning procedure to digitize segment 502.

Notice that to digitize segment 502 the adaptive scanning algorithm will begin in the normalizing mode and, upon being obstructed by segment 500, will shift to the pivoting mode. The scanning algorithm will continue in the pivoting mode until a change in pivot direction or normalizing mode is appropriate, at which time it will shift in accordance with the conditions and eventually return to point 522 having fully digitized segment 502. At that point, the scanning algorithm will examine whether the obstructions that segment 500 provided in the scanning of segment 502 have already been digitized. Since the segment 500 obstructions to segment 502 have been digitized the scanning algorithm will properly consider the surface fully digitized.

Figure 26:
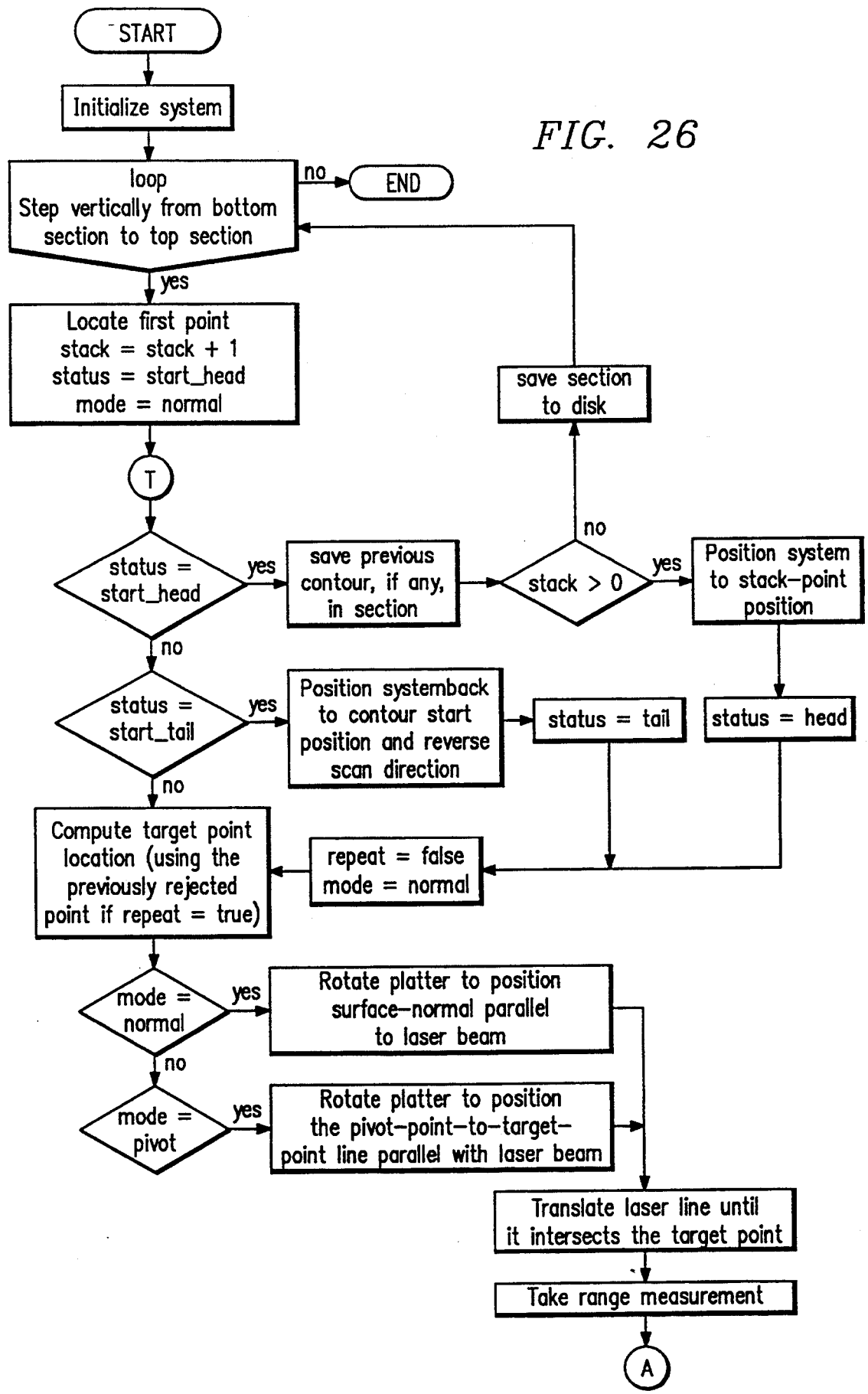

FIGS. 26 and 27 provide a flow chart of the adaptive scanning algorithm of the preferred embodiment. APPENDIX B lists the computer code for implementing the method of the preferred embodiment in the C programming language.

Although the preferred embodiment has been described in detail, it should be understood that various changes, substitutions and alterations may be made herein without departing from the spirit and scope of the invention as defined in the appended claims.

```
/* int    read_r_sensor()  -  Returns the state of the right sensor (HI=1    */
/*                            if the sensor is to move left to center on     */
/*                            the surface point, LO=0 if the sensor is to    */
/*                            move right to center on the surface point.     */
/*                            Center condition occures on transition from    */
/*                            LO to HI when moving right and HI to LO when   */
/*                            moving left.                                   */
/* void   step_sensor ()   -  This function instructs the sensor motor to    */
/*                            step once in the specified direction.          */
```

```
/* First check if the laser is incident on a surface by reading. */
/* output bit of incidense detector.                              */
i_sen = read_i_sensor();
if ( !(i_sen) ) {
   /* Laser beam not incident on surface.  Return no-range value. */
   range = 9999.0;
   return (range);
   }

/* Read initial sensor states. */
r_last = read_r_sensor();
l_last = read_l_sensor();

/* Set sensor direction based on which sensor was last used    */
/* for previous successful range measurement and the current   */
/* state of that sensor.                                       */
if (sensor == RIGHT) {
   /* Right sensor last used. */
   if (r_last = 1)
      sen_dir = LEFT;
   else
      sen_dir = RIGHT;
   }
else {
   /* Left sensor last used. */
   if (l_last = 1)
      sen_dir = RIGHT;
   else
      sen_dir = LEFT;
   }

SCAN_START:

/* Determine the number of scan steps to extreme position for */
/* specified direction.                                       */
if (sen_dir == LEFT)
   stp_cnt = sen_max - rsen_step;
else
   stp_cnt = sen_max - lsen_step;

/* Step sensor in the specified direction while checking for  */
/* center condition at either sensor or until scan extreme    */
/* is encountered.                                            */
for (i=1; i<=stp_cnt; i++) {
   /* Step sensor once in specified direction and update the  */
   /* step positions of both right and left sensors.          */
   step_sensor (sen_dir);
   rsen_step = rsen_step + (sen_dir*2 - 1);
   lsen_step = lsen_step - (sen_dir*2 - 1);
/* Read left sensor and right sensor states. */
r_sen = read_r_sensor();
l_sen = read_l_sensor();

/* Check for state transition on either left or right sensor. */
if (r_sen != r_last)  {
   /* Transition on right sensor.  Update sensor-state value. */
   r_last = r_sen;

/* Check if centering criteria satisfied (i.e. check if right */
   /* sensor transitioned to LO when moving left (sen_dir=LEFT=1) */
   /* or transitioned to HI when moving right (sen_dir=RIGHT=0).  */
   if (r_sen != sen_dir)  {
      /* Right sensor centered on light. */

/* Compute range in sensor step units. */
      range = rsen_step / tan(rsen_angle);

/* Reset last-sensor-used flag to right. */
      sensor = RIGHT;

/* Exit function by returning measured range value. */
      return (range);
```

```
        }
    } else if (l_sen != l_last) {

/* Transition on left sensor. Update sensor-state value. */
        l_last = l_sen;

/* Check if centering criteria satisfied (i.e. check if left  *
        /* sensor transitioned to HI when moving left (sen_dir=LEFT=1)*
        /* or transitioned to LO when moving right (sen_dir=RIGHT=0). *
        if (l_sen == sen_dir) {
            /* Left sensor centered on light. */

/* Compute range in sensor step units. */
            range = lsen_step / tan(lsen_angle);

/* Reset last-sensor-used flag to left. */
            sensor = LEFT;

/* Exit function by returning measured range value. */
            return (range);
        }
    }
}

/* Sensors have been scanned to extreme without centering on     */
/* point.  Check if sensor should scan back in opposite direct   */
/* or if previous scan covered entire scan length from opposite  */
/* extreme, in which case return a no-range value of 9999.0.     */
if (stp_cnt == (2*sen_max) {
    /* Scan started and finished at opposite extremes. Return the */
    /* no-range value.                                            */
    range = 9999.0;
    return (range);
}
        else {
            /* Reverse scan direction, and and repeat scan. */
            sen_dir = !sen_dir;
            goto SCAN_START;
        }
}

C-CODE FOR ADAPTIVE 3-DEGREE-OF-FREEDOM SCANNING

/****************************************************************/
/* Desciptions of supporting sub-functions:                     */
/*                                                              */
/* System functions:                                            */
/* init_db4_sys ()           - initializes hardware parameters, and */
/*                             computer interface.              */
/* init_las_sen ()           - procedure to:                    */
/*                               1) initialize the laser position both */
/*                                  horizontally and vertically, */
/*                               2) determine the sensor triangulation */
/*                                  angles by locating two reference */
/*                                  points, and                 */
/*                               3) orient the sensors with respect to */
/*                                  the platter's center of rotation. */
/* return_sys ()             - returns the platter, laser, sensors, and */
/*                             vertical systems to their start, or park */
/*                             positions.                       */
/*                                                              */
/* Mechanical positioning functions:                            */
/* pos_vertical ()           - positions the vertical lift system to */
/*                             specified location.              */
/* step_vertical ()          - steps the vertical lift system one step */
/*                             in the specified direction.      */
/* step_range_sys ()         - steps both the sensors and the laser */
/*                             projector one step in the specified */
/*                             direction.                       */
```

```
/* pos_horiz_sys ()              - positions the platter, and range system    */
/*                                 to the specified locations.                */
/* take_measurement ()           - initiates the process in which the sensors */
/*                                 are moved to locate (i.e. determine the    */
/*                                 range distance to) the illuminated surface */
/*                                 point.                                     */
/* get_laser_step ()             - returns the horizontal translation position*/
/*                                 of the laser projector along the base line.*/
/* get_platter_step ()           - returns the rotational position of platter.*/
/* read_m_sensor ()              - returns the state (i.e. bit value) of the  */
/*                                 the incidense detector (HI = laser incident*/
/*                                 on surface, LO = laser not incident on     */
/*                                 on surface.                                */
/*                                                                            */
/* Data conversion functions:                                                 */
/* conv_mm_to_sen_steps ()       - converts a single value from millimeters to*/
/*                                 sensor step units.                         */
/* conv_mm_to_vrt_steps ()       - converts a single value from millimeters to*/
/*                                 sensor step units.                         */
/* conv_plt_to_rng ()            - converts X/Y coordinate points between two */
/*                                 coordinate systems, one fixed with respect */
/*                                 to the ranging system and the other fixed  */
/*                                 with respect to the rotating platter. Both */
/*                                 coordinate systems have their origins at   */
/*                                 the platter's center of rotation with the X*/
/*                                 axis directed toward and parallel to the   */
/*                                 laser line and the Y axis extending        */
/*                                 orthonally following a "right hand"        */
/*                                 convention.  The ranging system coordate   */
```

APPENDIX R

```
/*                                 system remains fixed while the platter     */
/*                                 coordinate system rotates with the platter.*/
/*                                 Mechanical positioning and range measurement*/
/*                                 calculations are performed with range system*/
/*                                 coordinates while the data is stored in    */
/*                                 platter coordinates.                       */
/* conv_rng_to_plt ()            - converts range sytem coordinate points into*/
/*                                 platter system coordinate points.          */
/****************************************************************************/
#include <stdio.h>
#include <process.h>
#include <conio.h>
#include <math.h>
#include "digibot5.h"

/****************************************************************************/
/* System definitions. */
#define  LEFT   0
#define  RIGHT  1
#define  UP     1
#define  DOWN   0
#define  CW     1
#define  CCW    0

/* Boolean definitions. */
#define  TRUE   1
#define  FALSE  0
#define  YES    1
#define  NO     0

/****************************************************************************/
/* Global data type declarations.    */
    typedef struct {           /* Cartesian coordinate point. */
        float x,y;
    } xy_point;

typedef struct {           /* Cylindrical coordinate point. */
        float r,a;
    } ra_point;
```

```c
typedef struct {              /* Platter, and laser positions, with scan */
    int    plt, las, dir;     /* direction at a measured point P(x,y).   */
    float  x, y;
} sys_position;

/****************************************************************/
/* Global variable declarations.                                */
    char   out_fln[9],        /* Output file names*/
           out_file[13],
           param_file[13];    /* Parameter file name              */
    int    vrt_str,           /* Vertical start position (first section).*/
           vrt_end,           /* Vertical end position (last section.    */
           vrt_delta,         /* Vertical spacing between sections.      */
           rad_max,           /* Maximum scan radius from platter        */
           sec_num;           /* Number of cross-sections.               */
    float  pt_delta_min,      /* Minimum contour point spacing.          */
           pt_delta_max,      /* Maximum contour point spacing.          */
           two_pi;            /* Number of radians in full rotation.     */

/****************************************************************/
int get_start_position (int            *stack_size,
                        sys_position   stack [])

{
/* This procedure locates a starting point from the right most side */
/* of the object.                                                   */ int   min_y, max_y, m_last;

/* Move machine to far right position. */
    pos_horiz_sys (rad_max, 800);

/* Scan system to left to locate center of first contour. */
    m_last = read_m_sensor();
    min_y =  rad_max;
    max_y = -rad_max;
    for (i=1; i<=2*rad_max; i++) {
        step_range_sys (LEFT, NO);
        m_sen = read_m_sensor();
        if (m_sen != m_last) {
            /* Transition on incidense sensor. */
            m_last = m_sen;
            if (m_sen) {
                /* Transition from no incidense to incidents. Record */
                /* leading edge position.                            */
                if (get_laser_step() > max_y) {
                    max_y = get_laser_step();
                }
            }
            else {
                /* Trasition from incidense to no incidense. Record */
                /* trailing edge position.                          */
                if (get_laser_step() < min_y) {
                    min_y = get_laser_step();
                    if ((max_y-min_y) > 50) {
                        /* Sufficiently wide contour located. */
                        break;
                    }
                    else {
                        /* Insufficient contour width. Reset edge */
                        /* positions and continue scanning.       */
                        min_y =  rad_max;
                        max_y = -rad_max;
                        m_last = FALSE;
                    }
                }
            }
        }
        else if (max_y != -rad_max && (max_y-get_laser_step()) > 100) {
            /* Wide contour encountered. Record current location as */
            /* trailing edge and discontinue scan.                  */
```

```c
            min_y = get_laser_step();
            break;
        }
    }

/* Initialize the stack and control variables. */
    if (min_y != rad_max && max_y != -rad_max) {
        *stack_size = 1;
        stack[1].las = (min_y+max_y) / 2;
        stack[1].plt = 800;
        stack[1].x = 0.0;
        stack[1].y = 0.0;
        stack[1].dir = -1;
    }
    else {
        /* No incidense encountered.  Top of object reached. */
        /* Terminate scan procedure.                         */
        return (FALSE);
    } return (TRUE);
}

/*******************************************************************/
int  read_pr04_params (char   param_fln[])
{
    char   line[81];
    FILE   *p_fl;
    float  fvrt_str, fvrt_end, fvrt_delta, frad_max;
    int    v_step;

/* Open parameter file. */
    strcpy  (param_file, param_fln);
    strcat(param_file,".DB4");
    if ( (p_fl = fopen(param_file,"r")) == NULL) {
        /* Try again..... */
        clrscr();
        printf ("\nERROR: Unable to open parameter file: %s", param_file);
        return (FALSE);
    }

/* Get the output file name. */
    fgets(line, 81, p_fl);
    sscanf(line,"%s", out_fln);
    strcpy(out_file, out_fln);

/* Get height above platter for first cross_section. */
    fgets(line, 81, p_fl);
    sscanf (line,"%f",&fvrt_str);

/* Get height above platter for last cross_section. */
    fgets(line, 81, p_fl);
    sscanf (line,"%f",&fvrt_end);

/* Convert the vertical start and finish positions from */
    /* millimeters to motor step units. */
    vrt_str = conv_mm_to_vrt_steps (fvrt_str);
    vrt_end = conv_mm_to_vrt_steps (fvrt_end);

/* Get the distance between cross-sections and convert to vertical */
    /* motor step units. */
    fgets(line, 81, p_fl);
    sscanf (line,"%f",&fvrt_delta);
    vrt_delta = conv_mm_to_vrt_steps (fvrt_delta);

/* Compute the number of cross-sections. */
    sec_num = 0;
    for (v_step=0; v_step<=(vrt_end-vrt_str); v_step++) {
        if ( !(v_step % vrt_delta) ) {
            sec_num = sec_num + 1;
        }
    }
```

```c
        /* Get the minimum spacing between points along contours and */
        /* convert to sensor motor step units. */
        fgets(line, 81, p_fl);
        sscanf (line,"%f",&pt_delta_min);
        pt_delta_min = (float)conv_mm_to_sen_steps (pt_delta_min);

/* Get the maximum spacing between points along contours and */
        /* convert to sensor motor step units. */
        fgets(line, 81, p_fl);
        sscanf (line,"%f",&pt_delta_max);
        pt_delta_max = (float)conv_mm_to_sen_steps (pt_delta_max);

/* Get the maximum radius and convert to sensor motor step units. */
        fgets(line, 81, p_fl);
        sscanf (line,"%f",&frad_max);
        rad_max = conv_mm_to_sen_steps (frad_max);

fclose (p_fl);
        return (TRUE);

}

/****************************************************************/
int   nrm_trg_pt_plt (xy_point   pt2,
                      xy_point   pt1)

{
/* This procedure calculates the platter rotation steps required to   */
/* to rotate the object so that the object's surface normal rotates   */
/* toward the laser line.                                             */ float     angle;
        xy_point  delta;

/* Convert target point and pivot point to range system */
        /* coordinates.                                         */
        pt2 = conv_plt_to_rng (pt2, get_platter_step());
        pt1 = conv_plt_to_rng (pt1, get_platter_step());
        delta.y = pt2.y - pt1.y;
        if (delta.y != 0.0) {
            /* Compute the number of platter steps to rotate surface */
            /* normal to be normal to the laser line. */
            delta.x = pt2.x - pt1.x;
            angle = -atan(delta.x/delta.y) * 800./two_pi;
        }
        else {
            /* Surface normal is already parallel to laser beam. */
            angle = 0.0;
        }

/* Correct for integer truncation and return interger step number. */
        if (angle > 0.0)
            return ((int)(angle+0.5));
        else
            return ((int)(angle-0.5));

}
/****************************************************************/
int   piv_trg_pt_plt (xy_point   piv_pt,
                      xy_point   trg_pt)

{
/* This procedure calculates the platter rotation steps required to   */
/* position the pivot-point to target-point line to be parallel to    */
/* the laser line.                                                    */ float     angle;

/* Convert target point and pivot point to range system */
        /* coordinates.                                         */
        trg_pt = conv_plt_to_rng (trg_pt, get_platter_step());
        piv_pt = conv_plt_to_rng (piv_pt, get_platter_step());

/* Calculate angle between target-to-pivot point line and laser */
        /* line and convert to platter step units.                      */
```

```c
        angle = atan((piv_pt.y-trg_pt.y)/(piv_pt.x-trg_pt.x)) * (800.0/two_pi);

/* Correct for integer truncation and return interger step number. */
        if (angle > 0)
            return ((int)(angle+0.5));
        else
            return ((int)(angle-0.5));
}

/*******************************************************************/
xy_point  get_trg_pt (xy_point  pt2,
                      xy_point  pt1,
                      float     d_min,
                      float     d_max,
                      int       repeat)
{
/* This procedure calculates the location of the target point by      */
/* extrapolating the surface tangent out the the maximum specified    */
/* point spacing distance.  No consideration of rate-of or rate-of-   */
/* change-of surface curvature is made in this case.                  */ xy_point    pt3, v2, v1;
        float       v1mag;

/* Get the unit vector between previous two points. */
        v1.x = pt2.x - pt1.x;
        v1.y = pt2.y - pt1.y;
        v1mag = sqrt (pow(v1.x,2) + pow(v1.y,2));
        if (v1mag != 0.0) {
            v2.x = v1.x / v1mag;
            v2.y = v1.y / v1mag;
            }
        else {
            v2.x = 0.0;
            v2.y = 0.0;
            }

/* Compute the location of target point at a distance d_max from */
        /* previous accepted point in the unit vector, v2, direction.    */
        if (repeat) {
            /* Position target point relative to pt1. */
            pt3.x = pt1.x + v2.x*d_max;
            pt3.y = pt1.y + v2.y*d_max;
            }
        else {
            /* Position target point relative to pt2. */
            pt3.x = pt2.x + v2.x*d_max;
            pt3.y = pt2.y + v2.y*d_max;
            }
        return (pt3);
}

/*******************************************************************
main (int argc, char **argv)
{
/* Addaptive scanning procedure using three machanical degrees of freedom: *
/*   1.  rotation of object about a vertical axis,                         *
/*   2.  vertical translation of object or laser line, and                 *
/*   3.  horizontal translation of laser line.                             *

/* Local data type definitions. */
        enum modes  {NORMAL, PIVOT};
        enum statis {START_HEAD, HEAD, START_TAIL, TAIL};

/* Local variable declarations. */
        FILE     *o_fl;           /* Output file pointer.           */
        char     param_fln[9];    /* Parameter file name.           */
        int      i,j,k,l,m,n,     /* Loop indecies.                 */
                 v_step,          /* Vertical position loop index.  */
                 pt_cnt,          /* Number of contour points.      */
                 pt_tot,          /* Number of section points       */
```

```
                        contour_cnt,       /* Number of contours on section.   */
                        section_cnt;       /* Number of cross-sections.        */
        float           pt_delta,          /* Distance from current point to   */
                                           /* first contour point.             */
                        tst_delta          /* Distance between stack point and */
                                           /* contour points.                  */
                        pt_angle,          /* Angle between surface tangent    */
                                           /* and sensor rail axis.            */
                        pt_length,         /* Distance between new point and   */
                                           /* previously accepted point.       */
                        las_angle;         /* Laser incidense angle.           */
        int             trg_pt_plt,        /* Number of platter steps to       */
                                           /* position on target point.        */
                        trg_pt_las,        /* Number of laser steps to         */
                                           /* position on target point.        */
                        piv_dir,           /* Pivot direction (left or rigth). */
                        scan_dir,          /* Scan direction (left or right).  */
                        repeat,            /* Flag to repeat point measuremen+ */
                        stack_size,        /* Number of points on stack.       */
                        plt_delta,         /* Step position change of platter. */
                        las_delta,         /* Step position change of laser.   */
                        plt_last,          /* Previous platter position.       */
                        m_last,            /* Previous incidense sensor state  */
                        m_sen;             /* Current incidense sensor state   */
        xy_point        pt,                /* Newly acquired point.            */
                        pt2, pt3,          /* Previous two accepted points.    */
                        piv_pt,            /* Pivot point.                     */
                        trg_pt,            /* Target point.                    */
                        pt_tan,            /* Local surface tangent given by   */
                                           /* vector between last two points   */
                        pt_rng,            /* New point in range system coords */
                        pt_tmp;            /* Temporary point to reverse point */
                        pts[1001],         /* Contour points array.            */
                        xpts[1001];        /* Section points array.            */
        sys_position    stack[501],        /* Stack points (i.e. obstruction   */
                                           /* points) array with associated    */
                                           /* platter and laser orientations.  */
                        contour_start;     /* First contour point location and */
                                           /* associated platter and laser     */
                                           /* measurement orientations.        */
        enum modes      mode;              /* Scan mode (NORMAL or PIVOT).     */
        enum statis     contour_statis;    /* Contour scan statis.             */

/* Initialize system parameters. */
        two_pi = 8.0 * atan(1.0);
        strcpy (param_fln, argv[1]);
        init_db4_sys (4);

/* Read scan parameters from .DB5 file. */
        if ( !(read_pr04_params(param_fln)) ) {
            /* Unable to read parameter file. */
            exit(1);
        }

/* Open data output file. */
        strcpy(out_file, argv[2]);
        strcat(out_file,".DAT");
        if( (o_fl = fopen(out_file,"w")) == NULL) {
            printf("\nERROR: Unable to open output file: %s", out_file);
            exit(1);
        }

/* Write grid dimensions to output file. */
        fprintf(o_fl,"%d\n", sec_num);

/* Initialize the ranging system and positioning systems. */
        init_las_sen();

/* Perform object scan. */

/* Position vertical to start position. */
        pos_vertical (vrt_str);
```

```
/* Loop over vertical positions stopping at specified locations.  */
contour_statis = START_HEAD;
section_cnt = 0;
stack_size = 0;

for (v_step=0; v_step<=(vrt_end-vrt_str); v_step++) {
    /* Step vertically one step up. */
    step_vertical (UP);

if ( !(v_step % vrt_delta) ) {
        /* Measure cross-section at current vertical position. */
        section_cnt = section_cnt + 1;

REPEAT_START:
        /* Locate starting point on right-most contour. */
        if (!get_start_position (&stack_size, stack)) {
            /* Starting point not located.  Continue on to next */
            /* cross-section.                                    */
            break;
        }

/* Initialize scan parameters. */
        pt_tot = 0;
        contour_statis = START_HEAD;
        piv_dir = 1;
        piv_pt.x = 0.0;
        piv_pt.y = 0.0;
        repeat = FALSE;
        pt_cnt = 0.0;
        mode = NORMAL;

/* Points loop.  Continue taking points until stop-condition. *
        TAKE_POINT:

if (contour_statis == START_HEAD) {
            /* Save previous contour in cross-section array. */
            if (repeat)
                pt_cnt = pt_cnt - 1;
            if (pt_cnt > 1) {
                pt_tot = pt_tot + 1;
                xpts[pt_tot].x = 9999.1;
                for (i=2; i<=pt_cnt; i++) {
                    pt_tot = pt_tot + 1;
                    xpts[pt_tot] = pts[i];
                }
                pt_cnt = 0;
            }

/* Check if next stack point in existing contours. */
            if (stack_size > 0) {
                contour_start = stack[stack_size];
                for (i=1; i<=pt_tot; i++) {
                    tst_delta = sqrt (pow(xpts[i].x-contour_start.x,2) +
                                     pow(xpts[i].y-contour_start.y,2));
                    if (tst_delta < 1.5*pt_delta_max) {
                        /* Stack point part of existing contour. */
                        /* remove point from stack.              */
                        stack_size = stack_size - 1;
                        goto TAKE_POINT;
                    }
                }

/* Start new contour at current stack position. */
                pos_horiz_sys (contour_start.las, contour_start.plt);
                stack_size = stack_size - 1;
                pt = take_measurement();

/* Record contour start position and initial point */
                /* values.                                          */
                contour_start.x = pt.x;
                contour_start.y = pt.y;
                pt_cnt = 2;
```

```
                pts[2] = pt;
                pt = conv_plt_to_rng (pt, get_platter_step());
                pt.y = pt.y - pt_delta_max * contour_start.dir;
                pts[1] = conv_rng_to_plt (pt, get_platter_step());
                pt.y = pt.y - pt_delta_max * contour_start.dir;
                pts[0] = conv_rng_to_plt (pt, get_platter_step());
                /* Set scan direction, repeat flag, scan mode, and  */
                /* contour statis.                                  */
                scan_dir = contour_start.dir;
                repeat = FALSE;
                mode = NORMAL;
                contour_statis = HEAD;
            }
        else {
            /* Cross-section complete. Continue to next section. */

/* Write section to output file and continue to next */
            /* cross-section.       */

/* Write Z-value to output file.  */
            fprintf(o_fl,"Section: %d\n%5d\n", section_cnt,
            (int)(conv_vrt_steps_to_mm(vrt_str+v_step)*10.0));

/* Write X/Y-values to output file. */
            contour_cnt = 0;
            for (i=1; i<=pt_tot; i++) {
                if ((int)xpts[i].x == 9999) {
                    contour_cnt = contour_cnt + 1;
                    fprintf(o_fl,"Contour: %d\n",contour_cnt);
                }
                else {
                    fprintf(o_fl,"%5d %5d\n",
                        (int)(conv_sen_steps_to_mm(xpts[i].x)*10.0),
                        (int)(conv_sen_steps_to_mm(xpts[i].y)*10.0));
                }
            } continue;  /* To next cross-section. */
            }
        } else if (contour_statis == START_TAIL) {
        /* Reverse the 'pts' array and procede in normal mode. */
        if (repeat)
            pt_cnt = pt_cnt - 1;
        i = 2;
        j = pt_cnt;
        do {
            pt_tmp = pts[i];
            pts[i] = pts[j];
            pts[j] = pt_tmp;
            i = i + 1;
            j = j - 1;
        } while (j > i);

/* Position system back at start position. */
        pos_horiz_sys (contour_start.las, contour_start.plt);

/* Set scan parameters. */
        scan_dir = -scan_dir;
        repeat = FALSE;
        mode = NORMAL;
        contour_statis = TAIL;
        contour_start.x = pts[2].x;
        contour_start.y = pts[2].y;
        }

/* Compute the location of target point. */
    trg_pt = get_trg_pt (pts[pt_cnt], pts[pt_cnt-1],
                    pt_delta_min, pt_delta_max, repeat);
```

```
/* Compute system rotation for target point. */
if (mode == NORMAL) {
   /* Compute the platter rotation to reduce incident angle. */
   if (repeat)
      plt_delta = nrm_trg_pt_plt (trg_pt, pts[pt_cnt-1]);
   else
      plt_delta = nrm_trg_pt_plt (trg_pt, pts[pt_cnt]);
}
else {
   /* Platter rotation to line-up pivot with target point. */
   plt_delta = piv_trg_pt_plt (piv_pt, trg_pt);
}

/* Compute the number of platter rotation steps. */
trg_pt_plt = get_platter_step() + plt_delta;
if (trg_pt_plt > 800)
   trg_pt_plt = trg_pt_plt - 800;
else if (trg_pt_plt < 1)
   trg_pt_plt = trg_pt_plt + 800;

/* Convert target point to range-system coordinates. */
trg_pt = conv_plt_to_rng (trg_pt, trg_pt_plt);

/* Compute the laser translation to target point. */
las_delta = trg_pt.y - get_laser_step();

/* Position system on target point. */
pos_horiz_sys (trg_pt.y, trg_pt_plt);

/* Take measurement. */
pt = take_measurement();

/* Check point validity and keep, repeat, or change mode. */
if ((int)pt.x == 9999) {
   /* Unable to locate surface point.  Set point to distant */
   /* value and convert to platter coordinates.             */
   pt.x = -pt.x;
   pt.y = get_laser_step();
   pt = conv_rng_to_plt (pt, get_platter_step());
}

/* Get surface tangent vector between new point and last   */
/* accepted point, convert to range coordinates, and       */
/* determine surface tangent angle relative to laser line. */
if (repeat) {
   pt_tan.x = pt.x - pts[pt_cnt-1].x;
   pt_tan.y = pt.y - pts[pt_cnt-1].y;
}
else {
   pt_tan.x = pt.x - pts[pt_cnt].x;
   pt_tan.y = pt.y - pts[pt_cnt].y;
}
pt_tan = conv_plt_to_rng (pt_tan, get_platter_step());
pt_angle = atan (pt_tan.y / pt_tan.x);

/* Compute the distance between new point and previously */
/* accepted point.                                       */
pt_length = sqrt (pow(pt_tan.x,2) + pow(pt_tan.y,2));

/* Check if new point is within specified point spacing. */
if (pt_length <= pt_delta_max && pt_length >= pt_delta_min) {
   /* Keep point and continue contour. */

/* Record point in contour array. */
   if (repeat) {
      pts[pt_cnt] = pt;
      repeat = FALSE;
   }
   else {
      pt_cnt = pt_cnt + 1;
      pts[pt_cnt] = pt;
   }
```

```
      /* Check for complete contour (i.e. new point within    */
      /* specified point spacing tolerance of first acquired  */
      /* contour point.                                       */
      if (pt_cnt > 3) {
         /* Check for complete contour. */
         pt_delta = sqrt(pow(pt.x-contour_start.x, 2) + pow(pt.y-
                         contour_start.y, 2));
         if (pt_delta < pt_delta_max) {
            /* STOP. Contour is complete. */ if (contour_statis == TAIL) {
               /* Stop at contour edge.  Reverse the 'pts'   */
               /* array and continue  on to next contour or  */
               /* next section.                              */
               if (repeat)
                  pt_cnt = pt_cnt - 1;
               i = 2;
               j = pt_cnt;
               do {
                  pt_tmp = pts[i];
                  pts[i] = pts[j];
                  pts[j] = pt_tmp;
                  i = i + 1;
                  j = j - 1;
                  } while (j > i);
               }
            contour_statis = START_HEAD;
            goto TAKE_POINT;
            }
         }

/* Check for small incidense angle in pivot mode and    */
      /* either switch pivot direction or transition to       */
      /* NORMAL mode to position laser more normal to target  */
      /* point.                                               */
      if (mode == PIVOT &&  fabs(pt_angle) < two_pi/10.0) {
         /* Small incidense angle.  Check to shift toward or  */
         /* away from obstruction.                            */
         if ( (pt_angle < 0.0  &&  piv_dir > 0) ||
              (pt_angle > 0.0  &&  piv_dir < 0)      ) {

/* Go to normal mode to shift away from obstruction.*/
            mode = NORMAL;
            }
         else {
            /* Reverse pivot direction, compute new pivot point */
            /* location, and attempt to pivot off opposite side */
            /* of obstruction.                                  */
            piv_dir = -piv_dir;
            piv_pt = conv_plt_to_rng (piv_pt, get_platter_step());
            piv_pt.y = piv_pt.y + (piv_dir*6.0*pt_delta_max);
            piv_pt = conv_rng_to_plt (piv_pt, get_platter_step());
            }
         }
      } else {
      /* Reject point.  Adjust to repeat, shift mode, or stop */
      /* at edge.                                             */

/* Check for edge stop condition when laser on opposite */
      /* side of surface.                                     */
      if (repeat) {
         pt2 = conv_plt_to_rng (pts[pt_cnt-1], get_platter_step());
         pt3 = conv_plt_to_rng (pts[pt_cnt-2], get_platter_step());
         }
      else {
         pt2 = conv_plt_to_rng (pts[pt_cnt], get_platter_step());
         pt3 = conv_plt_to_rng (pts[pt_cnt-1], get_platter_step());
         }
```

```
    las_angle = atan2 (pt2.y-pt3.y, pt2.x-pt3.x);
    if ( (scan_dir > 0  &&  las_angle < -two_pi/10.0)  ||
         (scan_dir < 0  &&  las_angle >  two_pi/10.0)    ) {
       /* Laser on opposite side of surface.   */
       /* STOP at contour edge.                */
       if (contour_statis == HEAD) {
          /* Switch scan direction to finish tail-end   */
          /* of contour.                                */
          contour_statis = START_TAIL;
       }
       else {
          if (contour_statis == TAIL) {
             /* Stop at contour edge.  Reverse the 'pts'    */
             /* array and continue  on to next contour or   */
             /* next section.                               */
             if (repeat)
                pt_cnt = pt_cnt - 1;
             i = 2;
             j = pt_cnt;
             do {
                pt_tmp = pts[i];
                pts[i] = pts[j];
                pts[j] = pt_tmp;
                i = i + 1;
                j = j - 1;
             } while (j > i);
          }
          contour_statis = START_HEAD;
       }
    }
    /* Check for obstruction condition and set new pivot. */
    else if (pt_tan.x > (3.0*pt_delta_max)) {
       /* Obstruction in front of laser.  Set pivot. */
       pt_rng = conv_plt_to_rng (pt, get_platter_step());

/* Check for transition from NORMAL to PIVOT mode.  */
       if (mode == NORMAL) {
          /* Switch mode to PIVOT.                                */
          /* Determine direction from which obstruction came      */
          /* and set the pivot direction accordingly by           */
          /* determining the direction in which the               */
          /* obstruction crossed over the laser line.             */
          plt_last = get_platter_step() - plt_delta;
          if (plt_last > 800)
             plt_last = plt_last - 800;
          else if (plt_last < 1)
             plt_last = plt_last + 800;
          pt_tmp = conv_plt_to_rng (pt, plt_last);
          piv_dir = (pt_rng.y - pt_tmp.y) - las_delta;
          if (piv_dir < 0)
             piv_dir = -1;
          else
             piv_dir = 1;
       }

/* Compute new pivot point location in platter  */
       /* coordinates, change mode to PIVOT and store  */
       /* obstruction point on the stack.              */
       piv_pt.x = pt_rng.x;
       piv_pt.y = pt_rng.y + (piv_dir*3.0*pt_delta_max);
       piv_pt = conv_rng_to_plt (piv_pt, get_platter_step());
       mode = PIVOT;
       if (stack_size < 500) {
          /* Store obstruction point on stack.  */
          stack_size = stack_size + 1;
          stack[stack_size].las = get_laser_step();
          stack[stack_size].plt = get_platter_step();
          stack[stack_size].dir = -piv_dir;
          stack[stack_size].x = pt.x;
          stack[stack_size].y = pt.y;
       }
    }
```

```
/* Check for small incidense angle in pivot mode and     */
/* either switch pivot direction or transition to        */
/* NORMAL mode to position laser more normal to target   */
/* point.                                                */
else if (mode == PIVOT  ?  fabs(pt_angle) < two_pi/10.0) {
    /* Small incidence angle.  Check to shift toward or  */
    /* away from obstruction.                            */
    if ( (pt_angle < 0.0  &&  piv_dir > 0) ||
         (pt_angle > 0.0  &&  piv_dir < 0)   ) {
        /* Go to normal mode to shift away from obstruction.*/
        mode = NORMAL;
        if (!repeat)
            pt_cnt = pt_cnt + 1;
        pts[pt_cnt] = pt;
        repeat = TRUE;
    }
    else {
        /* Reverse pivot directic.., compute new pivot point */
        /* location, and attempt to pivot off opposite side  */
        /* of obstruction.                                   */
        piv_dir = -piv_dir;
        piv_pt = conv_plt_to_rng (piv_pt, get_platter_step());
        piv_pt.y = piv_pt.y + (piv_dir*6.0*pt_delta_max);
        piv_pt = conv_rng_to_plt (piv_pt, get_platter_step());
        if (!repeat)
            pt_cnt = pt_cnt + 1;
        pts[pt_cnt] = pt;
        repeat = TRUE;
    }
}

/* Repeat attempt to find next point by computing a new  */
/* target point location using the location of rejected  */
/* point.                                                */
else {
    if (!repeat)
        pt_cnt = pt_cnt + 1;
    pts[pt_cnt] = pt;
    repeat = TRUE;
}
goto TAKE_POINT;
    }
}

/* Object scan completed.          */
/* Return system to start position. */
        return_sys();

/* Close output file.  */
        fclose(o_fl);

}
```

What is claimed is:

1. A four-axis method for scanning the surface of an object using translation of a ranging device along its axis and either two translations and one rotation or two rotations and one translation between the axis of a ranging device and the surface of the object to collect a set of surface points, which taken together, provide a digital, three-dimensional, surface representation of the object, comprising the steps of:

acquiring a plurality of sequentially-connected surface points on a plurality of surface contours contained on a sequence of spaced cross-sections through the object;

locating at least one starting surface point for each contour on a cross-section through the object;

scanning each contour by beginning at the starting surface point and moving in one of two scan directions while measuring a plurality of adaptively-spaced surface points, which taken in sequence, comprise the shape of the contour;

adaptively rotating and scanning the axis of a ranging device along the contours of the object to measure a series of the adaptively-spaced surface points, the orientations of the axis of the ranging device relative to the surface of the object, and the spacing between subsequent surface points being derived by predicting the locations and corresponding surface normals of subsequent surface points estimated from two or more previously-acquired surface points;

adaptively and automatically scanning along the contours of the object in either a normalizing mode along a convex surface regions or a pivoting mode along concave surface regions to locate the nature and ordered sequence of a set of orientations that are most normal between the axis of the ranging device and the surface contours of the object;

returning to the starting point of a contour and scanning in the direction opposite the initial scan direction in the event that a contour edge is encountered for which no additional points can be located in the estimated region beyond the last acquired points;

terminating a contour scan in the event that either 1) the contour is completed such that the ranging device has made a full scan around the contour and has returned to the contour's starting point arriving at the contour's starting point from the direction opposite the scan direction, or 2) a second edge condition is encountered to the effect that no additional points can be located in the estimated region beyond both ends of the contour, thereby resulting in an incomplete contour.

2. The method of claim 2, wherein locating first starting points and beginning to scan a contour on a cross-section comprises the steps of:

traversing across the cross-sectional width of the object with a sensor that acts along the axis of the ranging device to determine if the axis of the ranging device intersects the surface of the object for locating all locations and orientations for which the axis of the ranging device initially or finally traversed a surface of the object;

positioning the axis of the ranging device between all pairs of bounding edges between which the object resides to obtain, by range measurement, one or more initial surface points;

storing all of the initial surface points and the corresponding orientations between the ranging device and the object in an initial surface points list;

upon finishing a contour, removing all initial surface points from the initial surface points list that belong to previously acquired contours on the cross-section;

selecting one of the points from the remaining list of initial surface points and positioning the ranging device and object in accordance to the corresponding stored orientation between the ranging device and the object to begin scanning a new contour.

3. The method of claim 1, further comprising the step of predicting the relative direction and spacing distance relative to the last surface point of a subsequent surface point by extrapolating or interpolating the local surface tangent, the local surface curvature, and the local rate-of-change of surface curvature between two or more previously acquired surface points, such that the location of the predicted point follows the natural curvature of the objects surface and the point spacing reduces to a minimum in rapidly curving surface regions and increases to a maximum in generally flat surface regions.

4. The method of claim 1, further comprising the step of subjecting each newly-acquired surface point to an acceptance criteria for rejecting those surface points that are outside a range having a minimum and maximum distance from the previously-accepted surface point while accepting all other surface points and adding the other surface points to a surface point list for the contour.

5. The method of claim 1, further comprising the step of using surface points that differ from their corresponding predicted surface points by a distance beyond a pre-established acceptance criteria in calculations to estimate the location of a next predicted surface point.

6. The method of claim 1, wherein proceeding to take a next contour surface point in said normalizing scan mode comprises the steps of:

calculating the location of a next predicted surface point using previously acquired surface points;

positioning the ranging device and the object such that the axis of the ranging device passes through the predicted surface point in a normal orientation such that the local predicted surface tangent is approximately 90 degrees to the axis of the ranging device;

performing a range measurement to acquire the true surface point for the established orientation between the ranging device and the object.

7. The method of claim 1, wherein, upon encountering an obstructing surface while scanning in the normalizing mode, switching from the normalizing mode to the pivoting mode and subsequently setting an initial pivot direction and establishing the location of an initial pivot point comprises the steps of:

recognizing that the previously measured surface point is an obstructing point such that the distance between the measured surface point location and a corresponding predicated surface point location is greater than a pre-established threshold and that the measured surface point location is between the predicted surface point and the ranging device along the axis of the ranging device;

setting the pivot direction to be the orthogonal direction relative to the axis of the ranging device for which the obstruction point moved to intersect the axis of the ranging system;

establishing the location of a pivot point to be that location a pre-established distance from the obstruction surface point along the pivot direction.

8. The method of claim 1, wherein proceeding to take a next contour point in pivoting scan mode comprises the steps of:

calculating the location of a next predicted surface point using previously acquired surface points;

positioning the ranging device and the object such that the axis of the ranging device passes through both a pre-established pivot point and the predicted surface point;

performing a range measurement to acquire the true surface point for the established orientation between the ranging device and the object.

9. The method of claim 1, wherein, upon encountering an obstructing surface while scanning in pivoting mode, setting a new pivot point comprises the steps of:

recognizing that the previously measured surface point is an obstruction surface point such that the distance between the measured point location and its corresponding predicted surface point location is greater than a pre-established threshold and that the measured surface point location is between the predicted surface point and the ranging device along the axis of the ranging device;

establishing the location of a pivot point to be that location a pre-established distance from the obstruction surface point along the established pivot direction.

10. The method of claim 1, further comprising the step of, while scanning in pivot mode, proceeding to locate a pivot point on the opposite side of an obstructing surface by reversing the pivot direction in the event that the angle between the predicted surface normal of a predicted surface point and the axis of the ranging device exceeds a predetermined incidence angle limit and further that to decrease said incidence angle requires movement of said ranging device axis in the direction toward said obstructing surface.

11. The method of claim 1, further comprising the step of switching from the pivoting mode to the normalizing mode in the event that the angle between the predicted surface normal of a predicted surface point and the axis of the ranging device exceeds a predetermined incidence angle limit and further that to decrease said incidence angle requires movement of said ranging device axis in the direction away from an obstructing surface.

12. The method of claim 1, further including the steps of identifying the existence of other contours on a multiple contour cross-section, obtaining the location of a first surface point and the corresponding orientation of the ranging device to pass through the first surface point for each of the other contours, and subsequently initializing the scan of all the other contours on a section, said scan initializing steps comprising:
 storing a list of obstruction surface points that were measured on an obstructing contour that moved into the axis of the ranging device between the ranging device and a predicted surface point and the corresponding orientations between the obstructing points and the ranging device;
 removing from the list of obstruction surface points all obstructing surface points that belong to previously-acquired contours on the cross-section;
 selecting one of the obstructing surface points from the remaining list of obstructing surface points and positioning the ranging device and object in accordance to the corresponding stored orientation between the ranging device and the obstructing surface point to begin scanning a new contour.

13. The method of claim 12, further comprising the step of determining that a cross-section is complete in the event that, upon completing a contour scan, both the list of obstructing surface points and a list of surface points for the contour are empty.

14. A method for scanning an object to form a three-dimensional digital representation of the object, comprising the steps of:
 locating sequentially and automatically a set of orientations between a ranging device and the surface of the object;
 deriving a plurality of range measurements that when taken together describe the surface of the object in three dimensions;
 calculating a predicted surface point as a function of previously-measured surface points;
 measuring a surface point corresponding to said predicted surface point; and
 adaptively switching from a first mode to perform a second mode of deriving said plurality of range measurements in the event that said measured surface point differs beyond predetermined acceptance criteria from said predicted surface point due to an obstruction between the surface and said ranging device.

15. The method of claim 14, further comprising the step of identifying a first surface point on the surface for locating an orientation between the surface and said ranging device by determining a cross section of the object.

16. The method of claim 14, further comprising the step of storing a measured point that differs beyond predetermined acceptance criteria as an estimator for a next predicted surface point.

17. The method of claim 14, further comprising the steps of:
 calculating the curvature of the surface; and
 deriving said range measurements at calculated point spacings on the surface, said calculated point spacings determined at least in part by said calculated curvature.

18. The method of claim 14, wherein said first mode of deriving said range measurements comprises the steps of deriving said range measurements by determining said orientations in a normalizing mode as a function of normal orientations between the surface and said ranging device.

19. The method of claim 14, wherein said second mode of deriving said range measurements comprises the steps of deriving said range measurements in a pivoting mode as a function of orientations between the surface and said ranging device through a pivot point, said pivot point being a predetermined distance removed from an obstructing surface of the object.

20. The method of claim 14, wherein said second mode of deriving said plurality of range measurements comprises the steps of:
 deriving said range measurements in a pivoting mode as a function of orientations between the surface and said ranging device through a pivot point;
 beginning said pivoting mode in a first direction; and
 changing the direction of said pivoting mode in the event that the incidence angle between the surface and said ranging device exceeds a predetermined incidence angle limit and further that to decrease the incidence angle requires movement of said ranging device in the direction of said obstruction.

21. The method of claim 14, further comprising the step of adaptively switching from said second mode to said first mode of deriving said range measurements in the event that the incidence angle of orientation between the surface and said ranging device exceeds a predetermined incidence angle limit and further that to decrease said incidence angle requires movement of said ranging device in the direction away from said obstruction.

22. The method of claim 14, further comprising the step of deriving said range measurements at calculated point spacings in said range measurement, said calculated point spacings being within a point spacing range, said point spacing range comprising a minimum acceptable point spacing and a maximum acceptable point spacing.

23. The method of claim 22, further comprising the step of identifying an edge on the surface in the event that no measured surface point can be located or obtained within said surface point spacing range.

24. The method of claim 23, further comprising the step of reversing the relative direction of movement between the object and said ranging device in the event that an edge condition exists and no prior direction reversal has already occurred.

25. The method of claim 23, further comprising the step of determining that a surface contour is complete in the event that an edge condition exists and a prior direction reversal has already occurred.

26. The method of claim 14, further comprising the steps of:
 storing all measured surface points beyond said predetermined acceptance criteria as rejected points;

determining whether all rejected points correspond to previously measured contours upon finishing a contour of the cross-section;

identifying a next contour of the surface in the event that any rejected points fail to correspond to surface points on any said previously measured contour; and scanning said next contour using at least one of said non-corresponding rejected points as a first point on said next contour.

27. A four-axis system for scanning the surface of an object, comprising:

a ranging device translatable along a predetermined axis and configured for selectively performing either two translations and one rotation or two rotations and one translation between said predetermined axis and the surface of the object to form a set of surface points which taken together provide a digital, three-dimensional, surface representation of the object;

collecting circuitry for acquiring a plurality of sequentially-connected surface points on a plurality of surface contours contained on a sequence of spaced cross-sections through the object;

a processor associated with said ranging device and said collecting circuitry and comprising:

instructions for locating at least one first surface point for each contour on a cross-section through the object;

instructions for scanning each contour by beginning at said first surface point and moving in one of two scan directions while measuring a plurality of adaptively-spaced surface points, which taken in sequence, comprise the geometry of said contour;

instructions for adaptively rotating and translating said predetermined axis along said contours to measure an estimated region comprising a series of said adaptively-spaced surface points, the orientations of said predetermined axis relative to the surface of the object, and the spacing between subsequent ones of said surface points being derived by predicting the locations and corresponding surface normals of subsequent surface points estimated from two or more previously-acquired surface points;

instructions for adaptively and automatically scanning along said contours of the object in either a normalizing mode along convex surface regions or a pivoting mode along concave surface regions to locate the nature and ordered sequence of a set of orientations that are most normal between said predetermined axis and said contours;

instructions for returning to said first surface point and scanning in said direction opposite the initial scan direction in the event that a contour edge is encountered for which no additional points can be located in said estimated region beyond the last acquired points; and instructions for terminating a contour scan in the event that either 1) the contour is completed such that the ranging device has made a full scan around the contour and has returned to the contour's starting point arriving at the contour's starting point from the direction opposite the scan direction, or 2) a second edge condition is encountered to the effect that no additional points can be located in the extrapolated region beyond both ends of the contour, thereby resulting in an incomplete contour.

28. The system of claim 27, wherein said first surface point locating instructions and scan beginning instructions comprise:

instructions for traversing across the cross-sectional width of the object with an in-line incidence sensor to locate all bounding edges of the object;

instructions for positioning the axis of the ranging device between all pairs of bounding edges between which the object resides to obtain, by range measurement, one or more initial surface points;

instructions for storing all of the initial surface points and the corresponding orientations between the ranging device and the object in an initial surface points list;

instructions for, upon finishing a contour, removing all surface points from the initial surface points list that belong to previously acquired contours on the cross-section; and instructions for selecting one of the points from the remaining list of initial surface points and positioning the ranging device and object in accordance to the corresponding stored orientation between the ranging device and the object to begin scanning a new contour.

29. The system of claim 27, further comprising instructions for predicting the location of a subsequent surface point by extrapolating or interpolating the local surface tangent, the local surface curvature, and the local rate-of-change of surface curvature between two or more previously acquired surface points, such that the location of the predicted point follows the natural curvature of the objects surface and the point spacing reduces to a minimum in rapidly curving surface regions and increases to a maximum in generally flat surface regions.

30. The system of claim 27, further comprising instructions for subjecting each newly-acquired surface point to an acceptance criteria for rejecting those surface points that are outside a range having a minimum and maximum distance from said previously-accepted surface point while accepting all other surface points and adding the other surface points to a surface point list for the contour.

31. The system of claim 27, further comprising instructions for using surface points that differ from their corresponding predicted surface points by a distance beyond a pre-established acceptance criteria in calculations to estimate by extrapolation or interpolation the location of a next predicted surface point.

32. The system of claim 27, wherein said instructions for adaptively and automatically scanning along said contours further comprise:

instructions for calculating the location of a next, predicted surface point using previously acquired surface points;

instructions for positioning the ranging device and the object such that the axis of the ranging device passes through the predicted surface point in a normal orientation such that the local predicted surface tangent is closely normal to the axis of the ranging device; and instructions for performing a range measurement to acquire the true surface point for the established orientation between the ranging device and the object.

33. The system of claim 27, further comprising instructions for, upon encountering an obstructing surface while scanning in said normalizing mode, switching from said normalizing mode to said pivoting mode and subsequently setting an initial pivot direction, said switching instructions further comprising:

instructions for recognizing that the previously measured surface point is an obstructing point such that the distance between the measured surface point location and a corresponding predicated surface point location is greater than a pre-established threshold and that the measured surface point location is closer to the ranging device along said predetermined axis;

instructions for setting the pivot direction to be the orthogonal direction relative to the axis of the ranging device for which the obstruction point moved to intersect the axis of the ranging system;

instructions for establishing the location of a pivot point to be that location a pre-established distance from the obstruction surface point along the pivot direction.

34. The system of claim 27, wherein instructions for taking a next contour point in said pivoting scan mode further comprise:

instructions for calculating the location of a next predicted surface point using previously acquired surface points;

instructions for positioning the ranging device and the object such that the axis of the ranging device passes through both a pre-established pivot point and the predicted surface point; and instructions for performing a range measurement to acquire the true surface point for the established orientation between the ranging device and the object.

35. The system of claim 27, further comprising instructions for, upon encountering an obstructing surface while scanning in pivoting mode, switching from said pivoting mode to said normalizing mode and subsequently setting an initial pivot direction, said switching instructions further comprising:

instructions for recognizing that the previously measured surface point is an obstruction surface point such that the distance between the measured surface point location and its corresponding predicted surface point location is greater than a pre-established threshold and that the measured surface point location is closer to the ranging device along the axis of the ranging device; and instructions for establishing the location of a pivot point to be that location a pre-established distance from the obstruction surface point along the established pivot direction.

36. The system of claim 27, further comprising instructions for, while scanning in pivot mode, proceeding to locate a pivot point on the opposite side of an obstructing surface by reversing the pivot direction in the event that the incident angle exceeds a predetermined incidence angle limit and further that to decrease said incidence angle requires movement of said ranging device axis in the direction toward said obstructing surface.

37. The system of claim 27, further comprising instructions for switching from said pivoting mode to said normalizing scan mode in the event that the incident angle exceeds a predetermined incidence angle limit and further that to decrease said incidence angle requires movement of said ranging device axis in the direction away from an obstructing surface.

38. The system of claim 27, further including instructions for identifying the existence of other contours on a multiple contour cross-section, obtaining the location of a first point and the corresponding orientation of the ranging device to pass through the first surface point for each of the other contours, and subsequently initializing the scan of all the other contours on a section, said scan initializing instructions comprising:

instructions for storing a list of obstructing surface points and the corresponding orientations between the obstructing surface points and the ranging device;

instructions for removing from the list of obstructing surface points all obstructing surface points that belong to previously acquired contours on the cross-section; and instructions for selecting one of the obstructing points from the remaining list of obstructing surface points and positioning the ranging device and object in accordance to the corresponding stored orientation between the ranging device and the obstructing surface point to begin scanning a new contour.

39. The system of claim 38, further comprising instructions for determining that a cross-section is complete in the event that, upon completing a contour scan, both the list of obstructing surface points and a list of surface points for the contour are empty.

40. A system for scanning an object to form a three-dimensional digital representation of the object, comprising:

a ranging system generating a plurality of range measurements, between a surface point on the object and a predetermined location;

a processor for controlling the operation of said ranging system according to a set of executable instructions, comprising:

instructions for locating sequentially and automatically a set of orientations between a ranging device and the surface of the object;

instructions for deriving a plurality of range measurements that when taken together describe the surface of the object in three dimensions;

instructions for calculating a predicted surface point as a function of previously-measured surface points;

instructions for measuring a surface point corresponding to said predicted surface point; and instructions for adaptively switching from a first mode to perform a second mode of deriving said plurality of range measurements in the event that said measured surface point differs beyond predetermined acceptance criteria from said predicted surface point due to an obstruction between the surface and said ranging device.

41. The system of claim 40, wherein said executable instructions further comprise instructions for identifying a first surface point on the surface for locating an orientation between the surface and said ranging device by determining a cross section of the object.

42. The system of claim 40, wherein said executable instructions further comprise instructions for storing a measured point that differs beyond predetermined acceptance criteria as an estimator for a next predicted surface point.

43. The system of claim 40, wherein said executable instructions further comprise:

instructions for calculating the curvature of the surface; and instructions for deriving said range measurements at calculated point spacings on the surface, said calculated point spacings determined at least in part by said calculated curvature.

44. The system of claim 40, further comprising instructions for operating said ranging system in a normalizing mode that generates said plurality of range measurements as a function of normal orientations between the surface and said ranging device.

45. The system of claim 40, further comprising instructions for operating said ranging system in a pivoting mode that generates said plurality of range measurements between the surface and said ranging system through a pivot point, said pivot point being a predetermined distance removed from an obstructing surface of the object.

46. The system of claim 45, wherein said pivoting mode operating instructions comprise:

instructions for deriving said range measurements in a pivoting mode as a function of orientations between the surface and said ranging device through a pivot point;

instructions for beginning said pivoting mode in a first direction; and instructions for changing the direction of said pivoting mode in the event that the incidence angle between the surface and said ranging device exceeds a predetermined incidence angle limit and further that to decrease the incidence angle requires movement of said ranging device in the direction of said obstruction.

47. The system of claim 40, wherein said adaptive switching instructions comprise instructions for adaptively switching from said second mode to said first mode of deriving said range measurements in the event that the incidence angle of orientation between the surface and said ranging device exceeds a predetermined incidence angle limit and further that to decrease said incidence angle requires movement of said ranging device in the direction away from said obstruction.

48. The system of claim 40, further comprising instructions for deriving said range measurements at calculated point spacings in said range measurement, said calculated point spacings being within a point spacing range, said point spacing range comprising a minimum acceptable point spacing and a maximum acceptable point spacing.

49. The system of claim 48, further comprising instructions for identifying an edge on the surface in the event that no measured surface point appears within said surface point spacing range.

50. The system of claim 49, further comprising instructions for reversing the relative direction of movement between the object and said ranging device in the event that an edge condition exists and no prior direction reversal has already occurred.

51. The system of claim 49, further comprising instructions for determining that a surface contour is complete in the event that an edge condition exists and a prior direction reversal has already occurred.

52. The system of claim 40, further comprising:

instructions for storing all measured surface points beyond said predetermined acceptance criteria as rejected points;

instructions for determining whether all rejected points correspond to any previously measured contour upon finishing a contour of the surface;

instructions for identifying a next contour of the cross-section in the event that any rejected points fail to belong to surface points on any said previous contour; and instructions for scanning said next contour using at least one of said non-belonging rejected points as a first point on said next contour.

* * * * *